US008546588B2

(12) United States Patent  (10) Patent No.: US 8,546,588 B2
Blackburn et al.  (45) Date of Patent: Oct. 1, 2013

(54) SUBSTITUTED HYDROXAMIC ACIDS AND USES THEREOF

(75) Inventors: Christopher Blackburn, Natick, MA (US); Kenneth M. Gigstad, Westford, MA (US); He Xu, Needham, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/034,947

(22) Filed: Feb. 25, 2011

(65) Prior Publication Data
US 2011/0213003 A1 Sep. 1, 2011

Related U.S. Application Data

(60) Provisional application No. 61/339,117, filed on Feb. 26, 2010, provisional application No. 61/426,248, filed on Dec. 22, 2010.

(51) Int. Cl.
A61K 31/381 (2006.01)
C07D 333/46 (2006.01)

(52) U.S. Cl.
USPC ............... 549/57; 549/72; 549/487; 546/193; 546/209; 546/212; 546/214; 546/270.4; 548/181; 548/200; 548/206; 548/245; 548/467; 548/527; 514/318; 514/326; 514/342; 514/343; 514/340; 514/365; 514/372; 514/374; 514/378; 514/448; 514/471

(58) Field of Classification Search
USPC ..................................................... 549/57, 72
See application file for complete search history.

(56) References Cited

U.S. PATENT DOCUMENTS

| 5,034,049 A * | 7/1991 | Kober et al. ................. 504/289 |
| 5,442,110 A | 8/1995 | Isomura et al. |
| 5,776,983 A | 7/1998 | Washburn et al. |
| 6,541,661 B1 | 4/2003 | Delorme et al. |
| 7,098,241 B2 | 8/2006 | Grossmann et al. |
| 7,250,514 B1 | 7/2007 | Xiao |
| RE39,850 E | 9/2007 | Delorme et al. |
| 7,345,043 B2 | 3/2008 | Anandan et al. |
| 7,396,944 B2 | 7/2008 | Fertig et al. |
| 2003/0187009 A1 | 10/2003 | Wentland |
| 2005/0119305 A1 | 6/2005 | Naka et al. |
| 2005/0148613 A1 | 7/2005 | Van Emelen et al. |
| 2006/0004041 A1 | 1/2006 | Cummings et al. |
| 2006/0058553 A1 | 3/2006 | Leahy et al. |
| 2006/0100285 A1 | 5/2006 | Pinori et al. |
| 2006/0252834 A1 | 11/2006 | Rho et al. |
| 2007/0213392 A1 | 9/2007 | Miller et al. |
| 2009/0137679 A1 | 5/2009 | Chen et al. |
| 2011/0039827 A1 | 2/2011 | Blackburn et al. |
| 2011/0046157 A1 | 2/2011 | Blackburn et al. |
| 2011/0212969 A1 | 9/2011 | Blackburn et al. |
| 2011/0213003 A1 | 9/2011 | Blackburn et al. |
| 2012/0053201 A1 | 3/2012 | Blackburn et al. |
| 2012/0165316 A1 | 6/2012 | Gould |

FOREIGN PATENT DOCUMENTS

| EP | 659737 | 6/1995 |
| WO | WO 2005/086898 A2 | 9/2005 |
| WO | WO 2005/108367 A1 | 11/2005 |
| WO | WO 2005/121120 A1 | 12/2005 |
| WO | WO 2007/100657 A2 | 9/2007 |
| WO | WO 2007/115408 A1 | 10/2007 |
| WO | WO 2007/115410 A1 | 10/2007 |
| WO | WO 2009/015237 A1 | 1/2009 |
| WO | WO 2009/026446 A8 | 2/2009 |
| WO | WO 2009/037001 A1 | 3/2009 |
| WO | WO 2009/112550 A1 | 9/2009 |
| WO | WO 2009/129335 A2 | 10/2009 |
| WO | WO 2010/151317 A1 | 12/2010 |
| WO | WO 2010/151318 A1 | 12/2010 |
| WO | WO 2011/106627 A1 | 9/2011 |
| WO | WO 2011/106632 A1 | 9/2011 |
| WO | WO 2012/027564 A1 | 3/2012 |
| WO | WO 2012/088015 A2 | 6/2012 |

OTHER PUBLICATIONS

International Search Report of the International Searching Authority dated Apr. 12, 2011 issued in International Application No. PCT/US2011/26224, which corresponds to U.S. Appl. No. 13/034,974.
Office Action dated Apr. 16, 2013 in pending U.S. Appl. No. 13/034,974.
Hubbs, Jed L. et al., "Amino Acid Derivatives as Histone Deacetylase Inhibitors," *Bioorganic & Medicinal Chemistry Letters*, vol. 18, (2008) pp. 34-38.
Wilson, Kevin J. et al., "Phenylglycine and Phenylalanine Derivatives as Potent and Selective HDAC1 Inhibitors (SHI-1)," *Bioorganic & Medicinal Chemistry Letters*, vol. 18, (2008) pp. 1859-1863.
Shinji, Chihiro, et al. "Design and synthesis of phthalimide-type histone deacetylase inhibitors," *Bioorganic &. Medicinal Chemistry Letters*, vol. 15, No. 20 (2005) pp. 4427-4431.
Yang, Xiang-Jiao, et al., "The Rpd3/Hda1 family of lysine deacetylases: from bacteria and yeast to mice and men," *Nature Reviews*, vol. 9 (Mar. 2008) pp. 206-218.
Kawaguchi, Yoshiharu, et al., "The deacetylase HDAC6 regulates aggresome formation and cell viability in response to misfolded protein stress," *Cell*, vol. 115 (Dec. 12, 2003) pp. 727-738.
Simms-Waldrip, Tiffany, et al., "The aggresome pathway as a target for therapy in hematologic malignancies," *Molecular Genetics and Metabolism*, vol. 94 (2008) pp. 283-286.
Kapoor, Shailendra, Letter to the Editor, "Inhibition of HDAC6-dependent carcinogenesis: emerging, new therapeutic options besides belinostat," *International Journal of Cancer*, vol. 124 (2009) p. 509.

(Continued)

*Primary Examiner* — Laura L. Stockton
(74) *Attorney, Agent, or Firm* — Millennium Pharmaceuticals, Inc.

(57) ABSTRACT

This invention provides compounds of formula (I): (I)

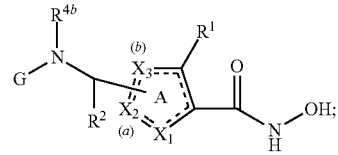

wherein $X_1$, $X_2$, $X_3$, $R^2$, $R^{4b}$, $R^1$, and G have values as described in the specification, useful as inhibitors of HDAC6. The invention also provides pharmaceutical compositions comprising the compounds of the invention and methods of using the compositions in the treatment of proliferative, inflammatory, infectious, neurological or cardiovascular diseases or disorders.

19 Claims, No Drawings

(56) References Cited

OTHER PUBLICATIONS

Iwata, Atsushi, et al., "HDAC6 and microtubules are required for autophagic degradation of aggregated huntingtin," *The Journal of Biological Chemistry*, vol. 280, No. 48 (Dec. 2, 2005) pp. 40282-40292.

Ding, Wen-Xing, et al., "Linking of autophagy to ubiquitin-proteasome system is important for the regulation of endoplasmic reticulum stress and cell viability," *The American Journal of Pathology*, vol. 171, No. 2 (Aug. 2007) pp. 513-524.

Park, Jung-Hyun, et al. "Class II histone deacetylases play pivotal roles in heat shock protein 90-mediated proteasomal degradation of vascular endothelial growth factor receptors," *Biochemical and Biophysical Research Communications*, vol. 368 (2008) pp. 318-322.

Carta, Sonia, et al., "Histone deacetylase inhibitors prevent exocytosis of interleukin-1β-containing secretory lysosomes: role of microtubules," *Blood*, vol. 108, No. 5 (Sep. 1, 2006) pp. 1618-1626.

Mendrysa, Susan M., et al., "An integrated genetic-genomic approach for the identification of novel cancer loci in mice sensitized to c-Myc-induced apoptosis," *Genes & Cancer*, vol. 1, No. 5 (2010) pp. 465-479.

Namdar, Mandana, et al., "Selective inhibition of histone deacetylase 6 (HDAC6) induces DNA damage and sensitizes transformed cells to anticancer agents," *Proceedings of the National Academy of Sciences*, vol. 107, No. 46 (Nov. 16, 2010) (published on-line before print on Oct. 29, 2010 at: http://www.pnas.org/cgi/doi/10.1073/pnas.1013754107).

Tran, Andy Dong-Anh, et al., "HDAC6 deacetylation of tubulin modulates dynamics of cellular adhesions," *Journal of Cell Science*, vol. 120, No. 8 (2007) pp. 1469-1479.

Hubbert, Charlotte, et al., "HDAC6 is a microtubule-associated deacetylase," *Nature*, vol. 417, (May 23, 2002) pp. 455-458.

Kawada, Junichi, et al., "Tubacin kills Epstein-Barr virus (EBV)-Burkitt lymphoma cells by inducing reactive oxygen species and EBV lymphoblastoid cells by inducing apoptosis," *The Journal of Biological Chemistry*, vol. 284 (Jun. 19, 2009) pp. 17102-17109 (first published online on Apr. 22, 2009 at: http://www.jbc.org/cgi/doi/10.1074/jbc.M809090200).

Kaluza, David, et al., "Class IIb HDAC6 regulates endothelial cell migration and angiogenesis by deacetylation of cortactin," *The EMBO Journal* (2011) pp. 1-15.

d'Ydewalle, Constantin, et al., "HADC6 inhibitors reverse axonal loss in a mouse model of mutant HSPB1-induced Charcot-Marie-Tooth disease," *Nature Medicine*, vol. 17, No. 8 (Aug. 2011) pp. 968-974.

Haggarty, Stephen J., et al., "Domain-selective small-molecule inhibitor of histone deacetylase 6 (HDAC6)-mediated tubulin deacetylation," *Proceedings of the National Academy of Sciences*, vol. 100, No. 8 (Apr. 15, 2003) pp. 4389-4394.

Itoh, Yukihiro, et al., "Design, synthesis, structure-selectivity relationship, and effect on human cancer cells of a novel series of histone deacetylase 6-selective inhibitors," *Journal of Medicinal Chemistry*, vol. 50 (2007) pp. 5425-5438.

Butler, Kyle V., et al., "Rational design and simple chemistry yield a superior, neuroprotective HDAC6 inhibitor, tubastatin A," *Journal of the American Chemical Society*, vol. 132 (2010) pp. 10842-10846.

Yao, Tso-Pang, "The role of ubiquitin in autophagy-dependent protein aggregate processing," *Genes & Cancer*, vol. 1, No. 7 (2010) pp. 779-786.

Li, Guoyi, et al., "HDAC6 α-tubulin deacetylase: a potential therapeutic target in neurodegenerative diseases," *Journal of the Neurological Sciences*, vol. 304 (2011) pp. 1-8.

Lee, Joo-Yong, et al., "Quality control autophagy a joint effort of ubiquitin, protein deacetylase and actin cytoskeleton," *Autophagy*, vol. 6, No. 4 (May 16, 2010) pp. 555-557.

Tapia, Monica, et al., "Impaired Function of HDAC6 slows down axonal growth and interferes with axon initial segment development," *PLoS ONE*, vol. 5, No. 9 (Sep. 2010) e12908, pp. 1-13.

Cabrero, J. Roman, et al., "Lymphocyte chemotaxis is regulated by histone deacetylase 6, independently of its deacetylase activity," *Molecular Biology of the Cell*, vol. 17 (Aug. 2006) pp. 3435-3445.

Bobrowska, Anna, et al., "Hdac6 knock-out increases tubulin acetylation but does not modify disease progression in the R6/2 mouse model of Huntington's disease," *PLoS ONE*, vol. 6, No. 6 (Jun. 2011) e20696, pp. 1-11.

Fiesel, Fabienne C., et al., "TDP-43 knockdown impairs neurite outgrowth dependent on its target histone deacetylase 6," *Molecular Neurodegeneration*, vol. 6, No. 64 (2011) pp. 1-10.

Lemon, Douglas D., et al., "Cardiac HDAC6 catalytic activity is induced in response to chronic hypertension," *Journal of Molecular and Cellular Cardiology* (2011) doi:10.1016/j.yjmcc.2011.04.005.

Olzmann, J.A., et al., "Aggresome formation and neurodegenerative diseases: therapeutic implications," *Current Medicinal Chemistry*, vol. 15 (2008) pp. 47-60.

Zhu, Jianzhong, et al., "PKC alpha regulates Sendai virus-mediated interferon induction through HDAC6 and 13-catenin," *The EMBO Journal*, vol. 30 (2011) pp. 4838-4849.

Zhang, Zhenhuan, et al., "HDAC6 expression is correlated with better survival in breast cancer," *Clinical Cancer Research*, vol. 10 (Oct. 5, 2004) pp. 6962-6968.

Fiesel, Fabienne C., et al., "Knockdown of transactive response DNA-binding protein (TDP-43) downregulates histone deacetylase 6," *The EMBO Journal*, vol. 29 (2010) pp. 209-221.

Beurel, Eleonore, "HDAC6 regulates LPS-tolerance in astrocytes," *PLoS ONE*, vol. 6, No. 10 (Oct. 2011) e25804, pp. 1-8.

Miki, Yasuo, et al., "Accumulation of histone deacetylase 6, an aggresome-related protein, is specific to Lewy bodies and glial cytoplasmic inclusions," *Neuropathology*, vol. 31, No. 6 (Dec. 2011) pp. 561-568 (first published online on Feb. 1, 2011: doi:10.1111/j.1440-1789.2011.01200.x.

Kim, In Ah, et al., "Epigenetic modulation of radiation response in human cancer cells with activated EGFR or HER-2 signaling: potential role of histone deacetylase 6," *Radiotherapy and Oncology*, vol. 92 (2009) pp. 125-132.

Mellado, Begona, et al., "Molecular biology of androgen-independent prostate cancer: the role of the androgen receptor pathway," *Clinical & Transational Oncology*, vol. 11 (2009) pp. 5-10.

Bhalla, K.N., et al., "Inhibition of histone deacetylase (HDAC) 6 sensitizes human leukemia and breast cancer cells to antagonists of heat shock protein (hsp) 90 and/or bortezomib (BZ)," *Journal of Clinical Oncology*, Abstract, 2006 ASCO Annual Meeting Proceedings (Post-Meeting Edition), vol. 24, No. 18S (Jun. 20, 2006 Supplement) (2006) p. 13039.

Dompierre, Jim P., "Histone deacetylase 6 inhibition compensates for the transport deficit in Huntington's disease by increasing tubulin acetylation," *The Journal of Neuroscience*, vol. 27, No. 13 (Mar. 28, 2007) pp. 3571-3583.

Kazantsev, Aleksey G., et al., "Therapeutic application of histone deacetylase inhibitors for central nervous system disorders," *Nature Reviews*, vol. 7 (Oct. 2008) pp. 854-868.

Dhakal, Bijaya K., et al., "Uropathogenic *Escherichia coli* invades host cells via an HDAC6-modulated microtubule-dependent pathway," *Journal of Biological Chemistry*, vol. 284, No. 1 (Jan. 2, 2009) pp. 446-454.

Perez, Mar, et al., "Tau—an inhibitor of deacetylase HDAC6 function," *Journal of Neurochemistry*, vol. 109 (2009) pp. 1756-1766.

Pugacheva, Elena N., et al., "HEF1-dependent aurora A activation induces disassembly of the primary cilium," *Cell*, vol. 129 (Jun. 29, 2007) pp. 1351-1363.

Gao, Ya-sheng, et al., "The microtubule-associated histone deacetylase 6 (HDAC6) regulates epidermal growth factor receptor (EGFR) endocytic trafficking and degradation," *Journal of Biological Chemistry*, vol. 285, No. 15 (Apr. 9, 2010) pp. 11219-11226.

Tannous, Paul, et al., "Intracellular protein aggregation is a proximal trigger of cardiomyocyte autophagy," *Circulation Journal of the American Heart Association*, vol. 117 (2008) pp. 3070-3078 (published online before print Jun. 9, 2008 at: doi:10.1161/CIRCULATIONAHA.107.763870).

Rao, Rekha, et al., "HDAC6 inhibition enhances 17-AAG-mediated abrogation of hsp90 chaperone function in human leukemia cells," *Blood*, vol. 112, No. 5 (Sep. 1, 2008) pp. 1886-1893.

Zhou, Jun, et al., "The protein farnesyltransferase regulates HDAC6 activity in a microtubule-dependent manner," *Journal of Biological Chemistry*, vol. 284, No. 15 (Apr. 10, 2009) pp. 9648-9655.

Cha, Tai-Lung, et al., "Dual degradation of aurora A and B kinases by the histone deacetylase inhibitor LBH589 induces G2-M arrest and apoptosis of renal cancer cells," *Clinical Cancer Research*, vol. 15, No. 3 (Feb. 1, 2009) pp. 840-850.

Kozikowski, Alan P., "Functional differences in epigenetic modulators-superiority of mercaptoacetamide-based histone deacetylase inhibitors relative to hydroxamates in cortical neuron neuroprotection studies," *Journal of Medicinal Chemistry*, vol. 50 (2007) pp. 3054-3061.

Boyault, C., et al., "HDAC6, at the crossroads between cytoskeleton and cell signaling by acetylation and ubiquitination," *Oncogene*, vol. 26 (2007) pp. 5468-5476.

Saunders, L.R., et al., "Sirtuins: critical regulators at the crossroads between cancer and aging," *Oncogene*, vol. 26 (2007) pp. 5489-5504.

Li, Yu, et al., "HDAC6 is required for epidermal growth factor-induced 13-catenin nuclear localization," *Journal of Biological Chemistry*, vol. 283, No. 19 (May 9, 2008) pp. 12686-12690.

Fiskus, Warren, et al., "Molecular and biologic characterization and drug sensitivity of pan-histone deacetylase inhibitor-resistant acute myeloid leukemia cells," *Blood*, vol. 112, No. 7 (Oct. 1, 2008) pp. 2896-2905.

Nawrocki, Steffan T., et al., "Aggresome disruption: a novel strategy to enhance bortezomib-induced apoptosis in pancreatic cancer cells," *Cancer Research*, vol. 66, No. 7 (Apr. 1, 2006) pp. 3773-3781.

Boyault, Cyril, et al., "HDAC6-p97/VCP controlled polyubiquitin chain turnover," *The EMBO Journal*, vol. 25 (2006) pp. 3357-3366.

Hideshima, Teru, et al., "Small-molecule inhibition of proteasome and aggresome function induces synergistic antitumor activity in multiple myeloma," *Proceedings of the National Academy of Sciences*, vol. 102, No. 24 (Jun. 14, 2005) pp. 8567-8572.

Rivieccio, Mark A., et al., "HDAC6 is a target for protection and regeneration following injury in the nervous system," *Proceedings of the National Academy of Sciences*, vol. 106, No. 46 (Nov. 17, 2009) pp. 19599-19604.

Parmigiani, R.B., et al., "HDAC6 is a specific deacetylase of peroxiredoxins and is involved in redox regulation," *Proceedings of the National Academy of Sciences*, vol. 105, No. 28 (Jul. 15, 2008) pp. 9633-9638.

Matthias, Patrick, et al., "HDAC6 a new cellular stress surveillance factor," *Cell Cycle*, vol. 7, No. 1 (Jan. 1, 2008) pp. 7-10.

Rodriguez-Gonzalez, Agustin, et al., "Role of the aggresome pathway in cancer: targeting histone deacetylase 6-dependent protein degradation," *Cancer Research*, vol. 68, No. 8 (Apr. 15, 2008) pp. 2557-2559.

Lee, Yi-Shan, et al., "The cytoplasmic deacetylase HDAC6 is required for efficient oncogenic tumorigenesis," *Cancer Research*, vol. 68, No. 18 (Sep. 15, 2008) pp. 7561-7569.

Lee, Joo-Yong, et al., "HDAC6 controls autophagosome maturation essential for ubiquitin-selective quality-control autophagy," *The EMBO Journal*, vol. 29 (2010) pp. 969-980.

Kannennura, Kazuo, et al., "Effects of downregulated HDAC6 expression on the proliferation of lung cancer cells," *Biochemical and Biophysical Research Communications*, vol. 374 (2008) pp. 84-89.

Crabbe, Tom, et al., "The P13K inhibitor arsenal: choose your weapon!" *Trends in Biochemical Sciences*, vol. 32, No. 10 (2007) pp. 45-456.

Pandey, Udai Bhan, et al., "HDAC6 rescues neurodegeneration and provides an essential link between autophagy and the UPS," *Nature*, vol. 447 (Jun. 14, 2007) pp. 859-863.

Zhang, Xiaochong, et al., "HDAC6 modulates cell motility by altering the acetylation level of cortactin," *Molecular Cell*, vol. 27 (Jul. 20, 2007) pp. 197-213.

Deribe, Yonathan Lissanu, et al., "Regulation of epidermal growth factor receptor trafficking by lysine deacetylase HDAC6," *Science Signaling*, vol. 2, No. 102 (Dec. 22, 2009) ra84 pp. 1-12 (published online at: DOI: 10.1126/scisignal.2000576).

Park, Jung-Hyun, et al., "Inhibitors of histone deacetylases induce tumor-selective cytotoxicity through modulating Aurora-A kinase," *Journal of Molecular Medicine*, vol. 86 (2008) pp. 117-128.

Bazzaro, Martina, et al., "Ubiquitin proteasome system stress underlies synergistic killing of ovarian cancer cells by bortezomib and novel HDAC6 inhibitor," *Clinical Cancer Research*, vol. 14, No. 22 (Nov. 15, 2008) pp. 7340-7347.

Shan, Bin, et al., "Requirement of HDAC6 for transforming growth factor-β1-induced epithelial-mesenchymal transition," *Journal of Biological Chemistry*, vol. 283, No. 30 (Jul. 25, 2008) pp. 21065-21073.

Kalveram, Birte, et al., "The ubiquitin-like modifier FAT10 interacts with HDAC6 and localizes to aggresomes under proteasome inhibition," *Journal of Cell Science*, vol. 121, No. 24 (2008) pp. 4079-4088.

Valenzuela-Fernandez, Agustin, et al., "HDAC6: a key regulator of cytoskeleton, cell migration and cell-cell interactions," *Trends in Cell Biology*, vol. 18, No. 6 (2008) pp. 291-297.

Du, Guiping, et al., "To prevent neurodegeneration HDAC6 uses different strategies for different challenges," *Communicative & Integrative Biology*, vol. 4, No. 2 (Mar./Apr. 2011) pp. 139-142.

Paris, Marielle, et al., "Histone deacetylase inhibitors: from bench to clinic," *Journal of Medicinal Chemistry*, Vo. 51, No. 6 (Mar. 27, 2008) pp. 1505-1529.

Santo L. et al., "Selective Inhibition of HDAC6 with a New Prototype Inhibitor (ACY-1215) Overcomes Bortezomib Resistance in Multiple Myeloma (MM)," *Blood*, (ASH Annual Meeting Abstracts) (2010) 116: Abstract 2997.

International Search Report and Written Opinion of the International Searching Authority dated Apr. 29, 2011 issued in International Application No. PCT/US2011/26216, which corresponds to U.S. Appl. No. 13/034,947.

Gavai, A.V. et al., "BMS-196085: a Potent and Selective Full Agonist of the Human $β_3$ Adrenergic Receptor," *Bioorganic & Medicinal Chemistry Letters*, vol. 11, (2001) pp. 3041-3044.

Smil, David V. et al., "Novel HDAC6 Isoform Selective Chiral Small Molecule Histone Deacetylase Inhibitors," *Bioorganic & Medicinal Chemistry Letters*, vol. 19, (2009) pp. 688-692.

* cited by examiner

SUBSTITUTED HYDROXAMIC ACIDS AND USES THEREOF

PRIORITY CLAIM

This application claims the benefit under 35 U.S.C. §119 (e) of U.S. Provisional Patent Application Ser. No. 61/339,117, filed Feb. 26, 2010, incorporated by reference in its entirety, and U.S. Provisional Patent Application Ser. No. 61/426,248, filed Dec. 22, 2010, incorporated by reference in its entirety.

FIELD OF THE INVENTION

The invention relates to compounds and methods for the selective inhibition of HDAC6. The present invention relates to compounds useful as HDAC6 inhibitors. The invention also provides pharmaceutical compositions comprising the compounds of the invention and methods of using the compositions in the treatment of various diseases.

BACKGROUND OF THE INVENTION

Histone deacetylase 6 (HDAC6) is a member of a family of amidohydrolases commonly referred as histone or lysine deacetylases (HDACs or KDACs) as they catalyze the removal of acetyl groups from the ε-amino group of lysine residues from proteins. The family includes 18 enzymes which can be divided in 3 main classes based on their sequence homology to yeast enzymes Rpd3 (Class I), Hda1 (Class II) and Sir2 (Class III). A fourth class was defined with the finding of a distinct mammalian enzyme—HDAC11 (reviewed in Yang, et al., *Nature Rev. Mol. Cell Biol.* 2008, 9:206-218 and in Saunders and Verdin, *Oncogene* 2007, 26(37):5489-5504). Biochemically, Class I (HDAC1, 2, 3, 8) and Class II (HDAC4, 5, 6, 7, 9, 10) and Class IV (HDAC11) are $Zn^{2+}$-dependent enzymes, while Class III (SIRT1-7) are dependent on nicotinamide adenine dinucleotide ($NAD^+$) for activity. Unlike all other HDACs, HDAC6 resides primarily in the cytosol. It has 2 functional catalytic domains and a carboxy-terminal $Zn^{2+}$-finger ubiquitin binding domain that binds ubiquitinated misfolded proteins (Kawaguchi et al., *Cell* 2003, 115(6):727-738), ubiquitin (Boyaullt et al., *EMBO J.* 2006, 25(14): 3357-3366), as well as ubiquitin-like FAT10 modifier (Kalveram et al., *J. Cell Sci.* 2008, 121(24):4079-4088). Known substrates of HDAC6 include cytoskeletal proteins α-tubulin and cortactin; β-catenin which forms part of adherens junctions and anchors the actin cytoskeleton; the chaperone Hsp90; and the redox regulatory proteins peroxiredoxin (Prx) I and Prx II (reviewed in Boyault et al., *Oncogene* 2007, 26(37):5468-5476; Matthias et al., *Cell Cycle* 2008, 7(1):7-10; Li et al., *J Biol. Chem.* 2008, 283(19):12686-12690; Parmigiani et al., *Proc. Natl. Acad. Sci. USA* 2009, 105(28):9633-9638). Thus, HDAC6 mediates a wide range of cellular functions including microtubule-dependent trafficking and signaling, membrane remodeling and chemotactic motility, involvement in control of cellular adhesion, ubiquitin level sensing, regulation of chaperone levels and activity, and responses to oxidative stress. All of these functions may be important in tumorigenesis, tumor growth and survival as well as metastasis (Simms-Waldrip et al., *Mol. Genet. Metabolism* 2008, 94(3):283-286; Rodriguez-Gonzalez et al., *Cancer Res.* 2008, 68(8):2557-2560; Kapoor, *Int. J. Cancer* 2009, 124:509; Lee et al., *Cancer Res.* 2008, 68(18):7561-7569). Recent studies have shown HDAC6 to be important in autophagy, an alternative pathway for protein degradation that compensates for deficiencies in the activity of the ubiquitin proteasome system or the expression of proteins prone to form aggregates and can be activated following treatment with a proteasome inhibitor (Kawaguchi et al., *Cell* 2003, 115(6):727-738; Iwata et al., *J. Biol. Chem.* 2005, 280(48): 40282-40292; Ding et al., *Am. J. Pathol.* 2007, 171:513-524, Pandey et al., *Nature* 2007, 447(7146):860-864). Although the molecular mechanistic details are not completely understood, HDAC6 binds ubiquitinated or ubiquitin-like conjugated misfolded proteins which would otherwise induce proteotoxic stress and then serves as an adaptor protein to traffic the ubiquitinated cargo to the microtubule organizing center using the microtubule network via its known association with dynein motor protein. The resulting perinuclear aggregates, known as aggresomes, are then degraded by fusion with lysosomes in an HDAC6- and cortactin-dependent process which induces remodeling of the actin cytoskeleton proximal to aggresomes (Lee et al., *EMBO J.* 2010, 29:969-980). In addition, HDAC6 regulates a variety of biological processes dependent on its association with the microtubular network including cellular adhesion (Tran et al., *J. Cell Sci.* 2007, 120(8):1469-1479) and migration (Zhang et al., *Mol. Cell.* 2007, 27(2):197-213; reviewed in Valenzuela-Fernandez et al., *Trends Cell. Biol.* 2008, 18(6):291-297), epithelial to mesenchymal transition (Shan et al., *J. Biol. Chem.* 2008, 283 (30):21065-21073), resistance to anoikis (Lee et al., *Cancer Res.* 2008, 68(18):7561-7569), epithelial growth factor-mediated Wnt signaling via β-catenin deacetylation (Li et al., *J. Biol. Chem.* 2008, 283(19):12686-12690) and epithelial growth factor receptor stabilization by endocytic trafficking (Lissanu Deribe et al., *Sci. Signal.* 2009, 2(102): ra84; Gao et al., *J. Biol. Chem.* 2010, 285:11219-11226); all events that promote oncogenesis and metastasis (Lee et al., *Cancer Res.* 2008, 68(18):7561-7569). HDAC6 activity is known to be upregulated by Aurora A kinase in cilia formation (Pugacheva et al., *Cell* 2007, 129(7):1351-1363) and indirectly by farnesyl transferase with which HDAC6 forms a complex with microtubules (Zhou et al., *J. Biol. Chem.* 2009, 284(15): 9648-9655). Also, HDAC6 is negatively regulated by tau protein (Perez et al., *J. Neurochem.* 2009, 109(6):1756-1766).

Diseases in which selective HDAC6 inhibition could have a potential benefit include cancer (reviewed in Simms-Waldrip et al., *Mol. Genet. Metabolism* 2008, 94(3):283-286 and Rodriguez-Gonzalez et al., *Cancer Res.* 2008, 68(8):2557-2560), specifically: multiple myeloma (Hideshima et al., *Proc. Natl. Acad. Sci. USA* 2005, 102(24):8567-8572); lung cancer (Kamemura et al., *Biochem. Biophys. Res. Commun.* 2008, 374(1):84-89); ovarian cancer (Bazzaro et al., *Clin. Cancer Res.* 2008, 14(22):7340-7347); breast cancer (Lee et al., *Cancer Res.* 2008, 68(18):7561-7569); prostate cancer (Mellado et al., *Clin. Trans. Onco.* 2009, 11(1):5-10); pancreatic cancer (Nawrocki et al., *Cancer Res.* 2006, 66(7): 3773-3781); renal cancer (Cha et al., *Clin. Cancer Res.* 2009, 15(3):840-850); and leukemias such as acute myeloid leukemia (AML) (Fiskus et al., *Blood* 2008, 112(7):2896-2905) and acute lymphoblastic leukemia (ALL) (Rodriguez-Gonzalez et al., *Blood* 2008, 112(11): Abstract 1923).

Inhibition of HDAC6 may also have a role in cardiovascular disease, i.e. cardiovascular stress, including pressure overload, chronic ischemia, and infarction-reperfusion injury (Tannous et al., *Circulation* 2008, 117(24):3070-3078); bacterial infection, including those caused by uropathogenic *Escherichia coli* (Dhakal and Mulve, *J. Biol. Chem.* 2008, 284(1):446-454); neurological diseases caused by accumulation of intracellular protein aggregates such as Huntington's disease (reviewed in Kazantsev et al., *Nat. Rev. Drug Disc.* 2008, 7(10):854-868; see also Dompierre et al., *J. Neurosci.* 2007, 27(13):3571-3583; Kozikowski et al., *J. Med. Chem.*

2007, 50:3054-3061) or central nervous system trauma caused by tissue injury, oxidative-stress induced neuronal or axomal degeneration (Rivieccio et al., *Proc. Natl. Acad. Sci. USA* 2009, 106(46):19599-195604); and inflammation, including reduction of pro-inflammatory cytokine IL-1β (Carta et al., *Blood* 2006, 108(5):1618-1626), increased expression of the FOXP3 transcription factor, which induces immunosuppressive function of regulatory T-cells resulting in benefits in chronic diseases such as rheumatoid arthritis, psoriasis, multiple sclerosis, lupus and organ transplant rejection (reviewed in Wang et al., *Nat. Rev. Drug Disc.* 2009, 8(12):969-981).

Given the complex function of HDAC6, selective inhibitors could have potential utility when used alone or in combination with other chemotherapeutics such as microtubule destabilizing agents (Zhou et al., *J. Biol. Chem.* 2009, 284 (15): 9648-9655); Hsp90 inhibitors (Rao et al., *Blood* 2008, 112(5)1886-1893); inhibitors of Hsp90 client proteins, including receptor tyrosine kinases such as Her-2 or VEGFR (Bhalla et al., *J. Clin. Oncol.* 2006, 24(18S): Abstract 1923; Park et al., *Biochem. Biophys. Res. Commun.* 2008, 368(2): 318-322), and signaling kinases such as Bcr-Abl, Akt, mutant FLT-3, c-Raf, and MEK (Bhalla et al., *J. Clin. Oncol.* 2006, 24(18S): Abstract 1923; Kamemura et al., *Biochem. Biophys. Res. Commun.* 2008, 374(1):84-89); inhibitors of cell cycle kinases Aurora A and Aurora B (Pugacheva et al., *Cell* 2007, 129(7):1351-1363; Park et al., *J. Mol. Med.* 2008, 86(1):117-128; Cha et al., *Clin. Cancer Res.* 2009, 15(3):840-850); EGFR inhibitors (Lissanu Deribe et al., *Sci. Signal.* 2009, 2(102): ra84; Gao et al., *J. Biol. Chem.* 2010, 285:11219-11226) and proteasome inhibitors (Hideshima et al., *Proc. Natl. Acad. Sci. USA* 2005, 102(24):8567-8572) or other inhibitors of the ubiquitin proteasome system such as ubiquitin and ubiqutin-like activating (E1), conjugation (E2), ligase enzymes (E3, E4) and deubiquitinase enzymes (DUBs) as well as modulators of autophagy and protein homeostasis pathways. In addition, HDAC6 inhibitors could be combined with radiation therapy (Kim et al., *Radiother. Oncol.* 2009, 92(1):125-132.

Clearly, it would be beneficial to provide novel HDAC6 inhibitors that possess good therapeutic properties, especially for the treatment of proliferative diseases or disorders.

DETAILED DESCRIPTION OF THE INVENTION

1. General Description of Compounds of the Invention

The present invention provides compounds that are effective inhibitors of HDAC6. These compounds are useful for inhibiting HDAC6 activity in vitro and in vivo, and are especially useful for the treatment of various cell proliferative diseases or disorders. The compounds of the invention are represented by formula (I):

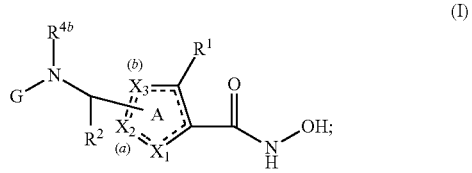

or a pharmaceutically acceptable salt thereof; wherein:

ring A is a heteroaromatic 5-membered ring connected through one of positions (a) or (b);
$X_1$ is $CR^1$, O, or S;
(i) when ring A is connected through position (a), $X_2$ is C; and $X_3$ is $CR^1$, O, S, or N; or
(ii) when ring A is connected through position (b), $X_3$ is C; and $X_2$ is $CR^1$, O, S, or N;
provided that only one of $X_1$, $X_2$, or $X_3$ is O or S;
and further provided that at least one of $X_1$, $X_2$, and $X_3$ is O, S, or N;
each occurrence of $R^1$ is independently hydrogen, halogen, $C_{1-4}$ alkyl, $C_{1-3}$-fluoroalkyl, —O—$C_{1-3}$ alkyl, —O—$C_{1-3}$-fluoroalkyl, cyano, hydroxy, —NHC(O)$C_{1-3}$ alkyl, —C(O)NHC$_{1-3}$alkyl, —NHC(O)NHC$_{1-3}$ alkyl, or —NHS(O)$_2$C$_{1-3}$ alkyl;
ring A is further substituted at a substitutable nitrogen atom with $R^{1a}$;
$R^{1a}$ is hydrogen, or $C_{1-4}$ aliphatic;
$R^2$ is $C_{1-6}$ aliphatic, $C_{1-6}$ fluoroaliphatic, or unsubstituted or substituted 6-10-membered aryl;
$R^{4b}$ is hydrogen, or $C_{1-4}$ aliphatic;
G is —$R^3$, —$V_1$—$R^3$, —$V_1$-$L_1$-$R^3$, -$L_2$-$V_1$—$R^3$, -$L_2$-$V_2$—$R^3$, -$L_1$-$R^3$,
$L_1$ is an unsubstituted or substituted $C_{1-3}$ alkylene chain;
$L_2$ is an unsubstituted or substituted $C_{2-3}$ alkylene chain;
$V_1$ is —C(O)—, —C(O)—$CR^4$=$CR^4$—, —C(O)—N($R^{4a}$)—, —C(O)—O—, or —S(O)$_2$—;
$V_2$ is —C(S)—, —N($R^{4a}$)—, —N($R^{4a}$)—C(O)—, —SO$_2$—N($R^{4a}$)—, —N($R^{4a}$)—SO$_2$—, —O—, —S—, —S(O)—, —N($R^{4a}$)—C(O)—N($R^{4a}$)—, —N($R^{4a}$)—C(O)—O—, —O—C(O)—N($R^{4a}$)—, or —N($R^{4a}$)—SO$_2$—N($R^{4a}$)—;
$R^3$ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur;
each occurrence of $R^4$ is independently hydrogen, fluoro, or unsubstituted or substituted $C_{1-4}$ aliphatic; and
each occurrence of $R^{4a}$ is independently hydrogen, or unsubstituted or substituted $C_{1-4}$ aliphatic.

2. Compounds and Definitions:

Compounds of this invention include those described generally for formula (I) above, and are further illustrated by the classes, subclasses, and species disclosed herein. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted C6-14 aromatic hydrocarbon moiety comprising one to three aromatic rings. Preferably, the aryl group is a C6-10 aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is C6-10 aryl C1-6 alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR+ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —(CH$_2$)$_{n'}$—, wherein n' is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroaralkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —NO$_2$, —CN, —R$^+$, —C(R$^+$)=C(R$^+$)$_2$, —C≡C—R$^+$, —OR$^+$, —SR$^o$, —S(O)R$^o$, —SO$_2$R$^o$, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(=NR$^+$)—N(R$^+$)$_2$, —N(R$^+$)C(=NR$^+$)—R$^o$, —NR$^+$CO$_2$R$^+$, —NR$^+$SO$_2$R$^o$, —NR$^+$SO$_2$N(R$^+$)$^2$, —O—C(O)R$^+$, —O—CO$_2$R$^+$, —OC(O)N(R$^+$)$_2$, —C(O)R$^+$, —C(S)R$^o$, —CO$_2$R$^+$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(=NR$^+$)—N(R$^+$)$_2$, —N(R$^+$)C(=NR$^+$)—N(R$^+$)—C(O)R$^+$, —C(=NR$^+$)—N(R$^+$)$_2$, —C(=NR$^+$)—OR$^+$, —N(R$^+$)—N(R$^+$)$_2$, —C(=NR$^+$)—N(R$^+$)—OR$^+$, —C(R$^o$)=N—OR$^+$, —P(O)(R$^+$)$_2$, —P(O)(OR$^+$)$_2$, —O—P(O)—OR$^+$, and —P(O)(NR$^+$)—N(R$^+$)$_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7-membered aryl, heteroaryl, cycloaliphatic, or heterocyclyl ring. Each R$^o$ is an optionally substituted aliphatic, aryl, heteroaryl, cycloaliphatic, or heterocyclyl group.

An aliphatic or heteroaliphatic group, or a non-aromatic carbocyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R$^o$, =N—NHSO$_2$R$^o$ or =N—R* where R$^o$ is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R+ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R+ (or any other variable similarly defined in the specification and claims herein), are taken together with their intervening atom(s) include, but are not limited to the following: a) two independent occurrences of R+ (or any other variable similarly defined in the specification or claims herein) that are bound to the same atom and are taken together with that atom to form a ring, for example, N(R+)₂, where both occurrences of R+ are taken together with the nitrogen atom to form a piperidin-1-yl, piperazin-1-yl, or morpholin-4-yl group; and b) two independent occurrences of R+ (or any other variable similarly defined in the specification or claims herein) that are bound to different atoms and are taken together with both of those atoms to form a ring, for example where a phenyl group is substituted with two occurrences of OR+

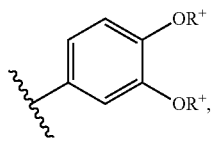

these two occurrences of R+ are taken together with the oxygen atoms to which they are bound to form a fused 6-membered oxygen containing ring:

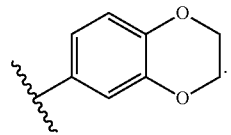 [SMILES: *c1ccc2c(c1)OCCO2]

It will be appreciated that a variety of other rings (e.g., Spiro and bridged rings) can be formed when two independent occurrences of R+ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a 13C- or 14C-enriched carbon are within the scope of this invention. Such compounds are useful, for example, as analytical tools or probes in biological assays.

The terms "stereoisomer", "enantiomer", "diastereomer", "epimer", and "chiral center", are used herein in accordance with the meaning each is given in ordinary usage by those of ordinary skill in the art. Thus, stereoisomers are compounds that have the same atomic connectivity, but differ in the spatial arrangement of the atoms. Enantiomers are stereoisomers that have a mirror image relationship, that is, the stereochemical configuration at all corresponding chiral centers is opposite. Diastereomers are stereoisomers having more than one chiral center, which differ from one another in that the stereochemical configuration of at least one, but not all, of the corresponding chiral centers is opposite. Epimers are diastereomers that differ in stereochemical configuration at only one chiral center.

It is to be understood that, when a disclosed compound has at least one chiral center, the present invention encompasses one enantiomer of the compound, substantially free from the corresponding optical isomer, a racemic mixture of both optical isomers of the compound, and mixtures enriched in one enantiomer relative to its corresponding optical isomer. When a mixture is enriched in one enantiomer relative to its optical isomer, the mixture contains, for example, an enantiomeric excess of at least 50%, 75%, 90%, 95%, 99%, or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer substantially free of other diastereomers, an enantiomeric pair of diastereomers substantially free of other stereoisomers, mixtures of diastereomers, mixtures of enantiomeric pairs of diastereomers, mixtures of diastereomers in which one diastereomer is enriched relative to the other diastereomer(s), and mixtures of enantiomeric pairs of diastereomers in which one enantiomeric pair of diastereomers is enriched relative to the other stereoisomers. When a mixture is enriched in one diastereomer or enantiomeric pair of diastereomers pairs relative to the other stereoisomers, the mixture is enriched with the depicted or referenced diastereomer or enantiomeric pair of diastereomers relative to other stereoisomers for the compound, for example, by a molar excess of at least 50%, 75%, 90%, 95%, 99%, or 99.5%.

As used herein, the term "diastereomeric ratio" refers to the ratio between diastereomers which differ in the stereochemical configuration at one chiral center, relative to a second chiral center in the same molecule. By way of example, a chemical structure with two chiral centers provides four possible stereoisomers: R*R, R*S, S*R, and S*S, wherein the asterisk denotes the corresponding chiral center in each stereoisomer. The diastereomeric ratio for such a mixture of stereoisomers is the ratio of one diastereomer and its enantiomer to the other diastereomer and its enantiomer=(R*R+S*S):(R*S+S*R).

One of ordinary skill in the art will recognize that additional stereoisomers are possible when the molecule has more than two chiral centers. For purposes of the present invention, the term "diastereomeric ratio" has identical meaning in reference to compounds with multiple chiral centers as it does in reference to compounds having two chiral centers. Thus, the term "diastereomeric ratio" refers to the ratio of all compounds having R*R or S*S configuration at the specified chiral centers to all compounds having R*S or S*R configuration at the specified chiral centers. For convenience, this ratio is referred to herein as the diastereomeric ratio at the asterisked carbon, relative to the second specified chiral center.

The diastereomeric ratio can be measured by any analytical method suitable for distinguishing between diastereomeric compounds having different relative stereochemical configurations at the specified chiral centers. Such methods include, without limitation, nuclear magnetic resonance (NMR), gas chromatography (GC), and high performance liquid chromatography (HPLC) methods.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds:

In some embodiments, the compound of formula (I) is represented by:

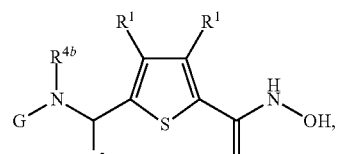
(I-i)

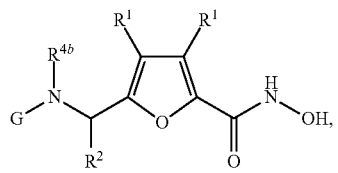
(I-ii)

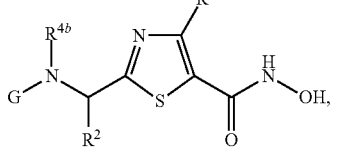
(I-iii)

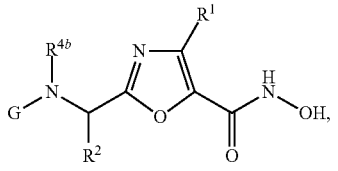
(I-iv)

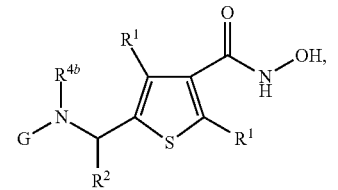
(I-v)

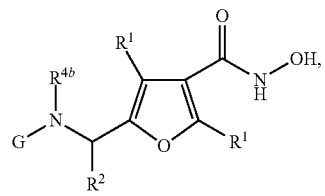
(I-vi)

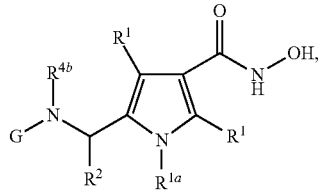
(I-vii)

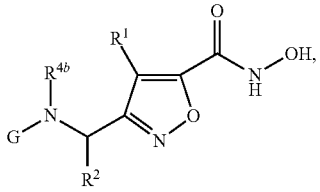
(I-viii)

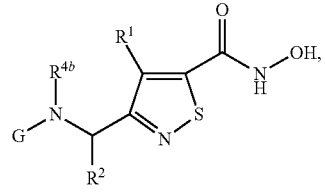
(I-ix)

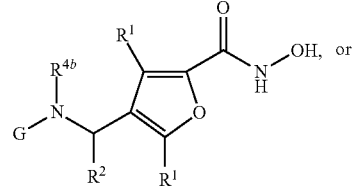
(I-x)

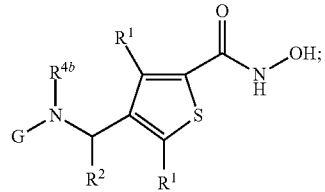
(I-xi)

wherein $R^1$, $R^{1a}$, $R^2$, $R^{4b}$, and G have the values described herein. In certain embodiments, the compound of formula (I) is represented by formulas (I-i) or (I-iii), wherein $R^1$, $R^2$, $R^{4b}$, and G have the values described herein.

In some embodiments, the compound of formula (I) is represented by formula (II-a):

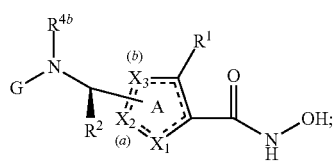
(II-a)

wherein:

ring A is a heteroaromatic 5-membered ring connected through one of positions (a) or (b);

$X_1$ is $CR^1$, O, or S;

(i) when ring A is connected through position (a), $X_2$ is C; and $X_3$ is $CR^1$, O, S, or N; or (ii) when ring A is connected through position (b), $X_3$ is C; and $X_2$ is $CR^1$, O, S, or N;

provided that only one of $X_1$, $X_2$ or $X_3$ is O or S;

and further provided that at least one of $X_1$, $X_2$, and $X_3$ is O, S, or N;

and $R^1$, $R^2$, $R^{4b}$, and G have the values described herein.

In some embodiments, the compound of formula (II-a) is represented by:

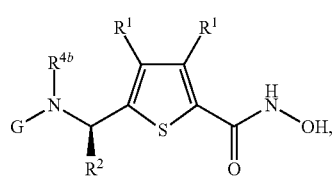
(II-a-i)

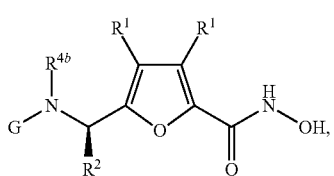
(II-a-ii)

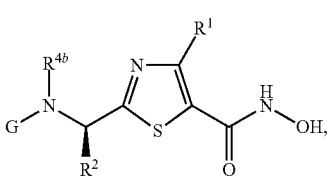
(II-a-iii)

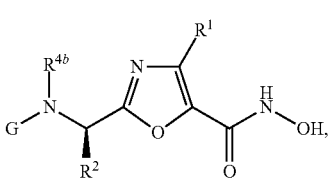
(II-a-iv)

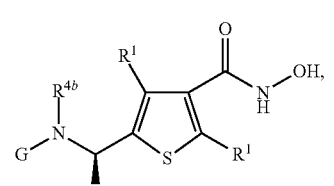
(II-a-v)

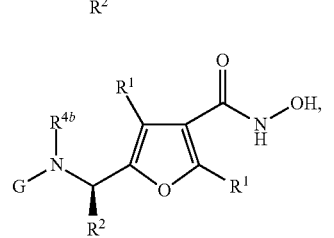
(II-a-vi)

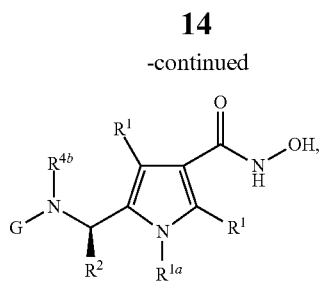
(II-a-vii)

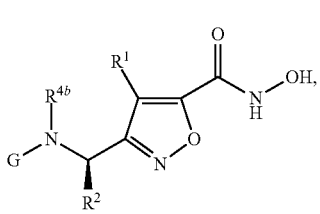
(II-a-viii)

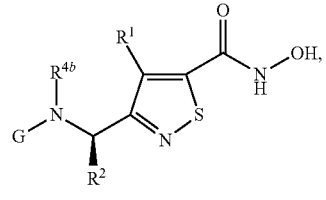
(II-a-ix)

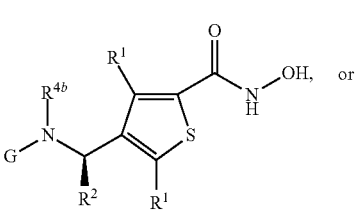
(II-a-x) or

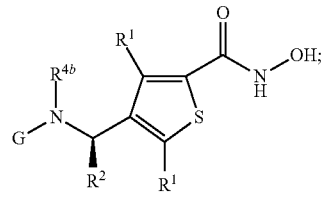
(II-a-xi)

wherein $R^1$, $R^{1a}$, $R^2$, $R^{4b}$, and G have the values described herein. In certain embodiments, the compound of formula (II-a) is represented by formulas (II-a-i) or (II-a-iii), wherein $R^1$, $R^2$, $R^{4b}$, and G have the values described herein.

In some embodiments, the compound of formula (I) is represented by formula (II-b);

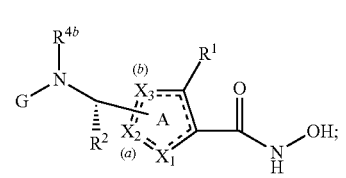
(II-b)

wherein:

ring A is a heteroaromatic 5-membered ring connected through one of positions (a) or (b);

$X_1$ is $CR^1$, O, or S;

(i) when ring A is connected through position (a), $X_2$ is C; and $X_3$ is $CR^1$, O, S, or N; or (ii) when ring A is connected through position (b), $X_3$ is C; and $X_2$ is $CR^1$, O, S, or N;

provided that only one of $X_1$, $X_2$ or $X_3$ is O or S;

and further provided that at least one of $X_1$, $X_2$, and $X_3$ is O, S, or N;

and $R^1$, $R^2$, $R^{4b}$, and G have the values described herein.

In some embodiments, the compound of formula (II-b) is represented by:

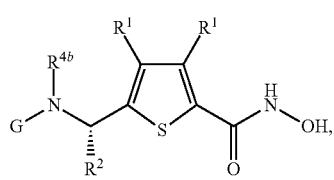
(II-b-i)

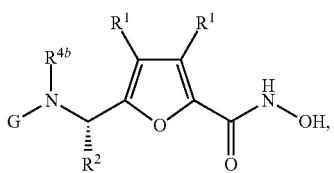
(II-b-ii)

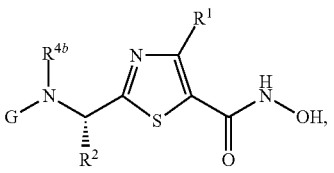
(II-b-iii)

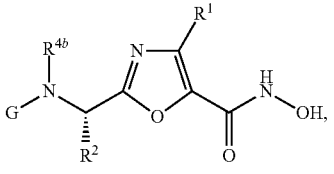
(II-b-iv)

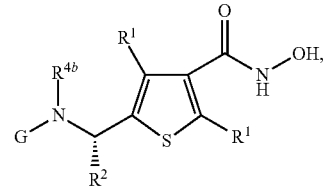
(II-b-v)

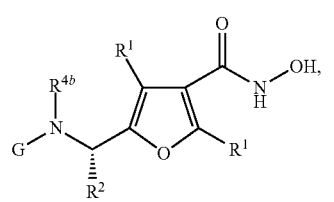
(II-b-vi)

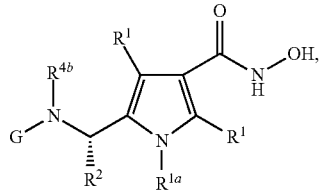
(II-b-vii)

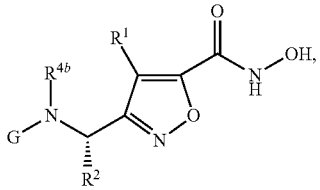
(II-b-viii)

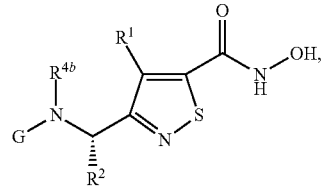
(II-b-ix)

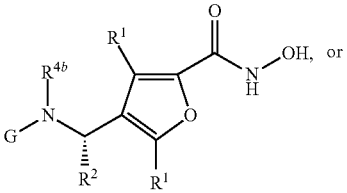
(II-b-x)

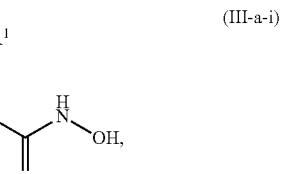
(II-b-xi)

wherein $R^1$, $R^{1a}$, $R^2$, $R^{4b}$, and G have the values described herein. In certain embodiments, the compound of formula (II-b) is represented by formulas (II-b-i) or (II-b-iii), wherein $R^1$, $R^2$, $R^{4b}$, and G have the values described herein.

In some embodiments, the compound of formula (II-a) is represented by:

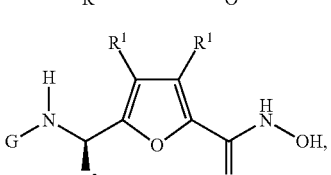
(III-a-i)

(III-a-ii)

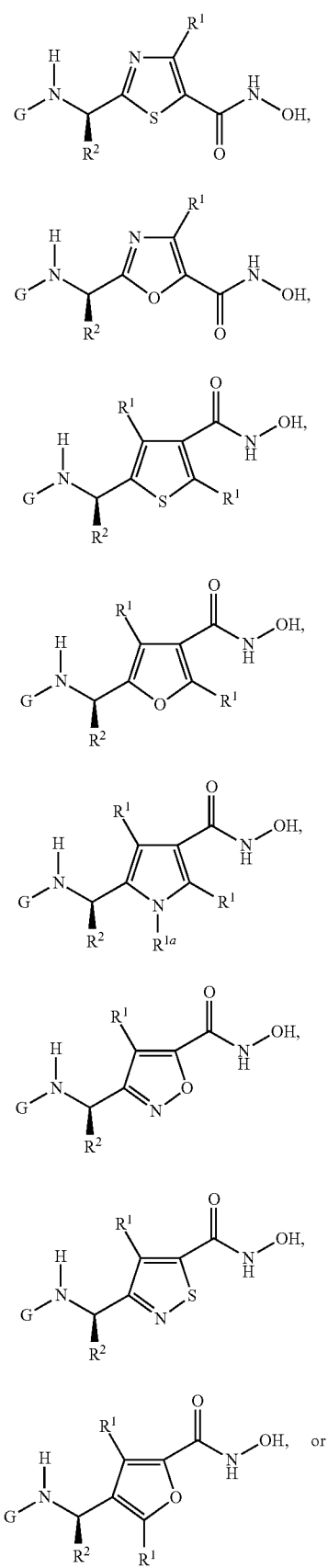
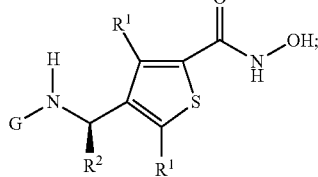

wherein $R^1$, $R^{1a}$, $R^2$, and G have the values described herein. In certain embodiments, the compound of formula (II-a) is represented by formulas (III-a-i) or (III-a-iii), wherein $R^1$, $R^2$, and G have the values described herein.

The values described below for each variable are with respect to any of formulas (I), (II) or (III) or their sub-formulas as described above.

Each occurrence of the variable $R^1$ is independently hydrogen, halogen, $C_{1-4}$ alkyl, $C_{1-3}$ fluoroalkyl, —O—$C_{1-3}$ alkyl, —O—$C_{1-3}$ fluoroalkyl, cyano, hydroxy, —NHC(O)$C_{1-3}$ alkyl, —C(O)NH$C_{1-3}$ alkyl, —NHC(O)NH$C_{1-3}$ alkyl, or —NHS(O)$_2C_{1-3}$ alkyl. In some embodiments, each occurrence of $R^1$ is independently hydrogen, chloro, fluoro, $C_{1-4}$ alkyl, —O—$C_{1-3}$ alkyl, trifluoromethyl, hydroxy, or cyano. In certain embodiments, each occurrence of $R^1$ is independently hydrogen, chloro, fluoro, hydroxy, methoxy, ethoxy, n-propoxy, isopropoxy, cyano, trifluoromethyl, methyl, ethyl, isopropyl, n-propyl, or tert-butyl. In certain embodiments, each occurrence of $R^1$ is independently hydrogen, chloro, fluoro, hydroxy, trifluoromethyl, or methyl. In certain embodiments, $R^1$ is hydrogen.

The variable $R^{1a}$ is hydrogen, or $C_{1-4}$ aliphatic. In some embodiments, $R^{1a}$ is hydrogen or methyl. In certain embodiments, $R^{1a}$ is hydrogen. In certain embodiments, $R^{1a}$ is methyl.

The variable $R^2$ is $C_{1-6}$ aliphatic, $C_{1-6}$ fluoroaliphatic, or unsubstituted or substituted 6-10-membered aryl. In some embodiments, $R^2$ is methyl, ethyl, isopropyl, n-propyl, n-butyl, isobutyl, sec-butyl, tert-butyl, pentyl, hexyl, cyclopropyl, cyclobutyl, cyclopentyl, cyclohexyl, trifluoromethyl, or phenyl. In certain embodiments, $R^2$ is methyl, ethyl, isopropyl, n-propyl, trifluoromethyl, tert-butyl, cyclopropyl, or phenyl. In certain embodiments, $R^2$ is methyl, ethyl, isopropyl, or n-propyl.

The variable $R^{4b}$ is hydrogen, or $C_{1-4}$ aliphatic. In some embodiments, $R^{4b}$ is hydrogen.

The variable G is —$R^3$, —$V_1$—$R^3$, —$V_1$-$L_1$-$R^3$, -$L_2$-$V_1$—$R^3$, -$L_2$-$V_2$—$R^3$, or -$L_1$-$R^3$, wherein $L_1$, $L_2$, $V_1$, $V_2$, and $R^3$ have the values described herein. In some embodiments, G is —$V_1$—$R^3$, or —$V_1$-$L_1$-$R^3$, wherein $L_1$, $V_1$, and $R^3$ have the values described herein. In certain embodiments, G is —$V_1$—$R^3$, wherein $V_1$, and $R^3$ have the values described herein.

The variable $L_1$ is an unsubstituted or substituted $C_{1-3}$ alkylene chain. In some embodiments, $L_1$ is —$CH_2$—, —$CH_2CH_2$—, or —$CH_2CH_2CH_2$—. In certain embodiments, $L_1$ is —$CH_2$—.

The variable $L_2$ is an unsubstituted or substituted $C_{2-3}$ alkylene chain. In some embodiments, $L_2$ is —$CH_2CH_2$— or —$CH_2CH_2CH_2$—.

The variable $V_1$ is —C(O)—, —C(O)—$CR^A$=$CR^A$—, —C(O)—N($R^{4a}$)—, —C(O)—O—, or —S(O)$_2$—, wherein $R^A$ and $R^{4a}$ have the values described herein. In some embodiments, $V_1$ is —C(O)—, —C(O)—N($R^{4a}$)—, or —S(O)$_2$—, wherein $R^{4a}$ has the values described herein. In certain embodiments, $V_1$ is —C(O)—, —C(O)—NH—, or —S(O)$_2$—. In other certain embodiments, $V_1$ is —C(O)—.

Each occurrence of the variable $R^A$ is independently hydrogen, halo, or an optionally substituted $C_{1-4}$ aliphatic group. In some embodiments, each occurrence of $R^A$ is independently hydrogen, fluoro, or methyl. In certain embodiments, each occurrence of $R^A$ is hydrogen.

Each occurrence of the variable $R^{4a}$ is independently hydrogen, or unsubstituted or substituted $C_{1-4}$ aliphatic. In certain embodiments, $R^{4a}$ is hydrogen.

The variable $V_2$ is —C(S)—, —N($R^{4a}$)—, —N($R^{4a}$)—C(O)—, —SO$_2$—N($R^{4a}$)—, —N($R^{4a}$)—SO$_2$—, —O—, —S—, —S(O)—, —N($R^{4a}$)—C(O)—N($R^{4a}$)—, —N($R^{4a}$)—C(O)—O—, —O—C(O)—N($R^{4a}$)—, or —N($R^{4a}$)—SO$_2$—N($R^{4a}$)—, wherein $R^{4a}$ has the values described herein. In some embodiments, $V_2$ is —N($R^{4a}$)—, —NR$^{4a}$—C(O)—, —SO$_2$—N($R^{4a}$)—, —N($R^{4a}$)—SO$_2$—, —O—, or —S—, wherein $R^{4a}$ has the values described herein. In certain embodiments, $V_2$ is —N($R^{4a}$)—, —O—, or —S—, wherein $R^{4a}$ has the values described herein. In certain embodiments, $V_2$ is —NH—; or —O—.

The variable $R^3$ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur.

In some embodiments, $R^3$ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; wherein
each substitutable carbon chain atom in $R^3$ is unsubstituted or substituted with 1-2 occurrences of —$R^{5dd}$;
each substitutable saturated ring carbon atom in $R^3$ is unsubstituted or substituted with =O, =S, =C($R^5$)$_2$, =N—N($R^4$)$_2$, =N—OR$^5$, =N—NHC(O)R$^5$, =N—NHCO$_2$R$^6$, =N—NHSO$_2$R$^6$, =N—R$^5$ or —$R^{5a}$;
each substitutable unsaturated ring carbon atom in $R^3$ is unsubstituted or is substituted with —$R^{5a}$;
each substitutable ring nitrogen atom in $R^3$ is unsubstituted or substituted with —$R^{9b}$;
wherein $R^{5dd}$, $R^4$, $R^5$, $R^6$, $R^{5a}$, and $R^{9b}$ have the values described herein.

In some embodiments, $R^3$ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; wherein
each substitutable carbon chain atom in $R^3$ is unsubstituted or substituted with 1-2 occurrences of —$R^{5dd}$;
each substitutable saturated ring carbon atom in $R^3$ is unsubstituted or substituted with =O, =S, =C($R^5$)$_2$, =N—R$^5$ or —$R^{5a}$;
each substitutable unsaturated ring carbon atom in $R^3$ is unsubstituted or is substituted with —$R^{5a}$;
each substitutable ring nitrogen atom in $R^3$ is unsubstituted or substituted with —$R^{9b}$;
wherein $R^{5dd}$, $R^5$, $R^{5a}$, and $R^{9b}$ have the values described herein.

In certain embodiments, $R^3$ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; wherein:
each substitutable carbon chain atom in $R^3$ is unsubstituted or substituted with 1-2 occurrences of —$R^{5dd}$;
each substitutable saturated ring carbon atom in $R^3$ is unsubstituted or substituted with —$R^{5a}$;
each substitutable unsaturated ring carbon atom in $R^3$ is unsubstituted or is substituted with —$R^{5a}$;
the total number of $R^{5a}$ substituents is p;
each substitutable ring nitrogen atom in $R^3$ is unsubstituted or substituted with —$R^{9b}$;
wherein $R^{5dd}$, $R^{5a}$, $R^{9b}$, and p have the values described herein.

In some embodiments, $R^3$ is unsubstituted or substituted $C_{1-6}$ aliphatic. In certain embodiments, each substitutable carbon chain atom in $R^3$ is unsubstituted or substituted with 1-2 occurrences of —$R^{5dd}$, wherein $R^{5dd}$ has the values described herein. In certain embodiments, $R^3$ is methyl, ethyl, n-propyl, isopropyl, tert-butyl, n-butyl, iso-butyl, pentyl, hexyl, butenyl, propenyl, pentenyl, or hexenyl, wherein each of the aforementioned groups is unsubstituted or substituted. In certain embodiments, $R^3$ is methyl, ethyl, n-propyl, isopropyl, tert-butyl, n-butyl, iso-butyl, pentyl, hexyl, butenyl, propenyl, pentenyl, or hexenyl, wherein each substitutable carbon chain atom in $R^3$ is unsubstituted or substituted with 1-2 occurrences of —$R^{5dd}$, wherein $R^{5dd}$ has the values described herein.

In some embodiments, $R^3$ is unsubstituted or substituted unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur.

In certain embodiments, $R^3$ is unsubstituted or substituted unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur, wherein:
each substitutable saturated ring carbon atom in $R^3$ is unsubstituted or substituted with =O, =S, =C($R^5$)$_2$, =N—N($R^4$)$_2$, =N—OR$^5$, =N—NHC(O)R$^5$, =N—NHCO$_2$R$^6$, =N—NHSO$_2$R$^6$, =N—R$^5$ or —$R^{5a}$;
each substitutable unsaturated ring carbon atom in $R^3$ is unsubstituted or is substituted with —$R^{5a}$;
each substitutable ring nitrogen atom in $R^3$ is unsubstituted or substituted with —$R^{9b}$;
wherein $R^4$, $R^5$, $R^6$, $R^{5a}$, and $R^{9b}$ have the values described herein.

In certain embodiments, $R^3$ is unsubstituted or substituted unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur, wherein:

each substitutable saturated ring carbon atom in $R^3$ is unsubstituted or substituted with =O, =S, =C($R^5$)$_2$, =N—$R^5$ or —$R^{5a}$;

each substitutable unsaturated ring carbon atom in $R^3$ is unsubstituted or is substituted with —$R^{5a}$;

each substitutable ring nitrogen atom in $R^3$ is unsubstituted or substituted with —$R^{9b}$;

wherein $R^5$, $R^{5a}$, and $R^{9b}$ have the values described herein.

In certain embodiments, $R^3$ is unsubstituted or substituted unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur, wherein:

each substitutable saturated ring carbon atom in $R^3$ is unsubstituted or substituted with —$R^{5a}$;

each substitutable unsaturated ring carbon atom in $R^3$ is unsubstituted or is substituted with —$R^{5a}$;

the total number of $R^{5a}$ substituents is p;

each substitutable ring nitrogen atom in $R^3$ is unsubstituted or substituted with —$R^{9b}$;

wherein $R^{5a}$, $R^{9b}$, and p have the values described herein.

In certain embodiments, $R^3$ is furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, imidazopyridyl, indolyl, isoindolyl, indazolyl, benzimidazolyl, benzthiazolyl, benzothienyl, benzofuranyl, benzoxazolyl, benzodioxolyl, benzthiadiazolyl, 2,3-dihydrobenzofuranyl, 4H-furo[3,2-b]pyrrolyl, pyrazolopyrimidinyl, purinyl, quinolyl, isoquinolyl, tetrahydroquinolinyl, tetrahydroisoquinolinyl, cinnolinyl, phthalazinyl, quinazolinyl, quinoxalinyl, naphthyridinyl, pteridinyl, tetrahydrofuranyl, tetrahydropyranyl, tetrahydrothienyl, indanyl, tetrahydroindazolyl, pyrrolidinyl, pyrrolidonyl, piperidinyl, pyrrolinyl, decahydroquinolinyl, oxazolidinyl, piperazinyl, dioxanyl, diazepinyl, oxazepinyl, thiazepinyl, morpholinyl, thiamorpholinyl, quinuclidinyl, phenanthridinyl, tetrahydronaphthyl, indolinyl, benzodioxanyl, chromanyl, cyclopropyl, cyclobutyl, cyclopentyl, cyclohexyl, cycloheptyl, cyclooctyl, cyclopentenyl, cyclohexenyl, cycloheptenyl, cyclooctenyl, bicycloheptanyl, bicyclooctanyl, or adamantyl; wherein:

each substitutable saturated ring carbon atom in $R^3$ is unsubstituted or substituted with =O, =S, =C($R^5$)$_2$, =N—N($R^4$)$_2$, =N—O$R^5$, =N—NHC(O)$R^5$, =N—NHCO$_2R^6$, =N—NHSO$_2R^6$, =N—$R^5$ or —$R^{5a}$;

each substitutable unsaturated ring carbon atom in $R^3$ is unsubstituted or is substituted with —$R^{5a}$;

each substitutable ring nitrogen atom in $R^3$ is unsubstituted or substituted with —$R^{9b}$;

wherein $R^4$, $R^5$, $R^6$, $R^{5a}$, and $R^{9b}$ have the values described herein.

In certain embodiments, $R^3$ is furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, imidazopyridyl, indolyl, isoindolyl, indazolyl, benzimidazolyl, benzthiazolyl, benzothienyl, benzofuranyl, benzoxazolyl, benzodioxolyl, benzthiadiazolyl, 2,3-dihydrobenzofuranyl, 4H-furo[3,2-b]pyrrolyl, pyrazolopyrimidinyl, purinyl, quinolyl, isoquinolyl, tetrahydroquinolinyl, tetrahydroisoquinolinyl, cinnolinyl, phthalazinyl, quinazolinyl, quinoxalinyl, naphthyridinyl, pteridinyl, tetrahydrofuranyl, tetrahydropyranyl, tetrahydrothienyl, indanyl, tetrahydroindazolyl, pyrrolidinyl, pyrrolidonyl, piperidinyl, pyrrolinyl, decahydroquinolinyl, oxazolidinyl, piperazinyl, dioxanyl, diazepinyl, oxazepinyl, thiazepinyl, morpholinyl, thiamorpholinyl, quinuclidinyl, phenanthridinyl, tetrahydronaphthyl, indolinyl, benzodioxanyl, chromanyl, cyclopropyl, cyclobutyl, cyclopentyl, cyclohexyl, cycloheptyl, cyclooctyl, cyclopentenyl, cyclohexenyl, cycloheptenyl, cyclooctenyl, bicycloheptanyl, bicyclooctanyl, or adamantyl; wherein:

each substitutable saturated ring carbon atom in $R^3$ is unsubstituted or substituted with =O, =S, =C($R^5$)$_2$, =N—$R^5$ or —$R^{5a}$;

each substitutable unsaturated ring carbon atom in $R^3$ is unsubstituted or is substituted with —$R^{5a}$;

each substitutable ring nitrogen atom in $R^3$ is unsubstituted or substituted with —$R^{9b}$;

wherein $R^{5a}$ and $R^{9b}$ have the values described herein.

In certain embodiments, $R^3$ is furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, imidazopyridyl, indolyl, isoindolyl, indazolyl, benzimidazolyl, benzthiazolyl, benzothienyl, benzofuranyl, benzoxazolyl, benzodioxolyl, benzthiadiazolyl, 2,3-dihydrobenzofuranyl, 4H-furo[3,2-b]pyrrolyl, pyrazolopyrimidinyl, purinyl, quinolyl, isoquinolyl, tetrahydroquinolinyl, tetrahydroisoquinolinyl, cinnolinyl, phthalazinyl, quinazolinyl, quinoxalinyl, naphthyridinyl, pteridinyl, tetrahydrofuranyl, tetrahydropyranyl, tetrahydrothienyl, indanyl, tetrahydroindazolyl, pyrrolidinyl, pyrrolidonyl, piperidinyl, pyrrolinyl, decahydroquinolinyl, oxazolidinyl, piperazinyl, dioxanyl, diazepinyl, oxazepinyl, thiazepinyl, morpholinyl, thiamorpholinyl, quinuclidinyl, phenanthridinyl, tetrahydronaphthyl, indolinyl, benzodioxanyl, chromanyl, cyclopropyl, cyclobutyl, cyclopentyl, cyclohexyl, cycloheptyl, cyclooctyl, cyclopentenyl, cyclohexenyl, cycloheptenyl, cyclooctenyl, bicycloheptanyl, bicyclooctanyl, or adamantyl; wherein:

each substitutable saturated ring carbon atom in $R^3$ is unsubstituted or substituted with —$R^{5a}$;

each substitutable unsaturated ring carbon atom in $R^3$ is unsubstituted or is substituted with —$R^{5a}$;

the total number of $R^{5a}$ substituents is p;

each substitutable ring nitrogen atom in $R^3$ is unsubstituted or substituted with —$R^{9b}$;

wherein $R^{5a}$, $R^{9b}$, and p have the values described herein.

In some embodiments, each occurrence of $R^{5dd}$ is independently halogen, hydroxy, —O($C_{1-3}$ alkyl), cyano, —N($R^4$)$_2$, —C(O)($C_{1-3}$ alkyl), —CO$_2$H, —CO$_2$($C_{1-3}$ alkyl), —C(O)NH$_2$, or —C(O)NH($C_{1-3}$ alkyl). In certain embodiments, each occurrence of $R^{5dd}$ is independently fluoro, hydroxy, methoxy, ethoxy, or —C(O)NHCH$_3$.

Each $R^4$ is independently hydrogen, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two $R^4$ on the same nitrogen atom, taken together with the nitrogen atom, form an unsubstituted or substituted 5- to 6-membered heteroaryl or an unsubstituted or substituted 4- to 8-membered heterocyclyl having, in addition to the nitrogen atom, 0-2 ring heteroatoms selected from nitrogen, oxygen, and sulfur.

Each $R^5$ is independently hydrogen, unsubstituted or substituted $C_{1-6}$ aliphatic, unsubstituted or substituted 3-10- membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur.

Each $R^6$ is independently unsubstituted or substituted $C_{1-6}$ aliphatic, or unsubstituted or substituted 6-10-membered aryl.

Each $R^7$ is independently unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur.

Each $R^{9b}$ is independently —C(O)$R^5$, —C(O)N($R^4$)$_2$, —CO$_2R^6$, —SO$_2R^6$, —SO$_2$N($R^4$)$_2$, unsubstituted $C_{1-4}$ aliphatic, or $C_{1-4}$ aliphatic substituted with 1-2 independent occurrences of $R^7$ or $R^8$, wherein $R^7$ and $R^8$ have the values described herein.

Each $R^8$ is independently halogen, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, or —C(O)NH($C_{1-3}$ alkyl), wherein $R^4$ has the values described herein.

Each $R^{5a}$ is independently halogen, —NO$_2$, —CN, —C($R^5$)=C($R^5$)$_2$, —C≡C—$R^5$, —O$R^5$, —S$R^5$, —S(O)$R^6$, —SO$_2R^6$, —SO$_2$N($R^4$)$_2$, —N($R^4$)$_2$, —NR$^4$C(O)$R^5$, —NR$^4$C(O)N($R^4$)$_2$, —NR$^4$CO$_2R^6$, —OC(O)N($R^4$)$_2$, —C(O)—C(O)$R^5$, —C(O)$R^5$, —C(O)N($R^4$)$_2$, —C(=NR$^4$)—N($R^4$)$_2$, —C(=NR$^4$)—O$R^5$, —N($R^4$)—N($R^4$)$_2$, —N($R^4$)C(=NR$^4$)—N($R^4$)$_2$, —N($R^4$)SO$_2R^6$, —N($R^4$)SO$_2$N($R^4$)$_2$, —P(O)($R^5$)$_2$, —P(O)(O$R^5$)$_2$, unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two adjacent $R^{5a}$, taken together with the intervening ring atoms, form an unsubstituted or substituted fused aromatic ring or an unsubstituted or substituted non-aromatic ring having 0-3 heteroatoms independently selected from nitrogen, oxygen, and sulfur, wherein $R^5$, $R^6$, and $R^4$ have the values described herein.

In some embodiments, each $R^{5a}$ is independently halogen, —CN, —OH, $C_{1-4}$ alkyl, $C_{1-3}$ fluoroalkyl, —O—$C_{1-3}$ alkyl, —O—$C_{1-3}$ fluoroalkyl, —NHC(O)$C_{1-3}$ alkyl, —C(O)NHC$_{1-3}$ alkyl, —NHC(O)NHC$_{1-3}$ alkyl, —NHS(O)$_2$C$_{1-3}$ alkyl, 3-10-membered cycloaliphatic substituted with 0-2 occurrences of —$R^{7a}$, 4-10-membered heterocyclyl having 1-5 heteroatoms independently selected from nitrogen, oxygen, and sulfur substituted with 0-2 occurrences of —$R^{7a}$, 6-10-membered aryl substituted with 0-2 occurrences of —$R^{7a}$, or 5-10-membered heteroaryl having 1-5 heteroatoms independently selected from nitrogen, oxygen, and sulfur substituted with 0-2 occurrences of —$R^{7a}$ wherein $R^{7a}$ has the values described herein.

In certain embodiments, each $R^{5a}$ is independently chloro, fluoro, hydroxy, methoxy, ethoxy, n-propoxy, isopropoxy, cyano, trifluoromethyl, methyl, ethyl, isopropyl, n-propyl, tert-butyl or phenyl.

Each occurrence of the variable $R^{7a}$ is independently halogen, $C_{1-3}$ alkyl, $C_{1-3}$ fluoroalkyl, —O—$C_{1-3}$ alkyl, —O—$C_{1-3}$ fluoroalkyl, —NHC(O)$C_{1-3}$ alkyl, —C(O)NHC$_{1-3}$ alkyl, —NHC(O)NHC$_{1-3}$ alkyl, or —NHS(O)$_2$C$_{1-3}$ alkyl.

The variable p is 1-2. In some embodiments, p is 1.

In some embodiments, G is:

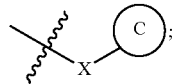

wherein X and Ring C have the values described herein.

In certain embodiments, G is:

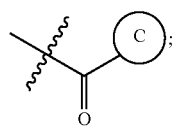

wherein Ring C has the values described herein.

The variable X is —C(O)— or -$L_{2a}$-$R^{3aa}$—$V_{2a}$—, wherein $L_{2a}$, $R^{3aa}$, and $V_{2a}$ have the values described herein. In some embodiments, X is —C(O)—. In some embodiments, X is -$L_{2a}$-$R^{3aa}$—$V_{2a}$—, wherein $L_{2a}$, $R^{3aa}$, and $V_{2a}$ have the values described herein. In some embodiments, X is —C(O)—,

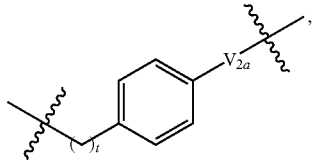
X-a

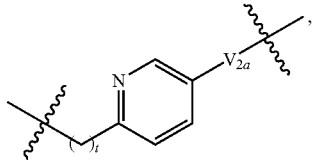
X-b

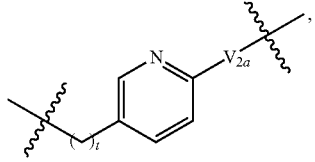
X-c

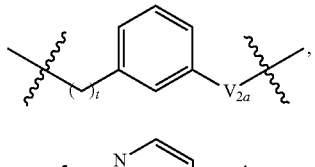
X-d

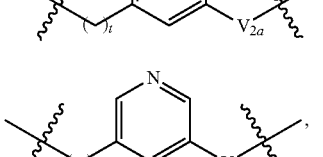
X-e

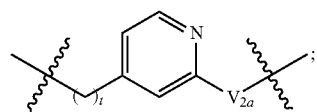
wherein V$_{2a}$ and t have the values described herein.
In certain embodiments, X is —C(O)—,
X-i
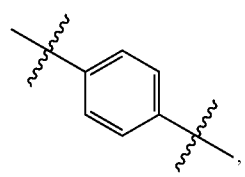
X-ii
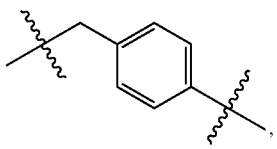
X-iii
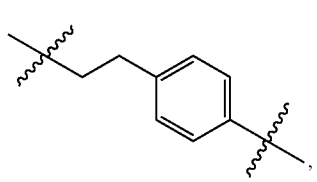
X-iv
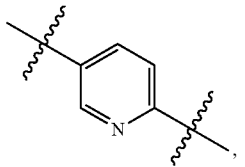
X-v
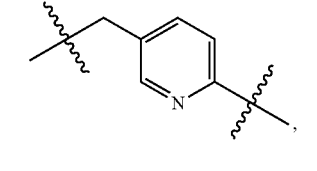
X-vi
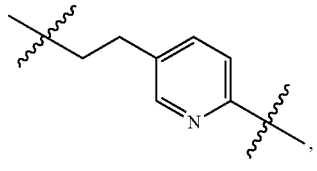
X-vii
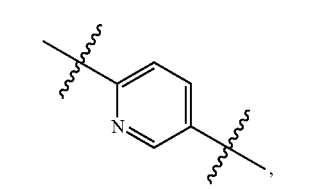
X-viii
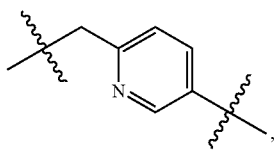
X-ix
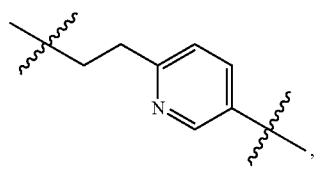
X-x
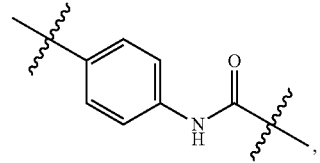
X-xi
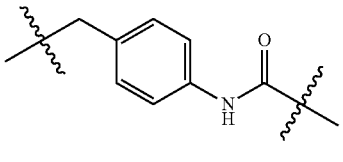
X-xii
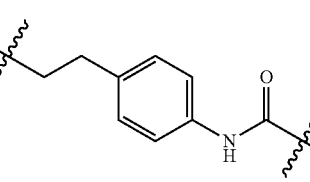
X-xiii
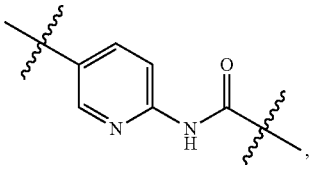
X-xiv
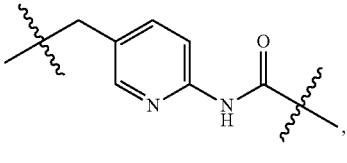
X-xv
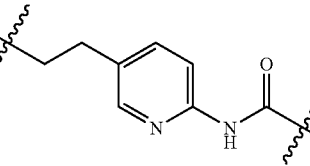
X-xvi
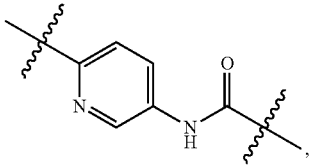

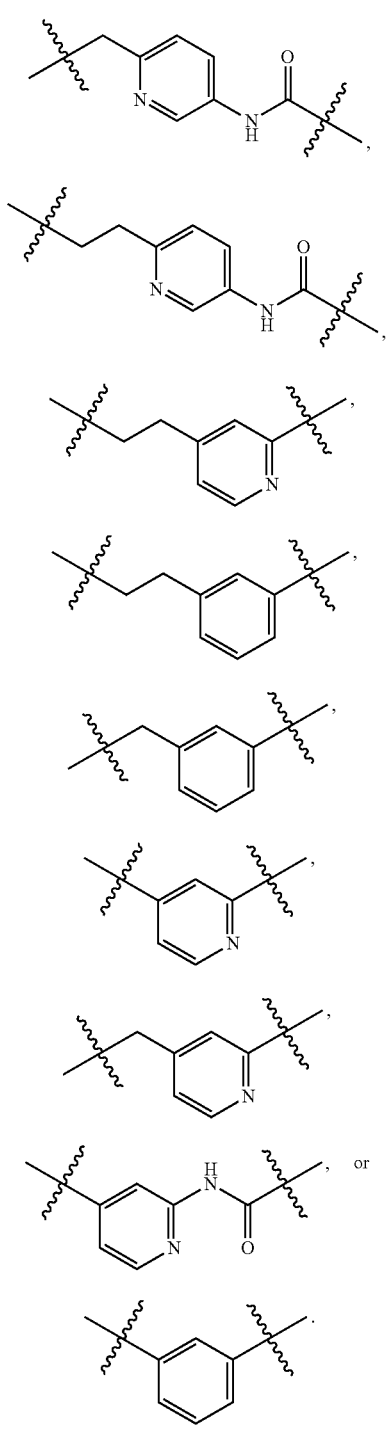

In certain embodiments, X is —C(O)—, X-ii, X-iii, X-xi, X-xii, X-xxii, X-xxiv, or X-xxv.

Ring C is a 4-7 membered heterocyclic ring containing one nitrogen atom, wherein the nitrogen atom is not the atom bound to X, and wherein the nitrogen atom in Ring C is substituted with $R^{9bb}$ and Ring C is unsubstituted or substituted by 1-4 occurrences of $R^{5b}$; wherein $R^{9bb}$, X, and $R^{5b}$ have the values described herein. In some embodiments, Ring C is a 4-7 membered heterocyclic ring containing one nitrogen atom, wherein the nitrogen atom is not the atom bound to X, and wherein the nitrogen atom in Ring C is substituted with $R^{9bb}$ and Ring C is unsubstituted or substituted by 1-2 occurrences of $R^{5b}$; wherein $R^{9bb}$, X, and $R^{5b}$ have the values described herein.

In certain embodiments, Ring C is:

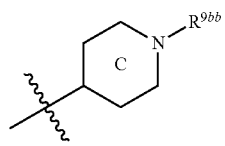

wherein Ring C is unsubstituted or substituted with 1 occurrence of $R^{5b}$, wherein $R^{9bb}$ and $R^{5b}$ have the values described herein. In certain embodiments, Ring C is:

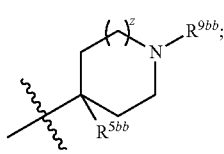

wherein $R^{9bb}$, z and $R^{5bb}$ have the values described herein.

The variable $V_{2a}$ is a bond, —NH—C(O)—, —NH—S(O)$_2$—, or —NH—C(O)—NH—. In some embodiments, $V_{2a}$ is a bond or —NH—C(O)—. In certain embodiments, $V_{2a}$ is a bond. In certain embodiments, $V_{2a}$ is —NH—C(O)—.

The variable t is 0-2. In some embodiments, t is 0-1. In certain embodiments, t is 0. In certain embodiments, t is 1. In certain embodiments, t is 2.

The variable $L_{2a}$ is a bond or unsubstituted or substituted $C_{1-3}$ alkylene chain. In some embodiments, $L_{2a}$ is a bond, —CH$_2$—, —CH$_2$CH$_2$—, or —CH$_2$CH$_2$CH$_2$—. In certain embodiments, $L_{2a}$ is a bond. In certain embodiments, $L_{2a}$ is —CH$_2$—. In certain embodiments, $L_{2a}$ is —CH$_2$CH$_2$—.

The variable $R^{3aa}$ is a 6-membered aromatic ring containing 0-2 nitrogen atoms which is unsubstituted or substituted with 1-2 independent occurrences of $R^{4c}$, wherein $R^{4c}$ has the values described herein. In some embodiments, $R^{3aa}$ is phenyl or pyridyl, each of which is unsubstituted or substituted with 1-2 independent occurrences of $R^{4c}$, wherein $R^{4c}$ has the values described herein. In some embodiments, $R^{3aa}$ is:

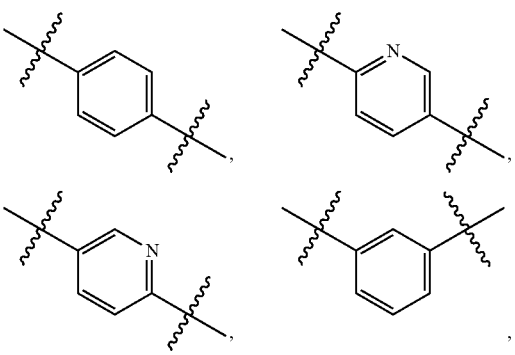

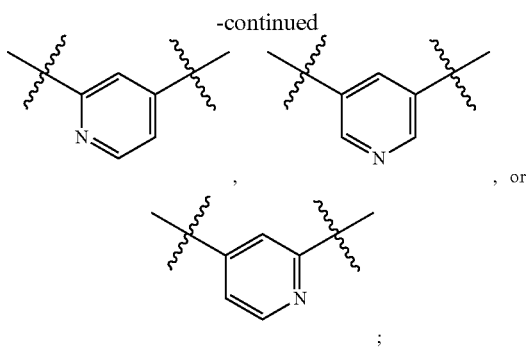

, or wherein each ring is unsubstituted or substituted with 1-2 independent occurrences of $R^{4c}$.

The variable $R^{4c}$ is chloro, fluoro, cyano, hydroxy, methoxy, ethoxy, trifluoromethoxy, trifluoromethyl, methyl, or ethyl. In some embodiments, $R^{4c}$ is chloro, fluoro, methyl or ethyl.

The variable z is 0-1. In some embodiments, z is 0. In some embodiments, z is 1.

Each occurrence of the variable $R^{5b}$ is independently chloro, fluoro, hydroxy, methyl, ethyl, methoxy, ethoxy, trifluoromethyl, trifluoromethoxy, —C(O)NH$_2$, or —CO$_2$H. In some embodiments, each occurrence of the variable $R^{5b}$ is independently chloro, fluoro, hydroxy, methyl, or ethyl. In certain embodiments, each occurrence of the variable $R^{5b}$ is methyl.

The variable $R^{5bb}$ is hydrogen or methyl. In some embodiments, $R^{5bb}$ is hydrogen. In some embodiments, $R^{5bb}$ is methyl.

The variable $R^{9bb}$ is hydrogen, unsubstituted C(O)—O—C$_{1-6}$ aliphatic, unsubstituted C(O)—C$_{1-6}$ aliphatic, unsubstituted C(O)—C$_{3-10}$ cycloaliphatic, or unsubstituted C$_{1-6}$ aliphatic. In some embodiments, $R^{9bb}$ is hydrogen, methyl, ethyl, isopropyl, or tert-butoxycarbonyl. In some embodiments, $R^{9bb}$ is methyl, ethyl, or isopropyl. In certain embodiments, $R^{9bb}$ is hydrogen.

In certain embodiments, the compound of formula (I) is represented by:

(III-a-i)

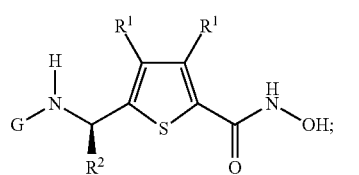

wherein:

each occurrence of $R^1$ is independently hydrogen, chloro, fluoro, hydroxy, trifluoromethyl, or methyl;

G is —V$_1$—R$^3$; and

V$_1$ is —C(O)—, —C(O)—N(R$^{4a}$)— or —S(O)$_2$—;

wherein R$^2$, R$^3$, and R$^{4a}$ have the values described herein.

In certain embodiments, the compound of formula (I) is represented by:

(III-a-iii)

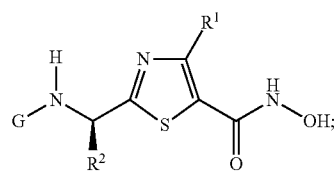

wherein:

$R^1$ is hydrogen, chloro, fluoro, hydroxy, trifluoromethyl, or methyl;

G is —V$_1$—R$^3$; and

V$_1$ is —C(O)—, —C(O)—N(R$^{4a}$)— or —S(O)$_2$—;

wherein R$^2$, R$^3$, and R$^{4a}$ have the values described herein.

In certain embodiments, the compound of formula (I) is represented by:

(IV)

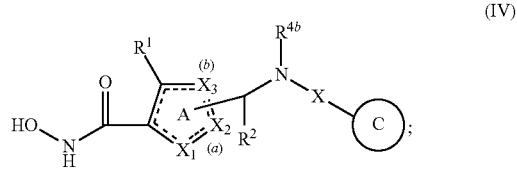

wherein:

ring A is a heteroaromatic 5-membered ring connected through one of positions (a) or (b);

$X_1$ is CR$^1$, O, or S;
  (i) when ring A is connected through position (a), $X_2$ is C; and $X_3$ is CR$^1$, O, S, or N; or
  (ii) when ring A is connected through position (b), $X_3$ is C; and $X_2$ is CR$^1$, O, S, or N;

provided that only one of $X_1$, $X_2$, or $X_3$ is O or S;

and further provided that at least one of $X_1$, $X_2$, and $X_3$ is O, S, or N;

$R^{4b}$ is hydrogen, or C$_{1-4}$ aliphatic;

$R^2$ is methyl, ethyl, isopropyl, n-propyl, trifluoromethyl, tert-butyl, cyclopropyl, or phenyl;

$R^1$ is hydrogen, chloro, fluoro, hydroxy, methoxy, ethoxy, n-propoxy, isopropoxy, cyano, trifluoromethyl, methyl, ethyl, isopropyl, n-propyl, or tert-butyl; and wherein Ring C and X have the values described herein.

In such embodiments:

$R^2$ is methyl, ethyl, isopropyl, or n-propyl;

$R^1$ is hydrogen; and $R^{4b}$ is hydrogen.

In certain embodiments, the compound of formula (I) is represented by:

(V)

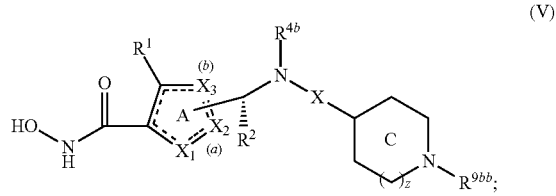

wherein:

ring A is a heteroaromatic 5-membered ring connected through one of positions (a) or (b);

$X_1$ is $CR^1$, O, or S;

(i) when ring A is connected through position (a), $X_2$ is C; and $X_3$ is $CR^1$, O, S, or N; or (ii) when ring A is connected through position (b), $X_3$ is C; and $X_2$ is $CR^1$, O, S, or N;

provided that only one of $X_1$, $X_2$, or $X_3$ is O or S;

and further provided that at least one of $X_1$, $X_2$, and $X_3$ is O, S, or N;

$R^{4b}$ is hydrogen;

$R^2$ is methyl, ethyl, isopropyl, n-propyl, trifluoromethyl, tert-butyl, cyclopropyl, or phenyl;

each occurrence of $R^1$ is independently hydrogen, chloro, fluoro, hydroxy, trifluoromethyl, or methyl;

$R^{9bb}$ is hydrogen, methyl, ethyl, isopropyl, or tert-butoxycarbonyl;

X is —C(O)—, X-a, X-b, X-c, X-d, X-e, X-f, or X-g;

Ring C is unsubstituted or substituted with one occurrence of $R^{5b}$; and z, $R^{5b}$, t, and $V_{2a}$ have the values described herein.

In such embodiments:

$R^2$ is methyl, ethyl, isopropyl, or n-propyl;

$R^1$ is hydrogen; and $R^{5b}$ is methyl.

In certain embodiments, the compound of formula (I) is represented by:

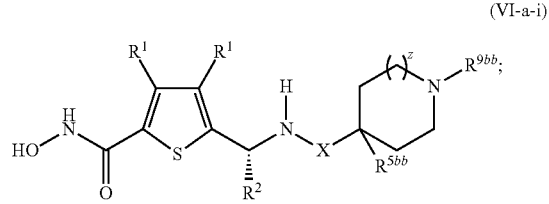

(VI-a-i)

wherein:

each occurrence of $R^1$ is independently hydrogen, chloro, fluoro, hydroxy, trifluoromethyl, or methyl;

$R^2$ is methyl, ethyl, isopropyl, n-propyl, trifluoromethyl, tert-butyl, cyclopropyl, or phenyl;

$R^{9bb}$ is hydrogen, methyl, ethyl, isopropyl, or tert-butoxycarbonyl;

X is —C(O)—, X-ii, X-iii, X-xi, X-xii, X-xxii, X-xxiv, or X-xxv;

$R^{5bb}$ is hydrogen or methyl; and z has the values described herein.

In certain such embodiments, $R^1$ is hydrogen;

$R^2$ is methyl, ethyl, isopropyl, or n-propyl;

$R^{5bb}$ is methyl; and z is 1.

In certain embodiments, the compound of formula (I) is represented by:

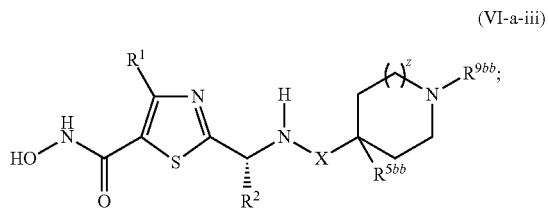

(VI-a-iii)

wherein:

each occurrence of $R^1$ is independently hydrogen, chloro, fluoro, hydroxy, trifluoromethyl, or methyl;

$R^2$ is methyl, ethyl, isopropyl, n-propyl, trifluoromethyl, tert-butyl, cyclopropyl, or phenyl;

$R^{9bb}$ is hydrogen, methyl, ethyl, isopropyl, or tert-butoxycarbonyl;

X is —C(O)—, X-ii, X-iii, X-xi, X-xii, X-xxii, X-xxiv, or X-xxv;

$R^{5bb}$ is hydrogen or methyl; and z has the values described herein.

In certain such embodiments, $R^1$ is hydrogen;

$R^2$ is methyl, ethyl, isopropyl, or n-propyl;

$R^{5bb}$ is methyl; and z is 1.

In certain embodiments, the compound of formula (I) is represented by:

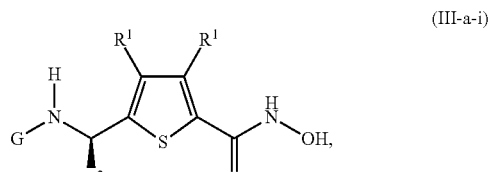

(III-a-i)

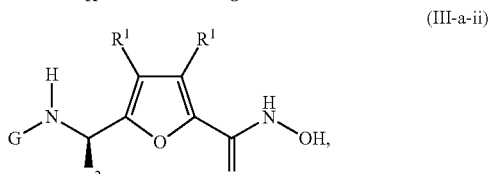

(III-a-ii)

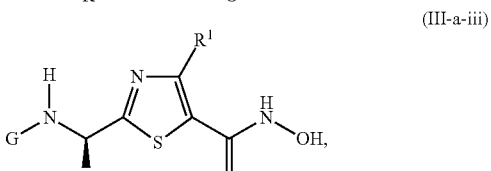

(III-a-iii)

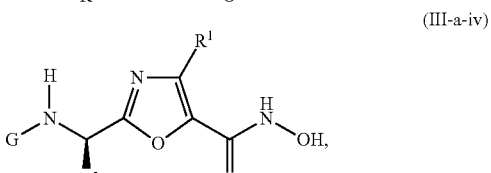

(III-a-iv)

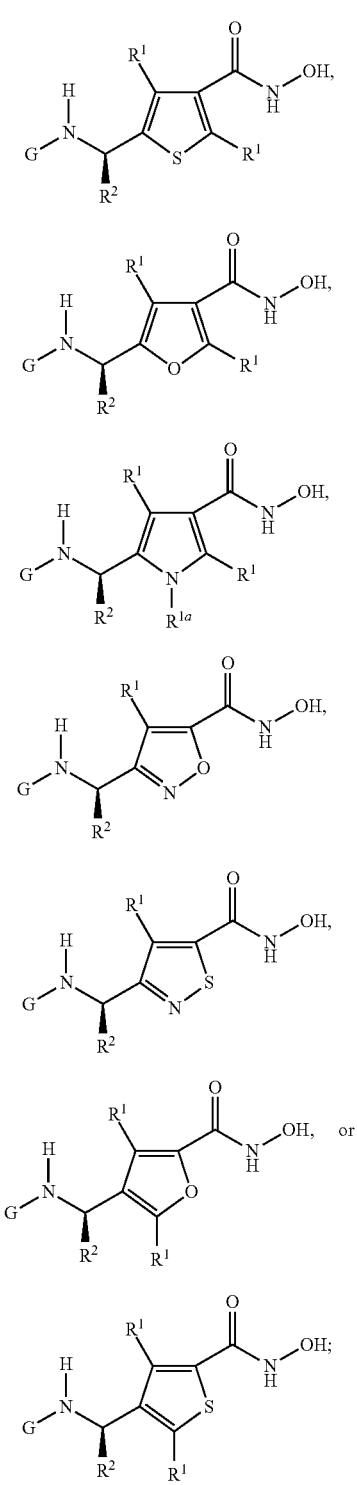

wherein
each occurrence of $R^1$ is independently hydrogen, chloro, fluoro, hydroxy, trifluoromethyl, or methyl;
G is —$V_1$—$R^3$;
$V_1$ is —C(O)—, —C(O)—N($R^{4a}$)— or —S(O)$_2$—;
$R^2$ is methyl, ethyl, isopropyl, or n-propyl; and
$R^3$ and $R^{1a}$ have the values described herein.

In certain such embodiments, the compound of formula (I) is represented by formula (III-a-i). In certain such embodiments, the compound of formula (I) is represented by formula (III-a-ii). In certain such embodiments, the compound of formula (I) is represented by formula (III-a-iii). In certain such embodiments, the compound of formula (I) is represented by formula (III-a-iv). In certain such embodiments, the compound of formula (I) is represented by formula (III-a-v). In certain such embodiments, the compound of formula (I) is represented by formula (III-a-vi). In certain such embodiments, the compound of formula (I) is represented by formula (III-a-vii). In certain such embodiments, the compound of formula (I) is represented by formula (III-a-viii). In certain such embodiments, the compound of formula (I) is represented by formula (III-a-ix). In certain such embodiments, the compound of formula (I) is represented by formula (III-a-x). In certain such embodiments, the compound of formula (I) is represented by formula (III-a-xi).

In certain such embodiments, the compound of formula (I) is represented by formula (III-a-i), wherein $R^1$ is hydrogen. In certain such embodiments, the compound of formula (I) is represented by formula (III-a-ii), wherein $R^1$ is hydrogen. In certain such embodiments, the compound of formula (I) is represented by formula (III-a-iii), wherein $R^1$ is hydrogen. In certain such embodiments, the compound of formula (I) is represented by formula (III-a-iv), wherein $R^1$ is hydrogen. In certain such embodiments, the compound of formula (I) is represented by formula (III-a-v), wherein $R^1$ is hydrogen. In certain such embodiments, the compound of formula (I) is represented by formula (III-a-vi), wherein $R^1$ is hydrogen. In certain such embodiments, the compound of formula (I) is represented by formula (III-a-vii), wherein $R^1$ is hydrogen. In certain such embodiments, the compound of formula (I) is represented by formula (III-a-viii), wherein $R^1$ is hydrogen. In certain such embodiments, the compound of formula (I) is represented by formula (III-a-ix), wherein $R^1$ is hydrogen. In certain such embodiments, the compound of formula (I) is represented by formula (III-a-x), wherein $R^1$ is hydrogen. In certain such embodiments, the compound of formula (I) is represented by formula (III-a-xi), wherein $R^1$ is hydrogen.

Representative examples of compounds of formula (I) are shown in Table 1:

TABLE 1

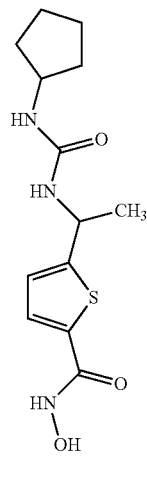 [SMILES: CC(NC(=O)NC1CCCC1)c1ccc(C(=O)NO)s1]

I-1

TABLE 1-continued
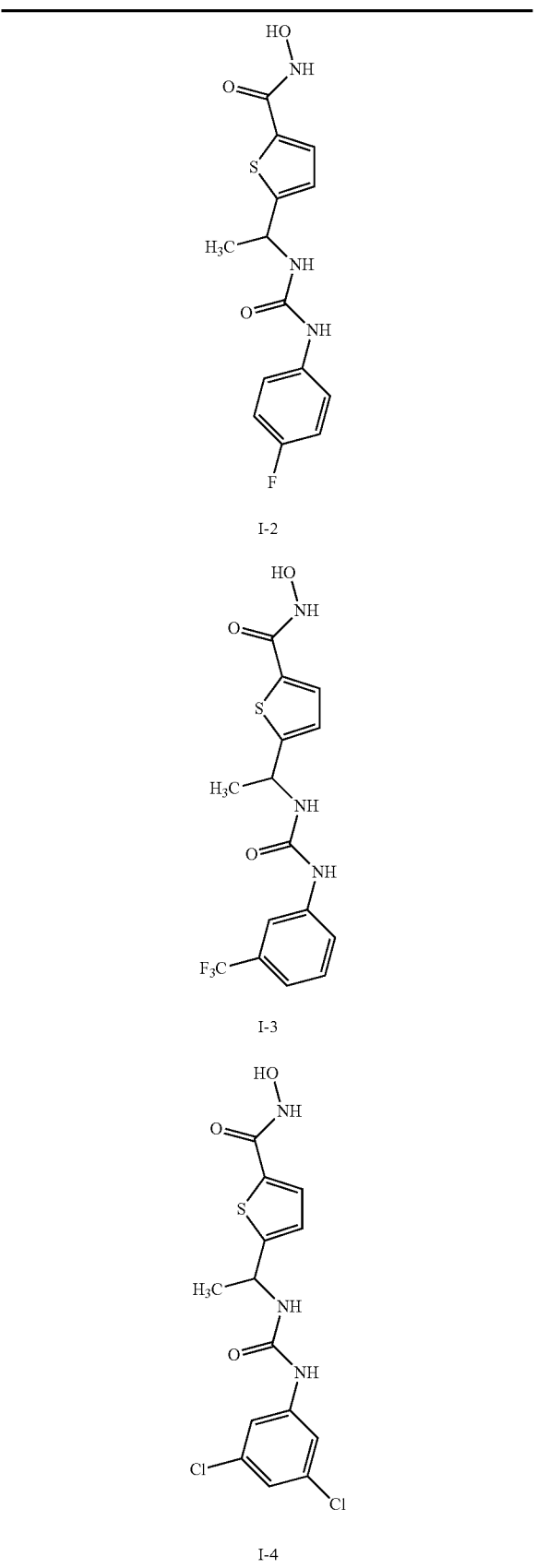
I-2
I-3
I-4
TABLE 1-continued
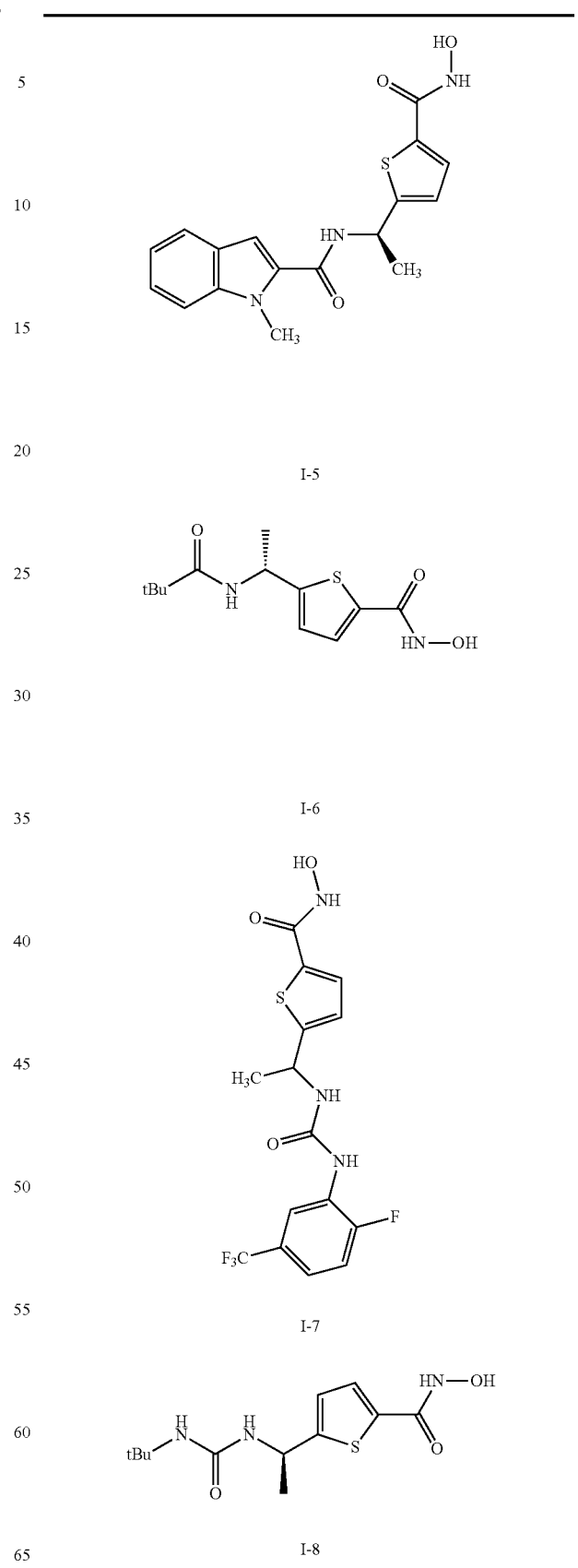
I-5
I-6
I-7
I-8

TABLE 1-continued
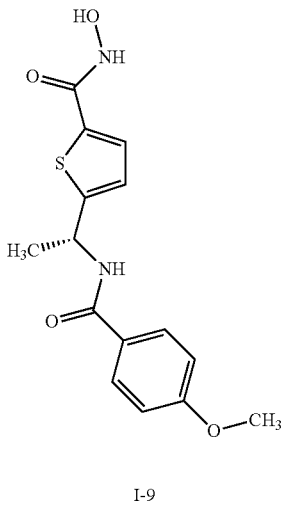
I-9
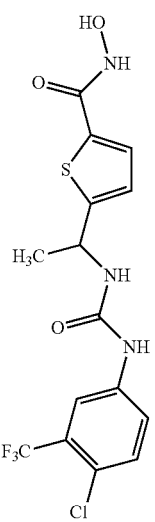
I-10
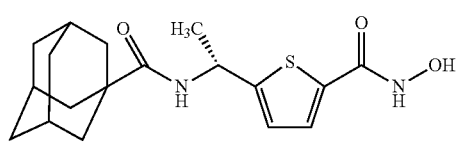 [SMILES: C[C@@H](NC(=O)C12CC3CC(CC(C3)C1)C2)c1ccc(C(=O)NO)s1]
I-11
TABLE 1-continued
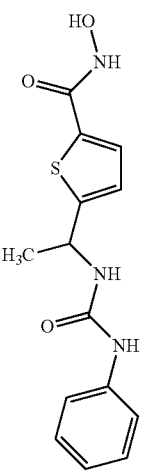 [SMILES: CC(NC(=O)Nc1ccccc1)c1ccc(C(=O)NO)s1]
I-12
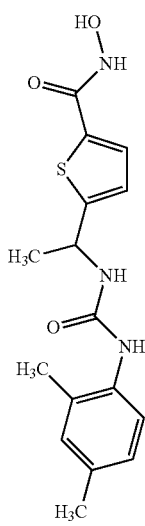
I-13

TABLE 1-continued
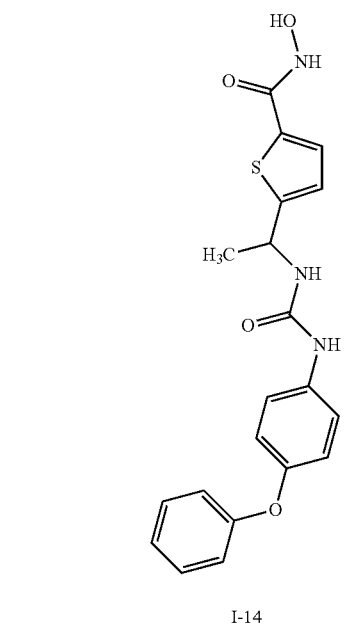
I-14
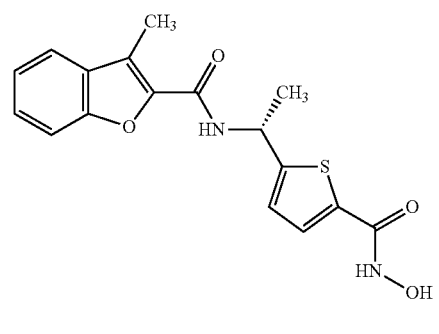 [SMILES: Cc1c(C(=O)N[C@H](C)c2ccc(C(=O)NO)s2)oc2ccccc12]
I-15
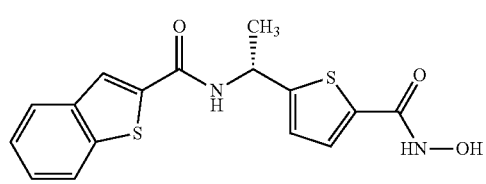
I-16
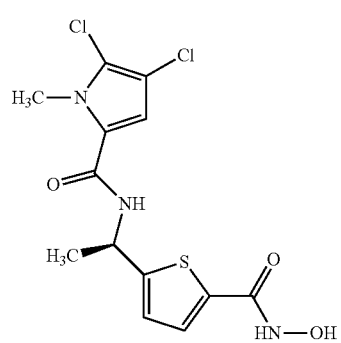 [SMILES: C[C@@H](NC(=O)c1cc(Cl)c(Cl)n1C)c1ccc(C(=O)NO)s1]
I-17
TABLE 1-continued
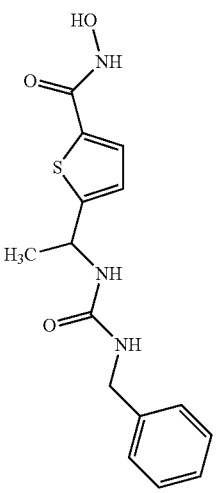 [SMILES: CC(NC(=O)NCc1ccccc1)c1ccc(C(=O)NO)s1]
I-18
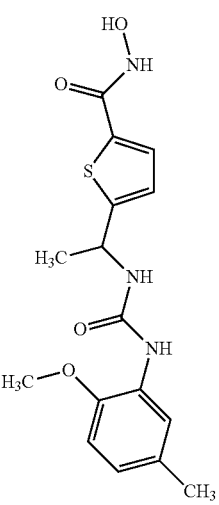
I-19
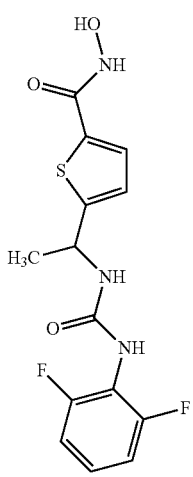 [SMILES: CC(NC(=O)Nc1c(F)cccc1F)c1ccc(C(=O)NO)s1]
I-20

TABLE 1-continued
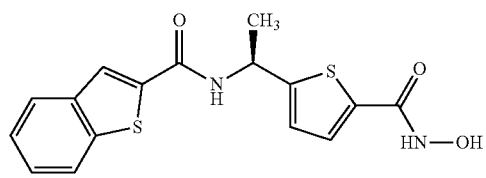 [SMILES: C[C@H](NC(=O)c1cc2ccccc2s1)c1ccc(C(=O)NO)s1]
I-21
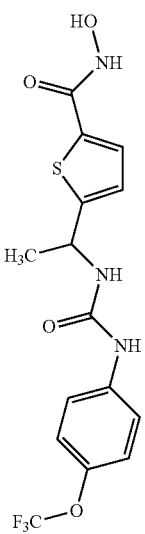 [SMILES: CC(NC(=O)Nc1ccc(OC(F)(F)F)cc1)c1ccc(C(=O)NO)s1]
I-22
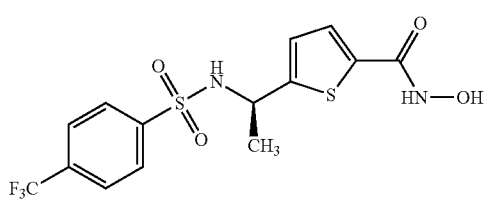 [SMILES: C[C@@H](NS(=O)(=O)c1ccc(C(F)(F)F)cc1)c1ccc(C(=O)NO)s1]
I-23
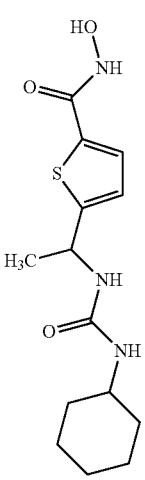 [SMILES: CC(NC(=O)NC1CCCCC1)c1ccc(C(=O)NO)s1]
I-24
TABLE 1-continued
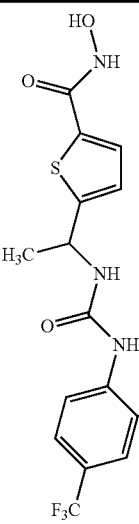
I-25
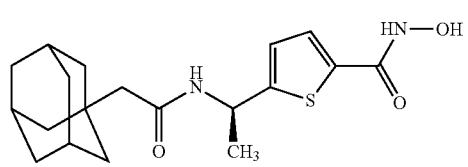 [SMILES: C[C@@H](NC(=O)CC12CC3CC(CC(C3)C1)C2)c1ccc(C(=O)NO)s1]
I-26
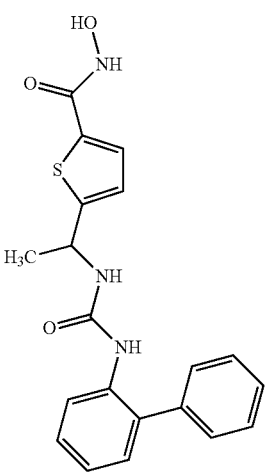 [SMILES: CC(NC(=O)Nc1ccccc1-c1ccccc1)c1ccc(C(=O)NO)s1]
I-27

TABLE 1-continued
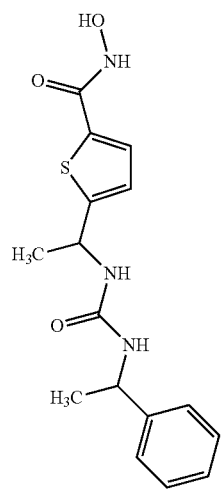 [SMILES: CC(NC(=O)NC(C)c1ccc(C(=O)NO)s1)c1ccccc1]
I-28
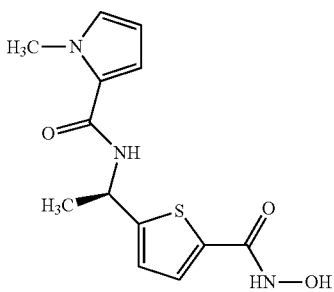
I-29
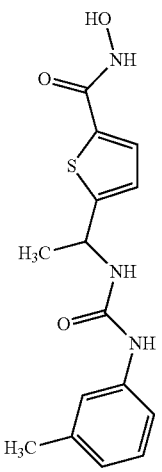 [SMILES: Cc1cccc(NC(=O)NC(C)c2ccc(C(=O)NO)s2)c1]
I-30
TABLE 1-continued
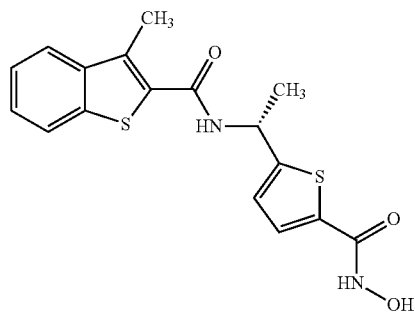 [SMILES: Cc1c(C(=O)N[C@H](C)c2ccc(C(=O)NO)s2)sc2ccccc12]
I-31
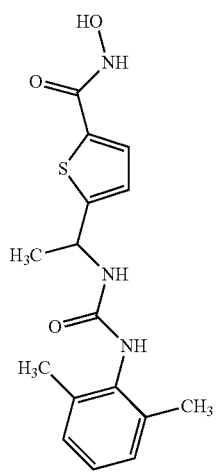 [SMILES: Cc1cccc(C)c1NC(=O)NC(C)c1ccc(C(=O)NO)s1]
I-32
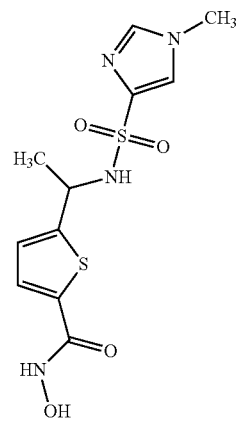 [SMILES: CC(NS(=O)(=O)c1cn(C)cn1)c1ccc(C(=O)NO)s1]
I-33
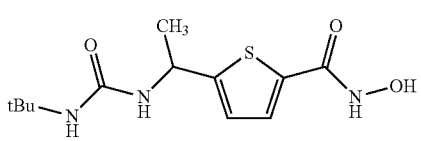 [SMILES: CC(NC(=O)NC(C)(C)C)c1ccc(C(=O)NO)s1]
I-34

TABLE 1-continued
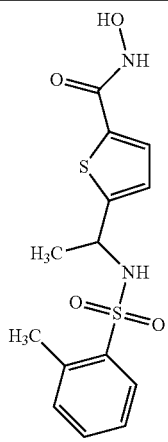
I-35
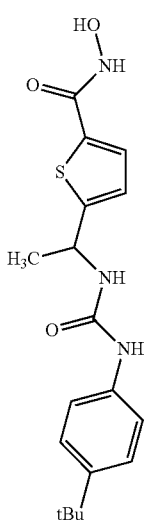 [SMILES: CC(NC(=O)Nc1ccc(C(C)(C)C)cc1)c1ccc(C(=O)NO)s1]
I-36
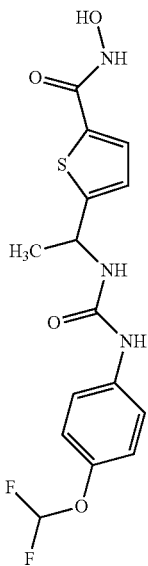 [SMILES: CC(NC(=O)Nc1ccc(OC(F)F)cc1)c1ccc(C(=O)NO)s1]
I-37
TABLE 1-continued
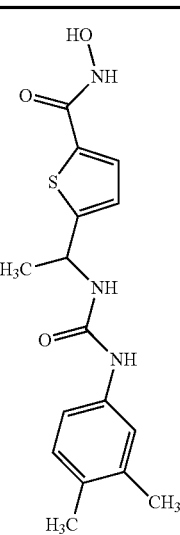
I-38
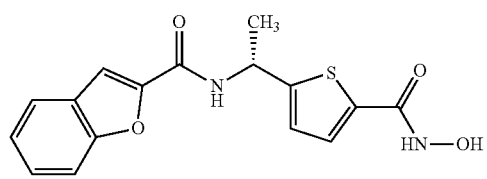 [SMILES: C[C@@H](NC(=O)c1cc2ccccc2o1)c1ccc(C(=O)NO)s1]
I-39
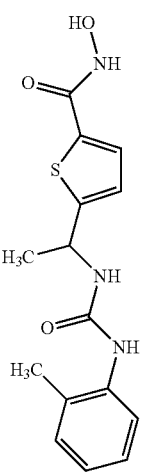 [SMILES: Cc1ccccc1NC(=O)NC(C)c1ccc(C(=O)NO)s1]
I-40

TABLE 1-continued
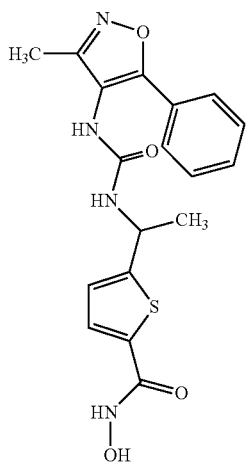 [SMILES: Cc1noc(-c2ccccc2)c1NC(=O)NC(C)c1ccc(C(=O)NO)s1]
I-41
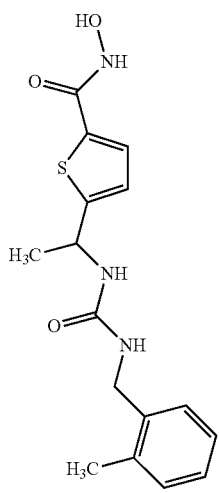 [SMILES: Cc1ccccc1CNC(=O)NC(C)c1ccc(C(=O)NO)s1]
I-42
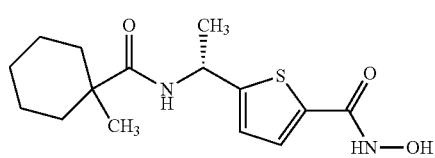 [SMILES: C[C@@H](NC(=O)C1(C)CCCCC1)c1ccc(C(=O)NO)s1]
I-43
TABLE 1-continued
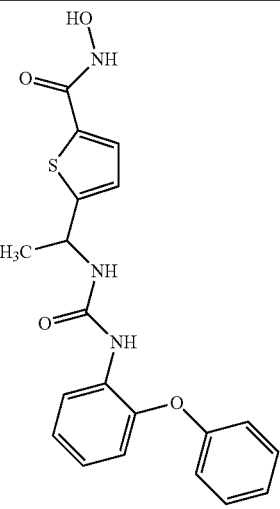
I-44
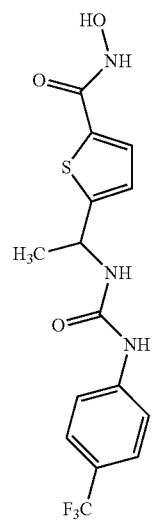 [SMILES: CC(NC(=O)Nc1ccc(C(F)(F)F)cc1)c1ccc(C(=O)NO)s1]
I-45
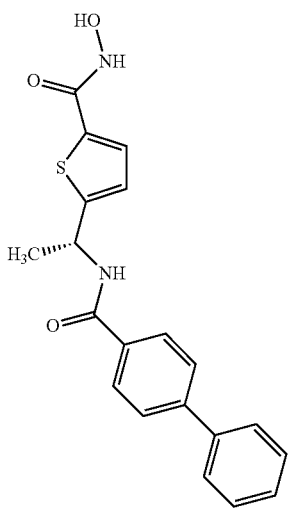 [SMILES: C[C@@H](NC(=O)c1ccc(-c2ccccc2)cc1)c1ccc(C(=O)NO)s1]
I-46

TABLE 1-continued
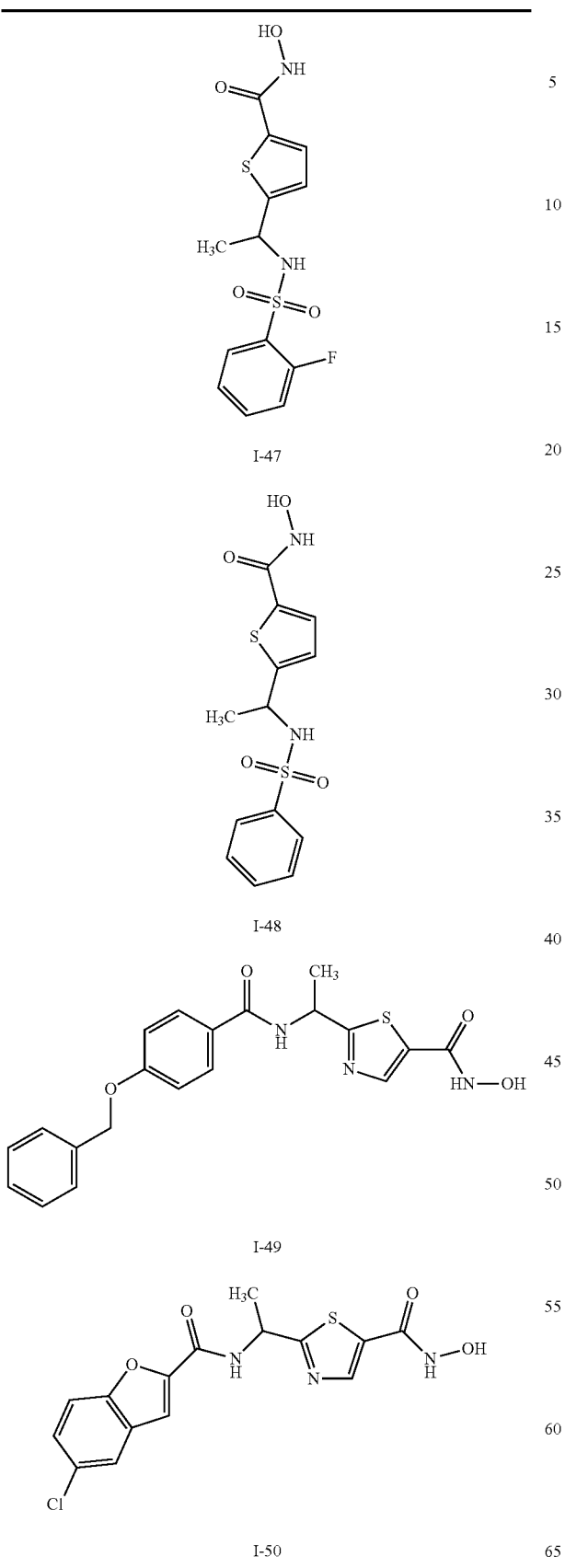
I-47
I-48
I-49
I-50
TABLE 1-continued
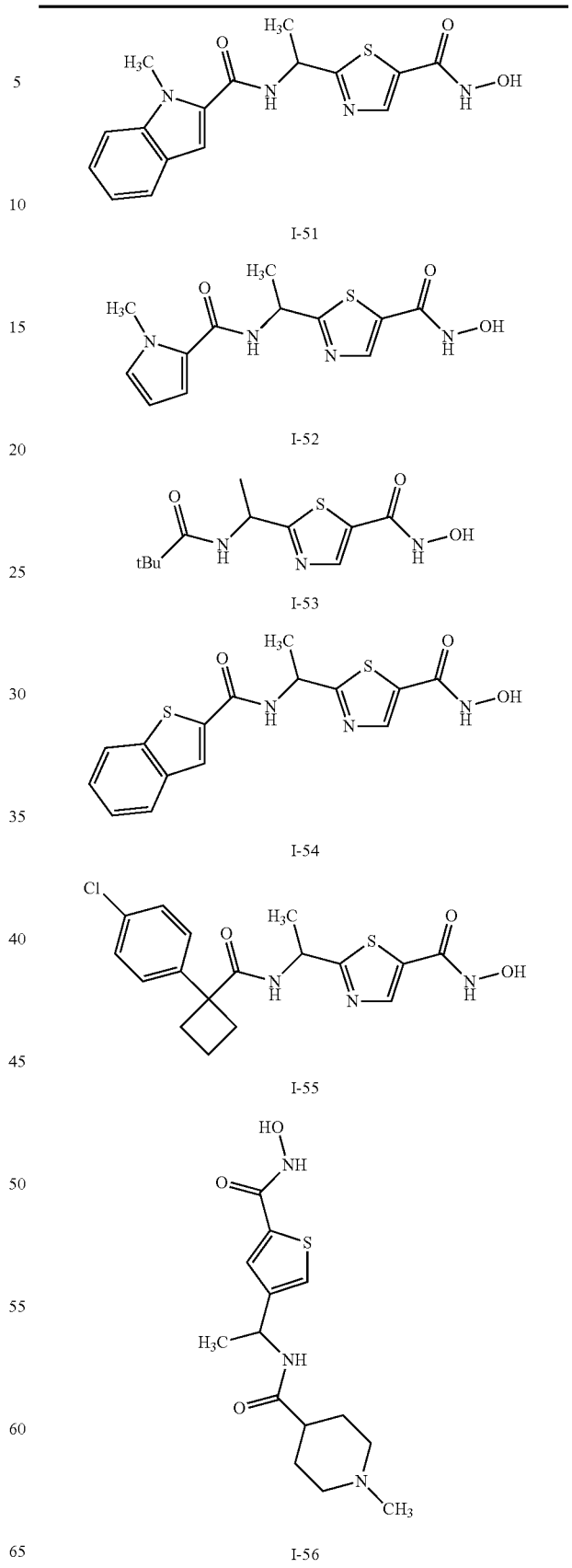
I-51
I-52
I-53
I-54
I-55
I-56

TABLE 1-continued
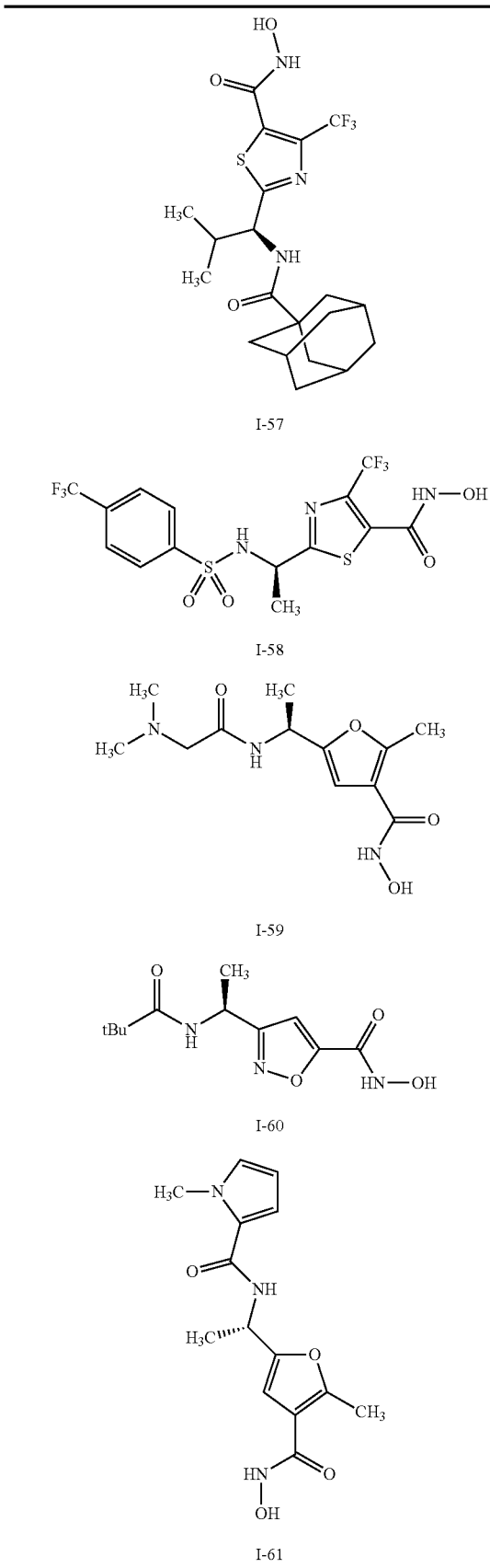
I-57
I-58
I-59
I-60
I-61
TABLE 1-continued
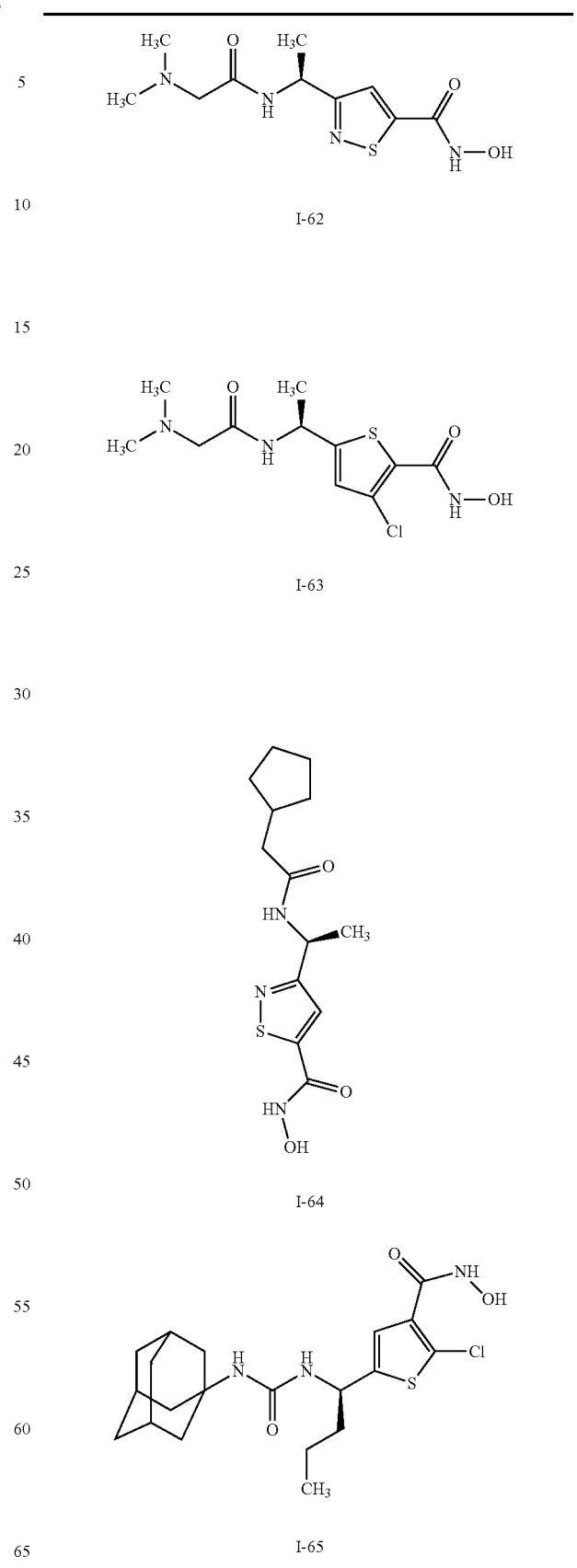
I-62
I-63
I-64
I-65

TABLE 1-continued
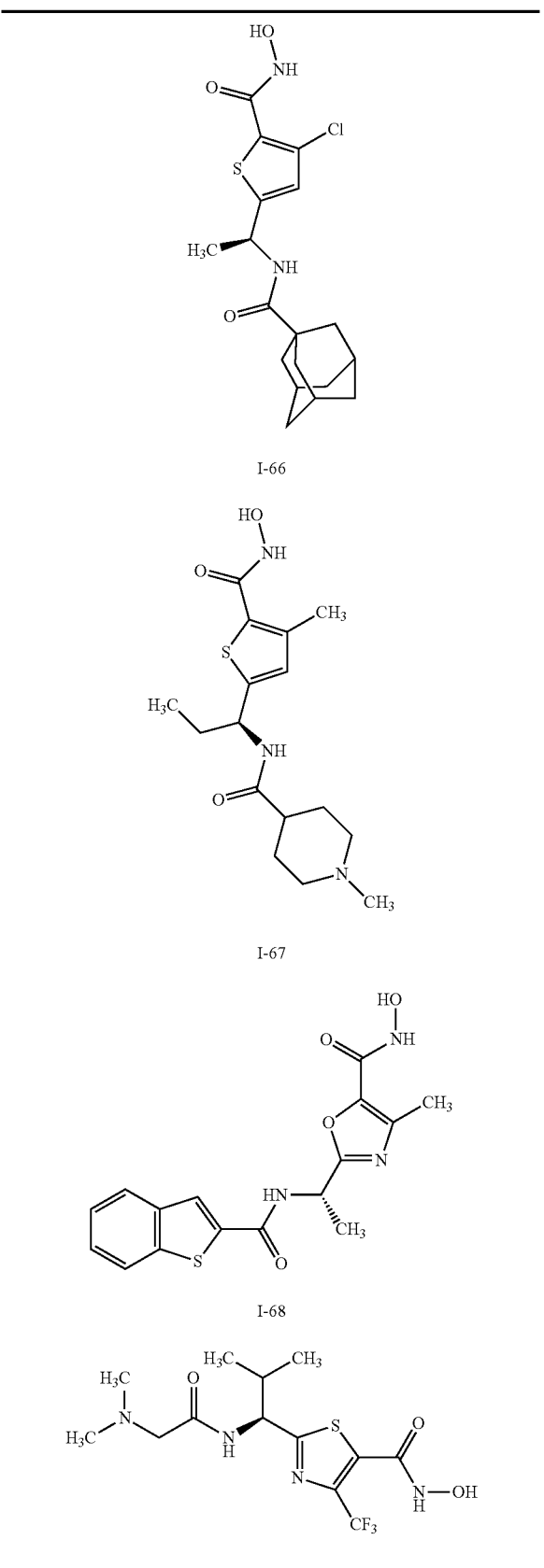
I-66
I-67
I-68
I-69
TABLE 1-continued
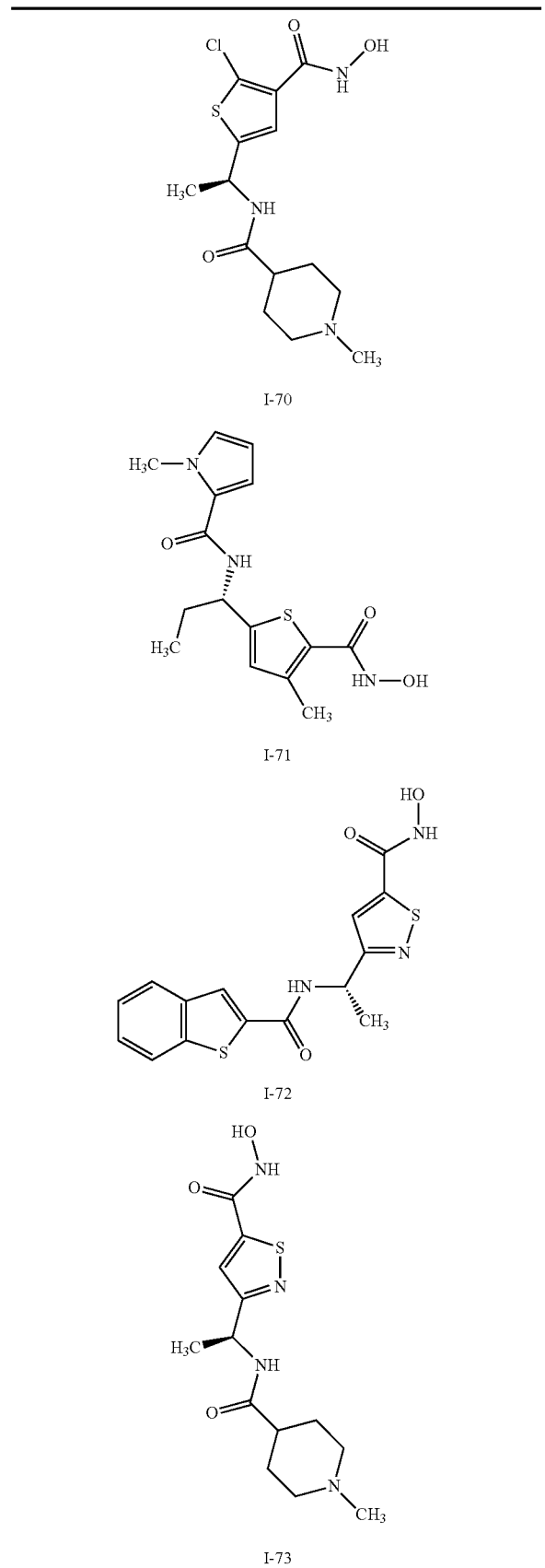
I-70
I-71
I-72
I-73

TABLE 1-continued
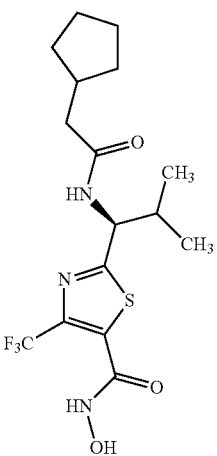 [SMILES: CC(C)[C@H](NC(=O)CC1CCCC1)c1nc(C(F)(F)F)c(C(=O)NO)s1]
I-74
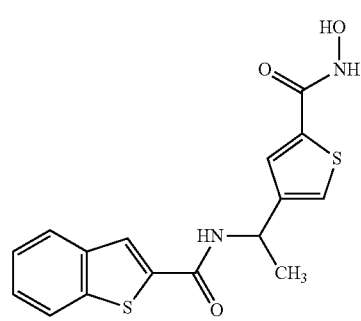 [SMILES: CC(NC(=O)c1cc2ccccc2s1)c1csc(C(=O)NO)c1]
I-75
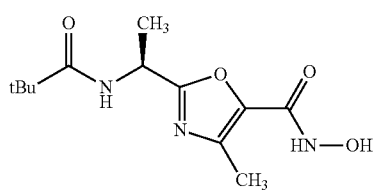 [SMILES: Cc1nc([C@H](C)NC(=O)C(C)(C)C)oc1C(=O)NO]
I-76
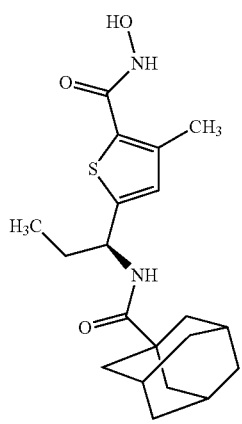 [SMILES: CC[C@H](NC(=O)C12CC3CC(CC(C3)C1)C2)c1cc(C)c(C(=O)NO)s1]
I-77
TABLE 1-continued
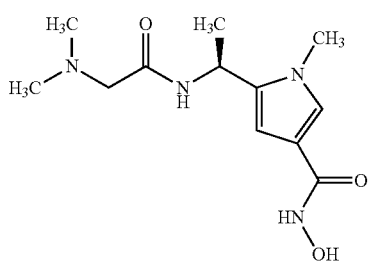 [SMILES: C[C@H](NC(=O)CN(C)C)c1cc(C(=O)NO)cn1C]
I-78
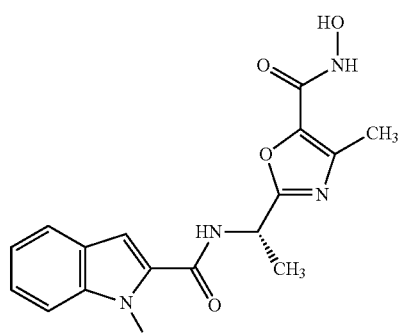
I-79
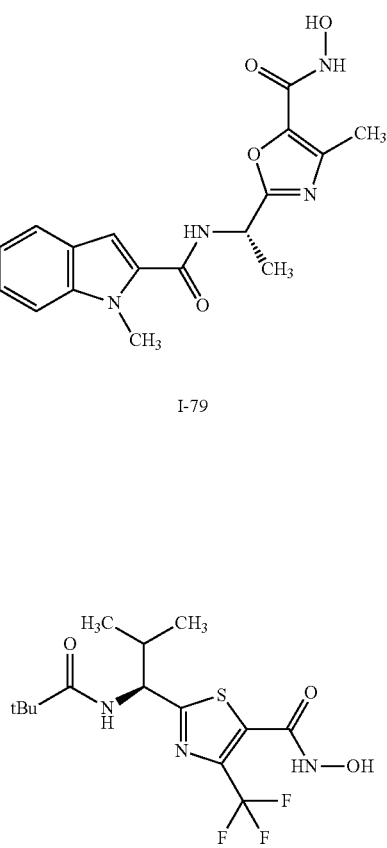
I-80
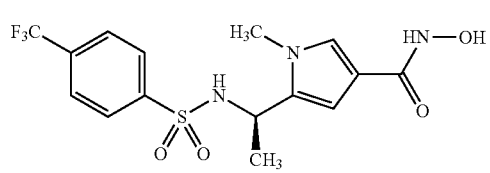 [SMILES: C[C@@H](NS(=O)(=O)c1ccc(C(F)(F)F)cc1)c1cc(C(=O)NO)cn1C]
I-81

TABLE 1-continued
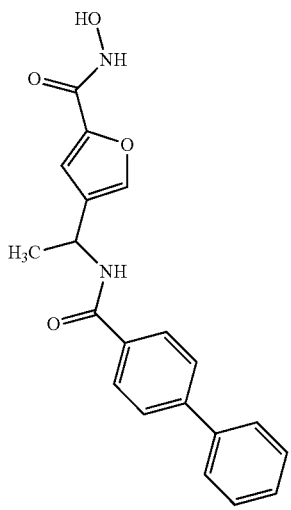 [SMILES: CC(NC(=O)c1ccc(-c2ccccc2)cc1)c1coc(C(=O)NO)c1]
I-82
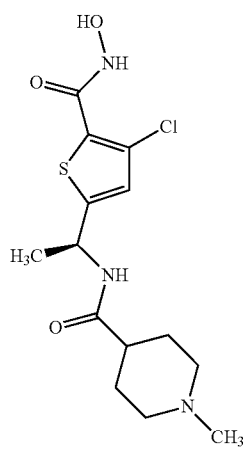 [SMILES: C[C@H](NC(=O)C1CCN(C)CC1)c1cc(Cl)c(C(=O)NO)s1]
I-83
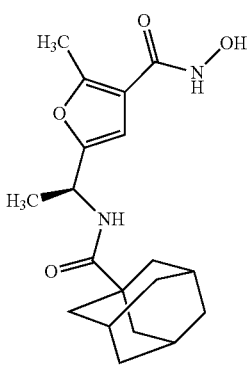 [SMILES: Cc1oc([C@H](C)NC(=O)C23CC4CC(CC(C4)C2)C3)cc1C(=O)NO]
I-84
TABLE 1-continued
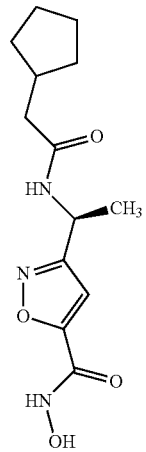 [SMILES: C[C@H](NC(=O)CC1CCCC1)c1cc(C(=O)NO)on1]
I-85
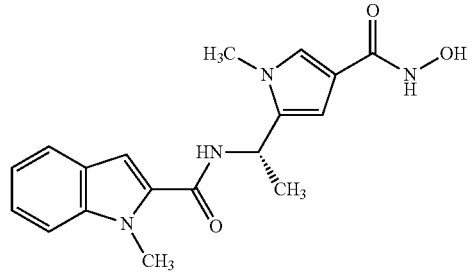 [SMILES: C[C@H](NC(=O)c1cc2ccccc2n1C)c1cc(C(=O)NO)cn1C]
I-86
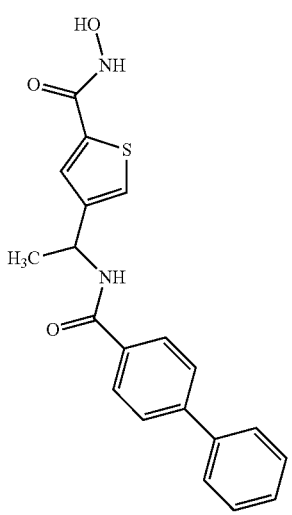 [SMILES: CC(NC(=O)c1ccc(-c2ccccc2)cc1)c1csc(C(=O)NO)c1]
I-87

TABLE 1-continued
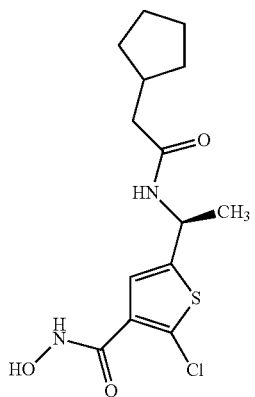 [SMILES: C[C@H](NC(=O)CC1CCCC1)c1cc(C(=O)NO)c(Cl)s1]
I-88
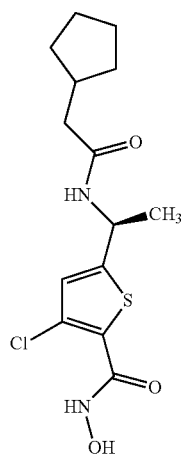 [SMILES: C[C@H](NC(=O)CC1CCCC1)c1cc(Cl)c(C(=O)NO)s1]
I-89
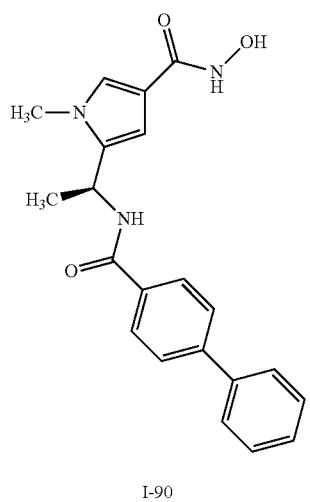
I-90
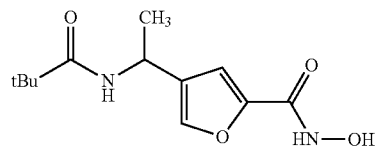
I-91
TABLE 1-continued
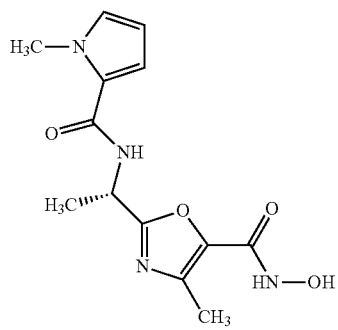 [SMILES: Cc1nc([C@H](C)NC(=O)c2cccn2C)oc1C(=O)NO]
I-92
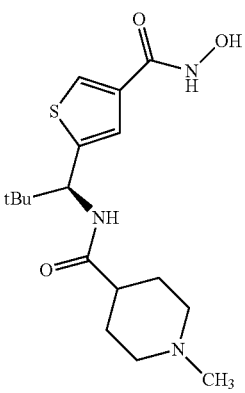 [SMILES: CN1CCC(C(=O)N[C@H](c2cc(C(=O)NO)cs2)C(C)(C)C)CC1]
I-93
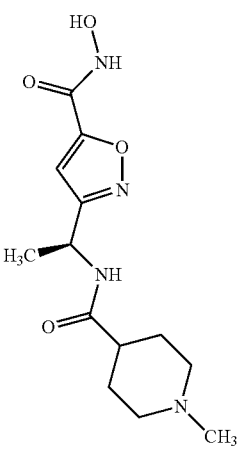
I-94

TABLE 1-continued
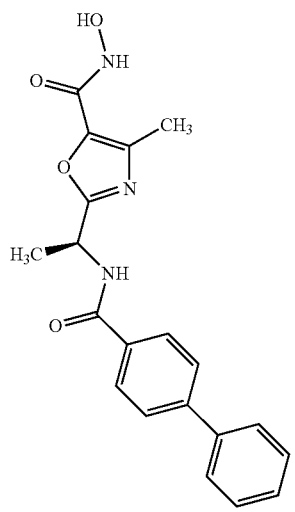
I-95
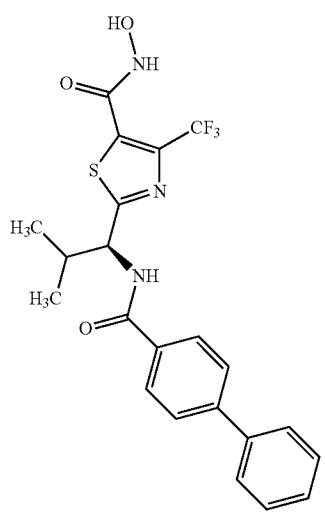 [SMILES: CC(C)[C@H](NC(=O)c1ccc(-c2ccccc2)cc1)c1nc(C(F)(F)F)c(C(=O)NO)s1]
I-96
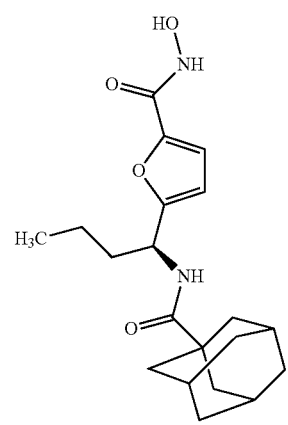 [SMILES: CCC[C@H](NC(=O)C12CC3CC(CC(C3)C1)C2)c1ccc(C(=O)NO)o1]
I-97
TABLE 1-continued
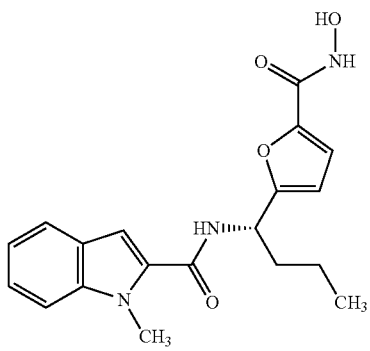 [SMILES: CCC[C@H](NC(=O)c1cc2ccccc2n1C)c1ccc(C(=O)NO)o1]
I-98
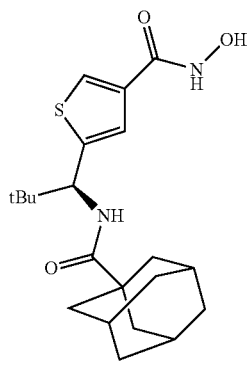 [SMILES: CC(C)(C)[C@H](NC(=O)C12CC3CC(CC(C3)C1)C2)c1cc(C(=O)NO)cs1]
I-99
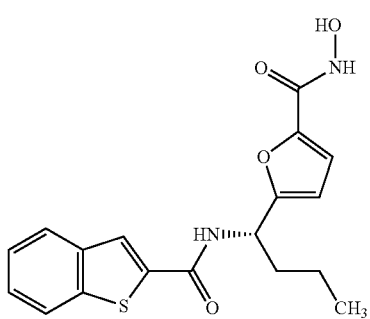 [SMILES: CCC[C@H](NC(=O)c1cc2ccccc2s1)c1ccc(C(=O)NO)o1]
I-100
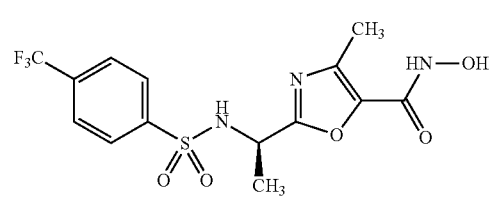 [SMILES: Cc1nc([C@@H](C)NS(=O)(=O)c2ccc(C(F)(F)F)cc2)oc1C(=O)NO]
I-101

TABLE 1-continued
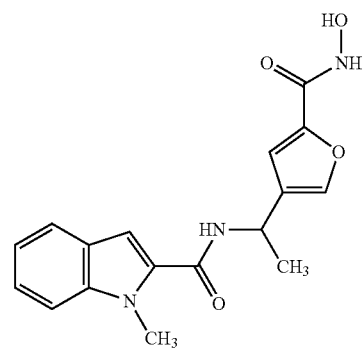 [SMILES: CC(NC(=O)c1cc2ccccc2n1C)c1coc(C(=O)NO)c1]
I-102
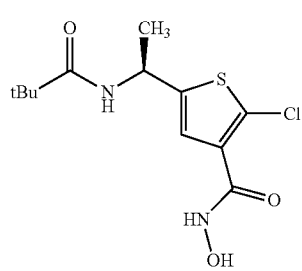 [SMILES: C[C@H](NC(=O)C(C)(C)C)c1cc(C(=O)NO)c(Cl)s1]
I-103
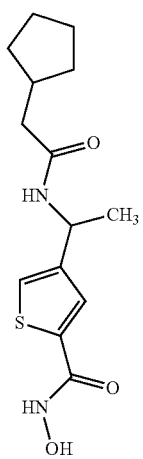 [SMILES: CC(NC(=O)CC1CCCC1)c1csc(C(=O)NO)c1]
I-104
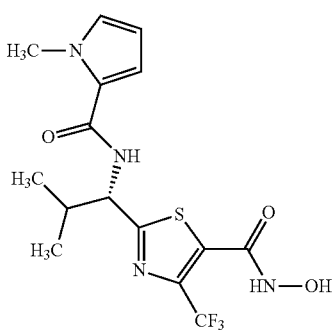 [SMILES: CC(C)[C@H](NC(=O)c1cccn1C)c1nc(C(F)(F)F)c(C(=O)NO)s1]
I-105
TABLE 1-continued
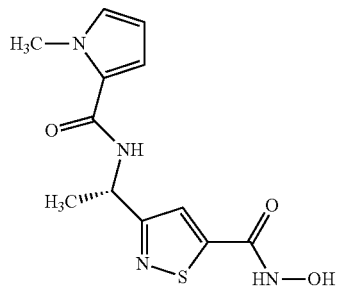 [SMILES: C[C@H](NC(=O)c1cccn1C)c1cc(C(=O)NO)sn1]
I-106
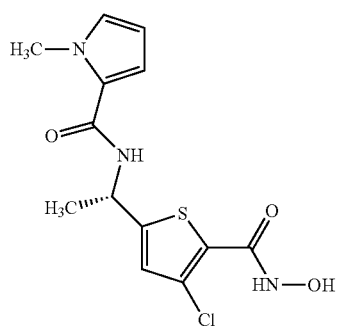 [SMILES: C[C@H](NC(=O)c1cccn1C)c1cc(Cl)c(C(=O)NO)s1]
I-107
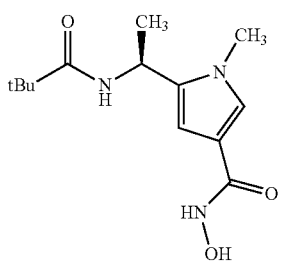 [SMILES: C[C@H](NC(=O)C(C)(C)C)c1cc(C(=O)NO)cn1C]
I-108
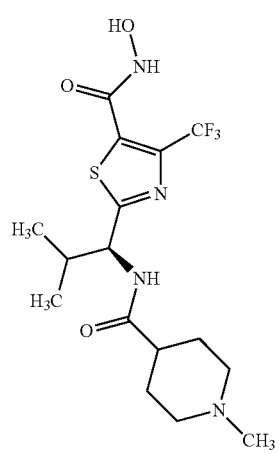 [SMILES: CC(C)[C@H](NC(=O)C1CCN(C)CC1)c1nc(C(F)(F)F)c(C(=O)NO)s1]
I-109

TABLE 1-continued
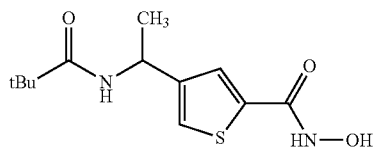 [SMILES: CC(NC(=O)C(C)(C)C)c1csc(C(=O)NO)c1]
I-110
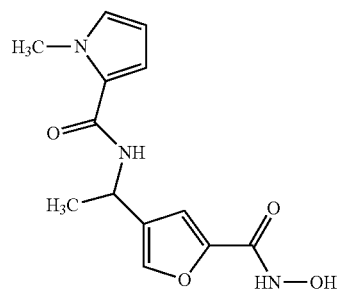 [SMILES: CC(NC(=O)c1cccn1C)c1coc(C(=O)NO)c1]
I-111
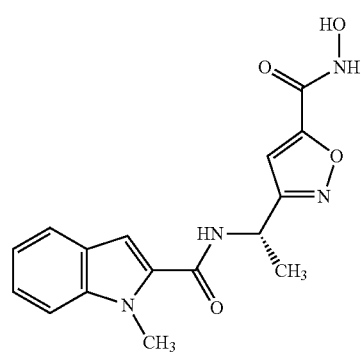 [SMILES: C[C@H](NC(=O)c1cc2ccccc2n1C)c1cc(C(=O)NO)on1]
I-112
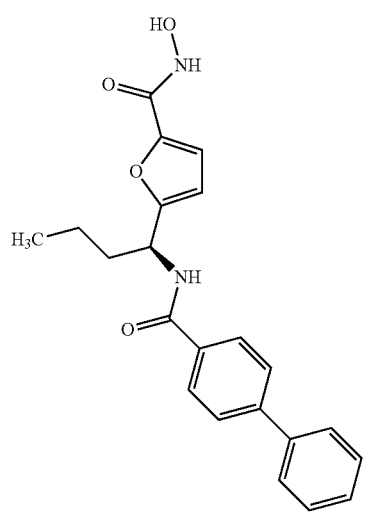 [SMILES: CCC[C@H](NC(=O)c1ccc(-c2ccccc2)cc1)c1ccc(C(=O)NO)o1]
I-113
TABLE 1-continued
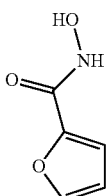
I-114
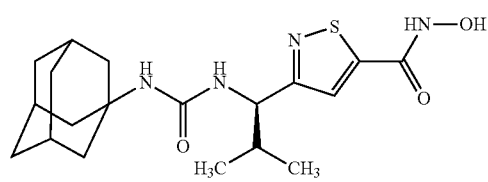 [SMILES: CC(C)[C@@H](NC(=O)NC12CC3CC(CC(C3)C1)C2)c1cc(C(=O)NO)sn1]
I-115
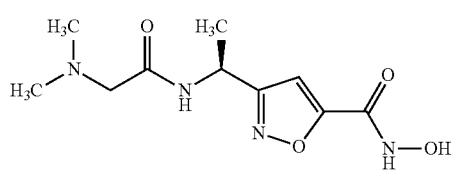 [SMILES: C[C@H](NC(=O)CN(C)C)c1cc(C(=O)NO)on1]
I-116
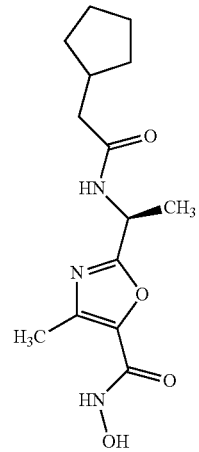 [SMILES: Cc1nc([C@H](C)NC(=O)CC2CCCC2)oc1C(=O)NO]
I-117

TABLE 1-continued
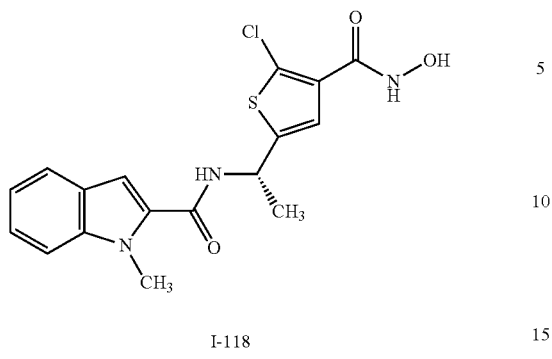
I-118
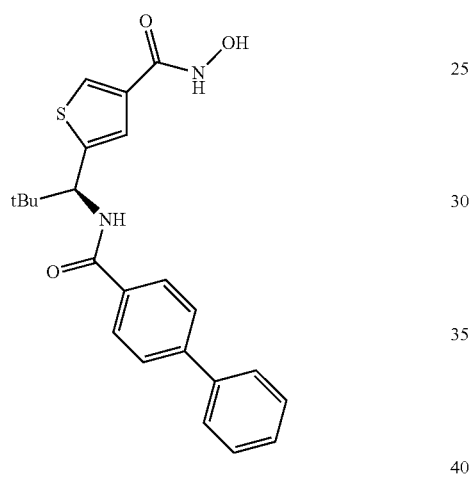
I-119
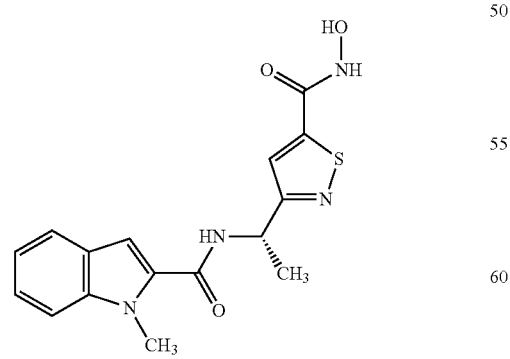
I-120
TABLE 1-continued
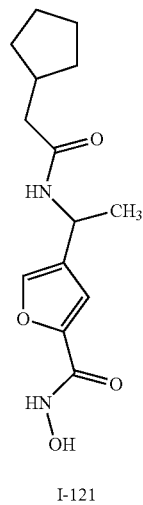
I-121
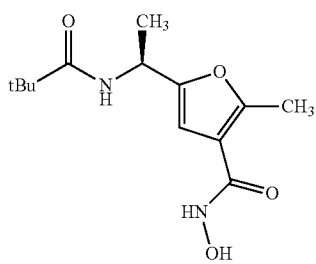 [SMILES: Cc1oc([C@H](C)NC(=O)C(C)(C)C)cc1C(=O)NO]
I-122
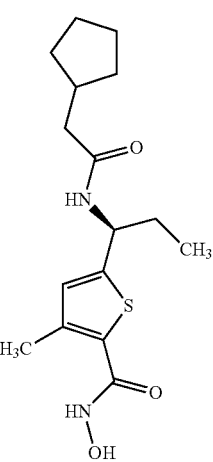 [SMILES: CC[C@H](NC(=O)CC1CCCC1)c1cc(C)c(C(=O)NO)s1]
I-123

TABLE 1-continued
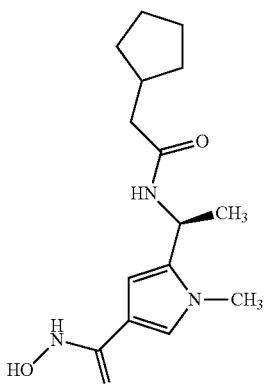
I-124
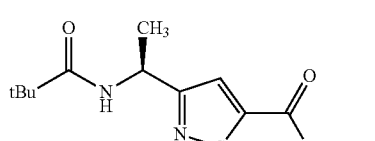
I-125
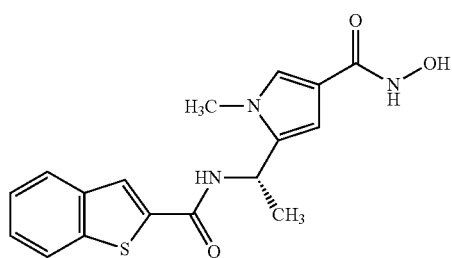 [SMILES: C[C@H](NC(=O)c1cc2ccccc2s1)c1cc(C(=O)NO)cn1C]
I-126
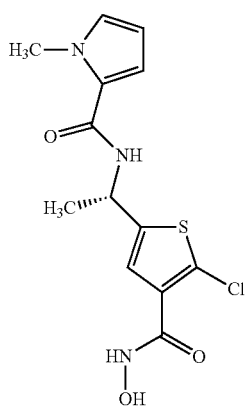 [SMILES: C[C@H](NC(=O)c1cccn1C)c1cc(C(=O)NO)c(Cl)s1]
I-127
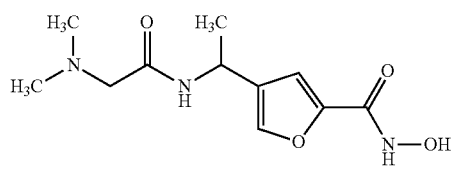 [SMILES: CC(NC(=O)CN(C)C)c1coc(C(=O)NO)c1]
I-128
TABLE 1-continued
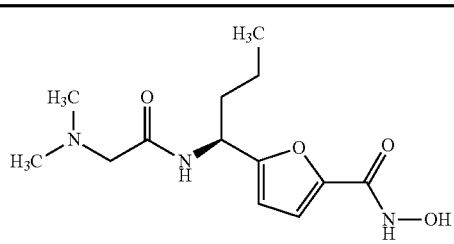
I-129
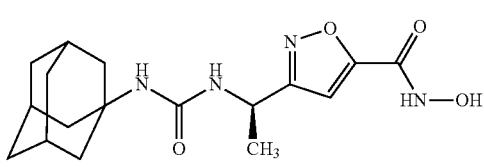 [SMILES: C[C@@H](NC(=O)NC12CC3CC(CC(C3)C1)C2)c1cc(C(=O)NO)on1]
I-130
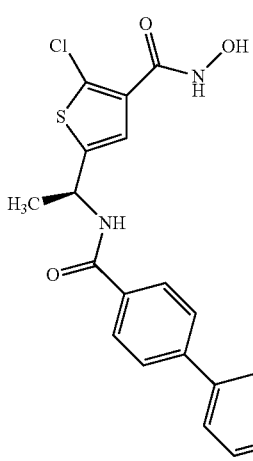
I-131
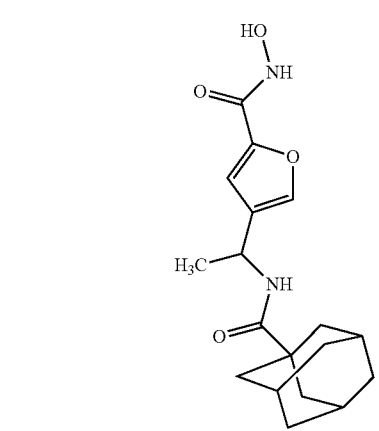
I-132

TABLE 1-continued
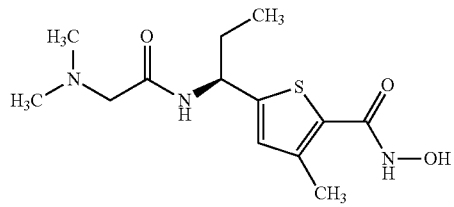 [SMILES: CC[C@H](NC(=O)CN(C)C)c1cc(C)c(C(=O)NO)s1]
I-133
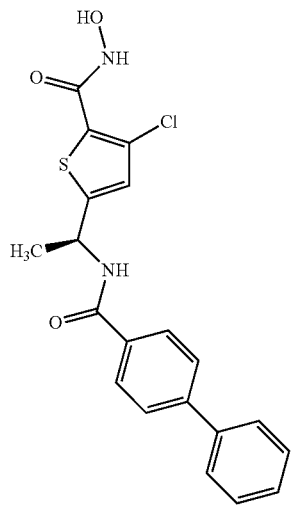 [SMILES: C[C@H](NC(=O)c1ccc(-c2ccccc2)cc1)c1cc(Cl)c(C(=O)NO)s1]
I-134
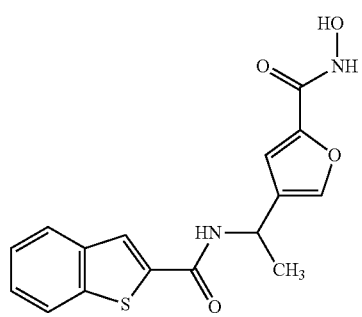 [SMILES: CC(NC(=O)c1cc2ccccc2s1)c1coc(C(=O)NO)c1]
I-135
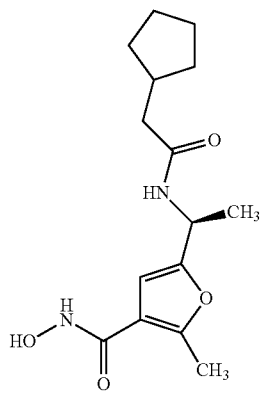 [SMILES: Cc1oc([C@H](C)NC(=O)CC2CCCC2)cc1C(=O)NO]
I-136
TABLE 1-continued
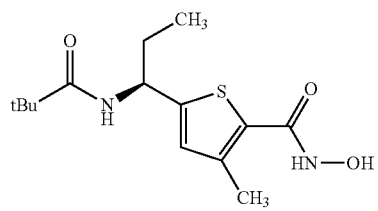
I-137
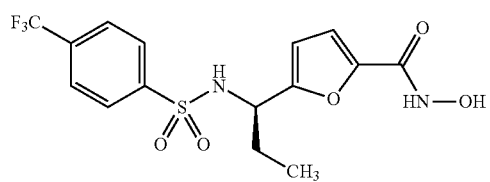
I-138
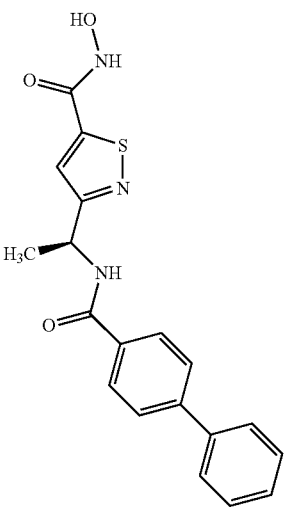 [SMILES: C[C@H](NC(=O)c1ccc(-c2ccccc2)cc1)c1cc(C(=O)NO)sn1]
I-139
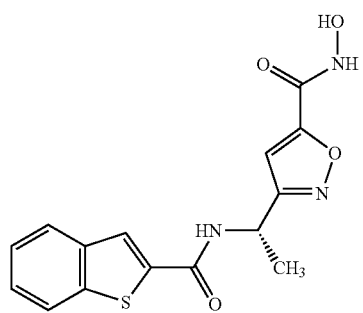
I-140

TABLE 1-continued
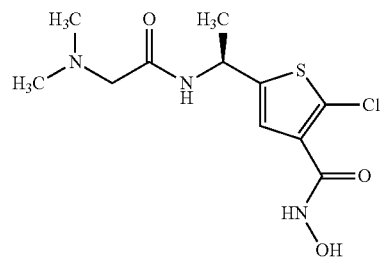 [SMILES: C[C@H](NC(=O)CN(C)C)c1cc(C(=O)NO)c(Cl)s1]
I-141
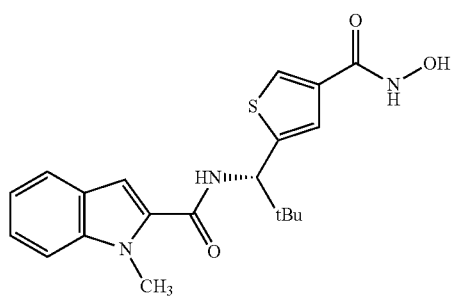 [SMILES: Cn1c(C(=O)N[C@H](c2cc(C(=O)NO)cs2)C(C)(C)C)cc2ccccc21]
I-142
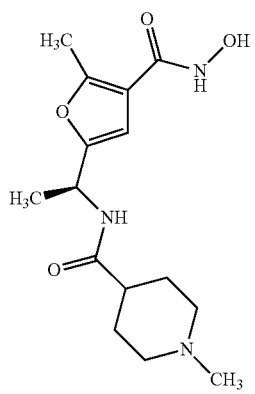
I-143
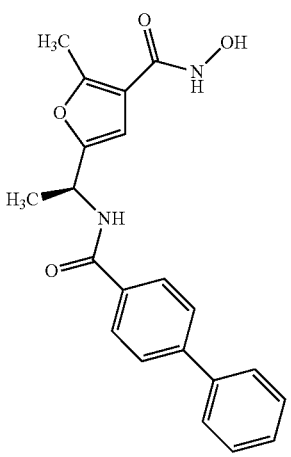 [SMILES: Cc1oc([C@H](C)NC(=O)c2ccc(-c3ccccc3)cc2)cc1C(=O)NO]
I-144
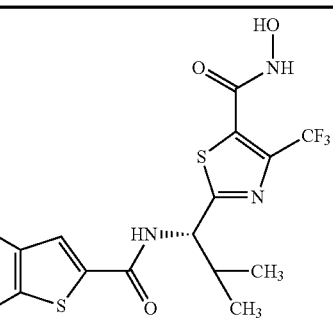
I-145
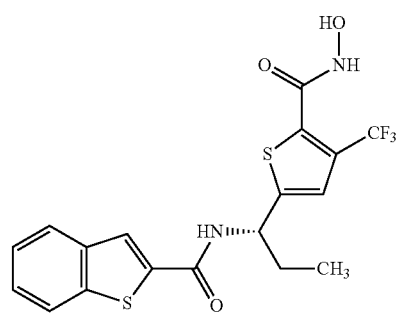 [SMILES: CC[C@H](NC(=O)c1cc2ccccc2s1)c1cc(C(F)(F)F)c(C(=O)NO)s1]
I-146
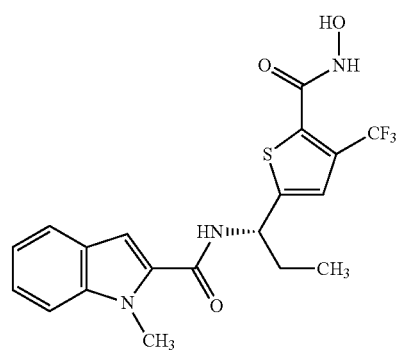 [SMILES: CC[C@H](NC(=O)c1cc2ccccc2n1C)c1cc(C(F)(F)F)c(C(=O)NO)s1]
I-147
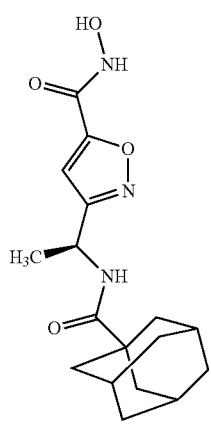 [SMILES: C[C@H](NC(=O)C12CC3CC(CC(C3)C1)C2)c1cc(C(=O)NO)on1]
I-148

TABLE 1-continued
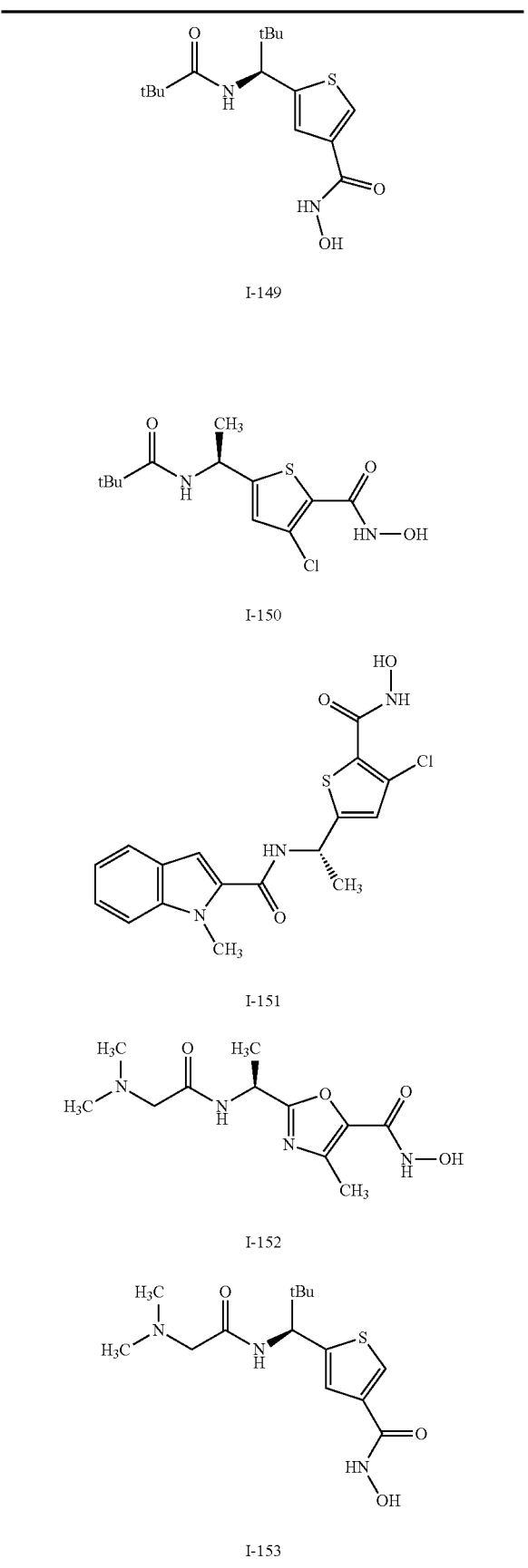
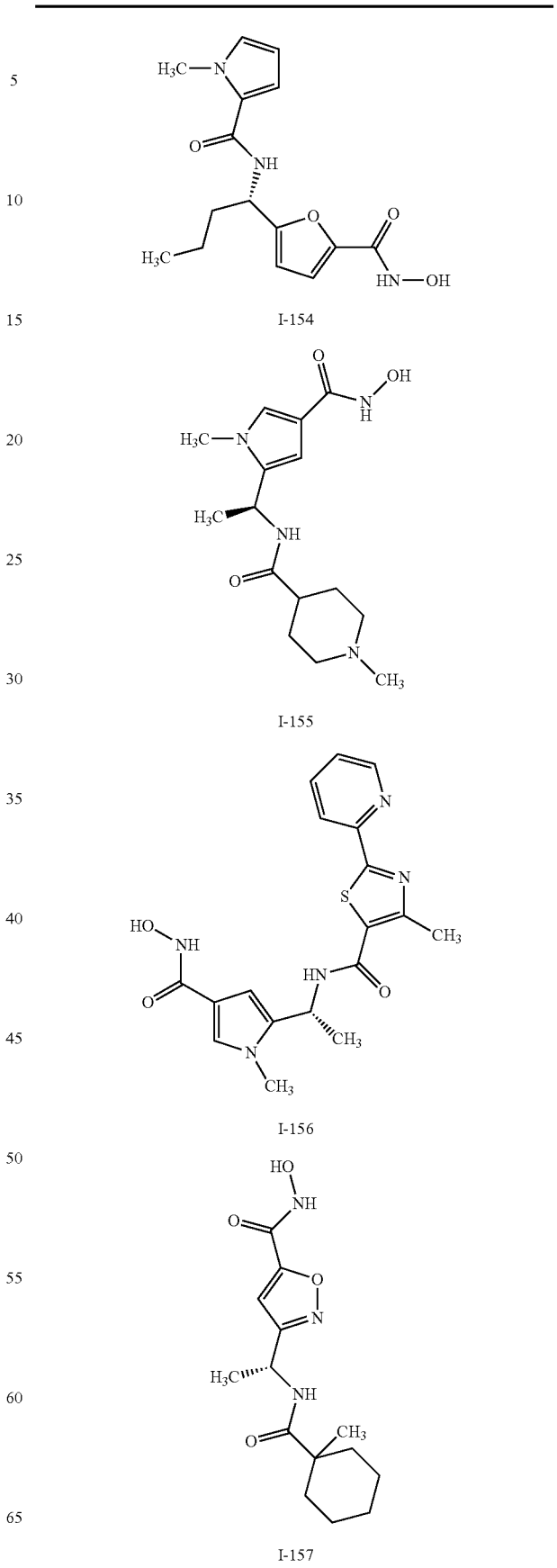

TABLE 1-continued
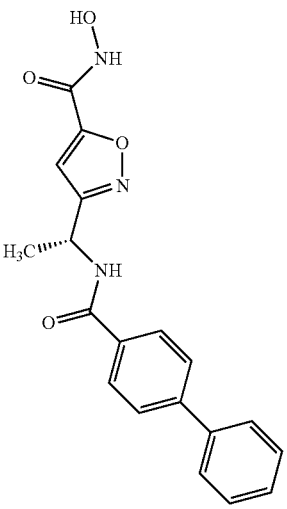 [SMILES: C[C@@H](NC(=O)c1ccc(-c2ccccc2)cc1)c1cc(C(=O)NO)on1]
I-158
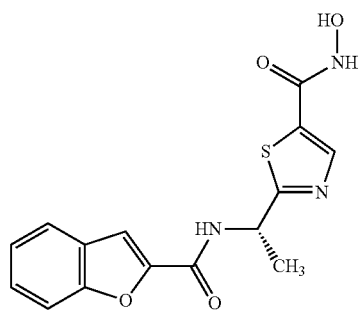 [SMILES: C[C@H](NC(=O)c1cc2ccccc2o1)c1ncc(C(=O)NO)s1]
I-159
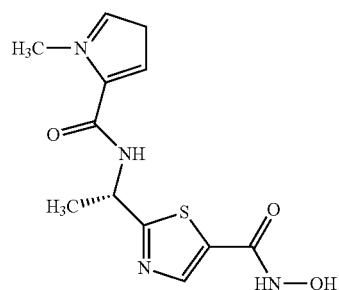
I-160
TABLE 1-continued
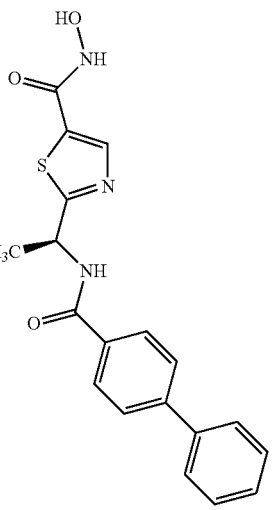
I-161
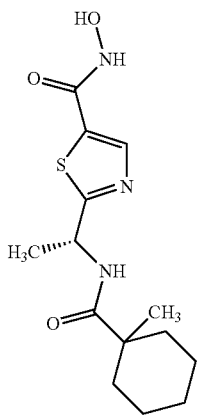 [SMILES: C[C@@H](NC(=O)C1(C)CCCCC1)c1ncc(C(=O)NO)s1]
I-162
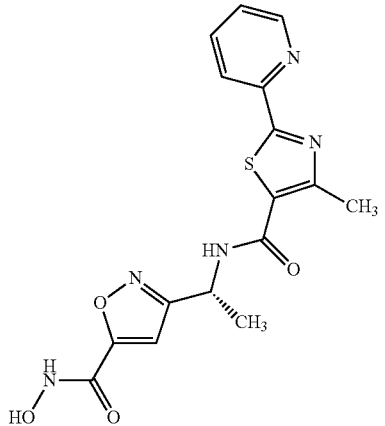 [SMILES: Cc1nc(-c2ccccn2)sc1C(=O)N[C@H](C)c1cc(C(=O)NO)on1]
I-163

TABLE 1-continued
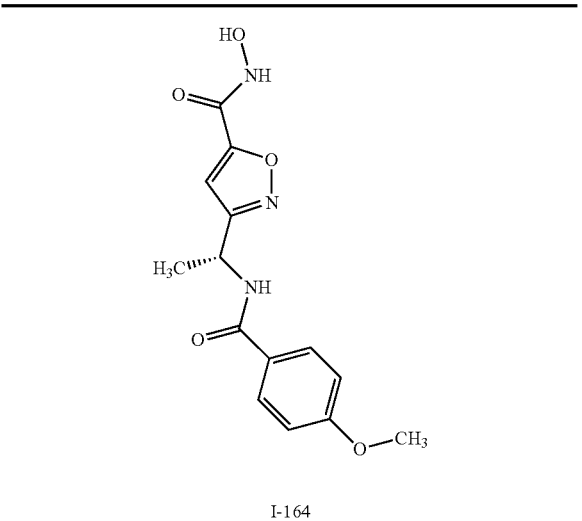
I-164
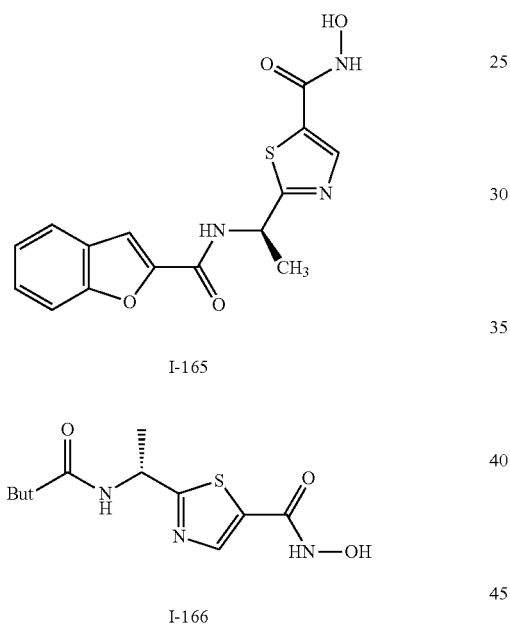
I-165
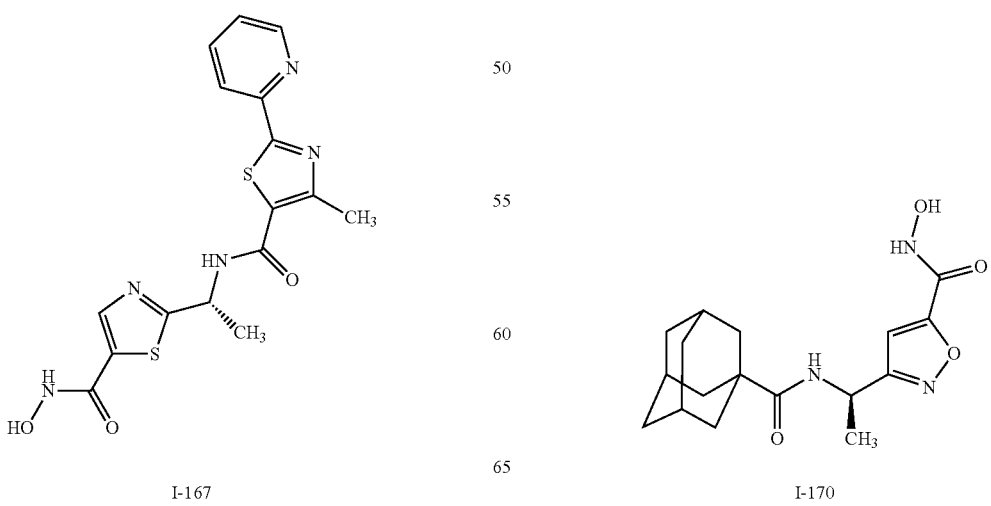
I-166
I-167
TABLE 1-continued
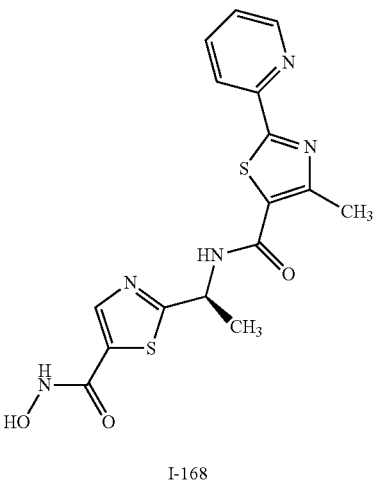
I-168
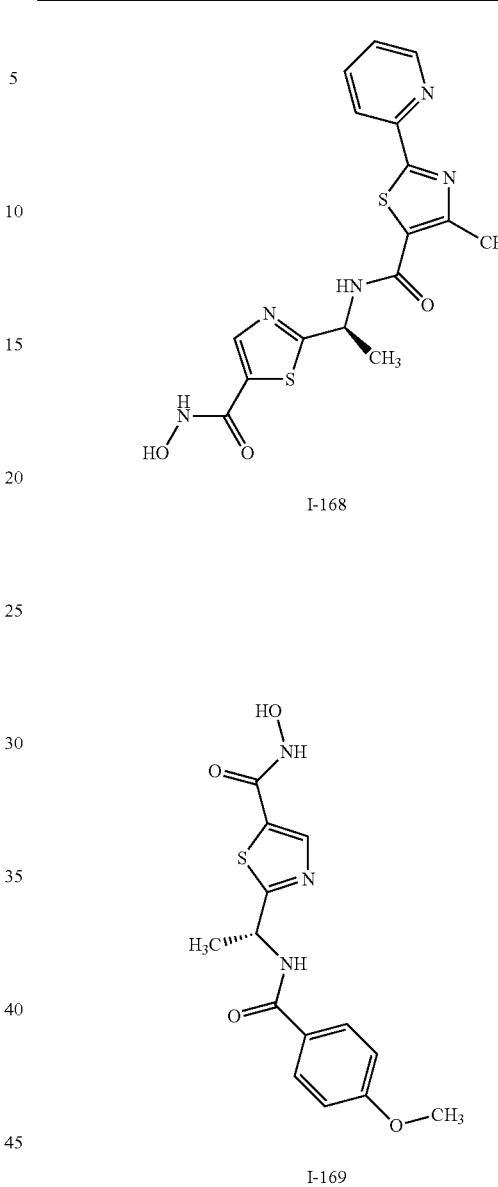
I-169
I-170

TABLE 1-continued
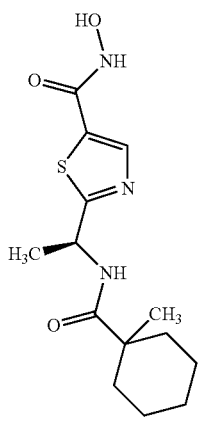 [SMILES: C[C@H](NC(=O)C1(C)CCCCC1)c1ncc(C(=O)NO)s1]
I-171
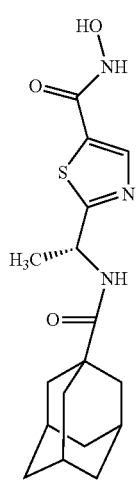 [SMILES: C[C@@H](NC(=O)C12CC3CC(CC(C3)C1)C2)c1ncc(C(=O)NO)s1]
I-172
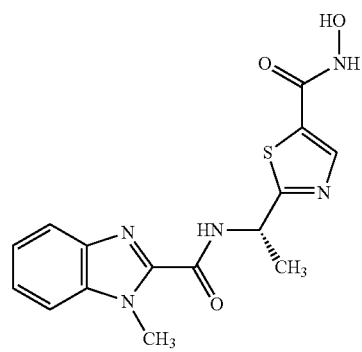 [SMILES: C[C@H](NC(=O)c1nc2ccccc2n1C)c1ncc(C(=O)NO)s1]
I-173
TABLE 1-continued
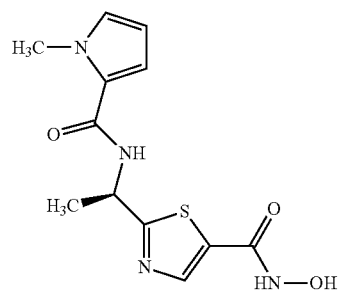 [SMILES: C[C@@H](NC(=O)c1cccn1C)c1ncc(C(=O)NO)s1]
I-174
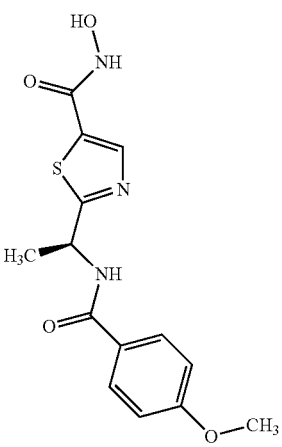 [SMILES: COc1ccc(C(=O)N[C@@H](C)c2ncc(C(=O)NO)s2)cc1]
I-175
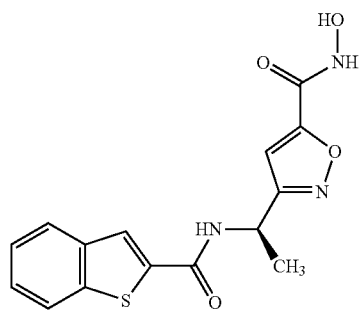 [SMILES: C[C@@H](NC(=O)c1cc2ccccc2s1)c1cc(C(=O)NO)on1]
I-176

TABLE 1-continued
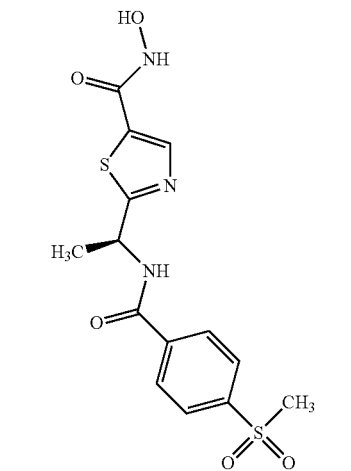 [SMILES: C[C@H](NC(=O)c1ccc(S(C)(=O)=O)cc1)c1ncc(C(=O)NO)s1]
I-177
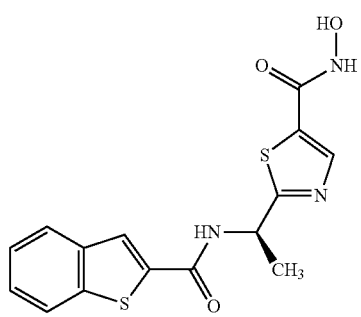 [SMILES: C[C@@H](NC(=O)c1cc2ccccc2s1)c1ncc(C(=O)NO)s1]
I-178
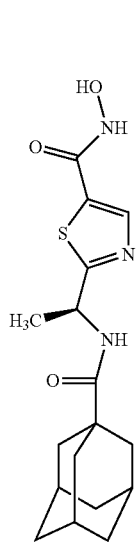 [SMILES: C[C@H](NC(=O)C12CC3CC(CC(C3)C1)C2)c1ncc(C(=O)NO)s1]
I-179
TABLE 1-continued
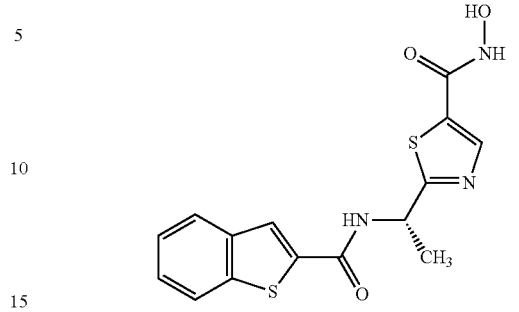
I-180
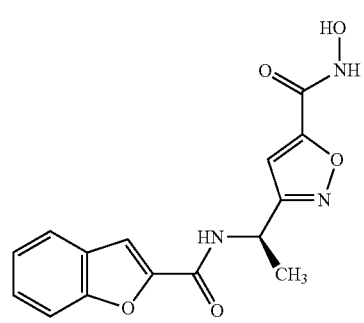 [SMILES: C[C@@H](NC(=O)c1cc2ccccc2o1)c1cc(C(=O)NO)on1]
I-181
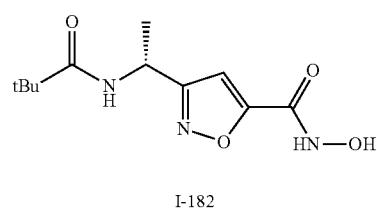
I-182
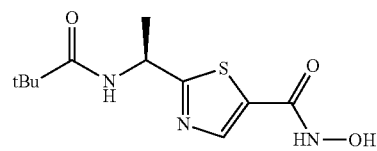 [SMILES: C[C@H](NC(=O)C(C)(C)C)c1ncc(C(=O)NO)s1]
I-183
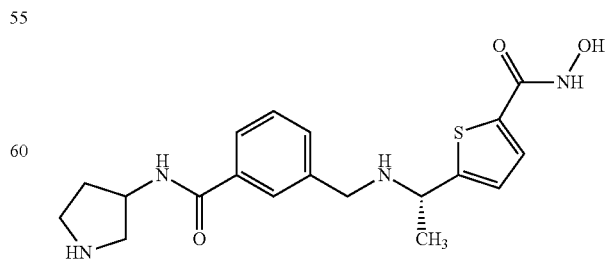
I-184

TABLE 1-continued

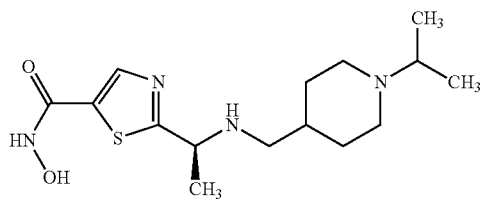 [SMILES: CC(C)N1CCC(CN[C@@H](C)c2ncc(C(=O)NO)s2)CC1]

I-185

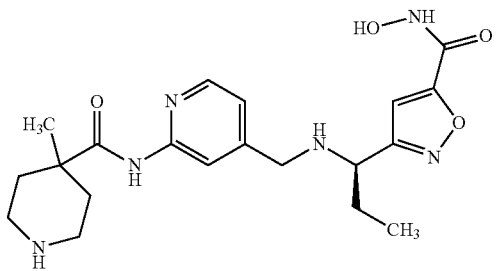 [SMILES: CC[C@@H](NCc1ccnc(NC(=O)C2(C)CCNCC2)c1)c1cc(C(=O)NO)on1]

I-186

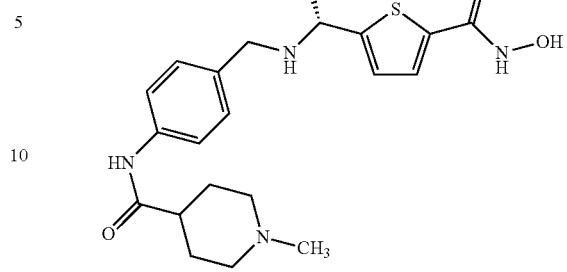

I-187

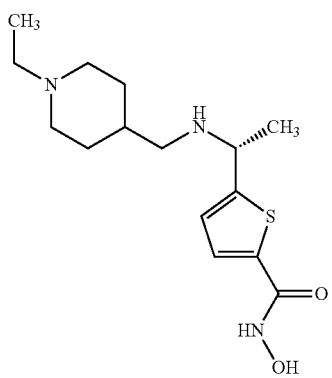 [SMILES: CCN1CCC(CN[C@H](C)c2ccc(C(=O)NO)s2)CC1]

I-188

The compounds in Table 1 above may also be identified by the following chemical names:

| | |
|---|---|
| I-1 | 5-(1-{[(cyclopentylamino)carbonyl]amino}ethyl)-N-hydroxythiophene-2-carboxamide |
| I-2 | 5-[1-({[(4-fluorophenyl)amino]carbonyl}amino)ethyl]-N-hydroxythiophene-2-carboxamide |
| I-3 | N-hydroxy-5-{1-[({[3-(trifluoromethyl)phenyl]amino}carbonyl)amino]ethyl}thiophene-2-carboxamide |
| I-4 | 5-[1-({[(3,5-dichlorophenyl)amino]carbonyl}amino)ethyl]-N-hydroxythiophene-2-carboxamide |
| I-5 | N-((1R)-1-{5-[(hydroxyamino)carbonyl]-2-thienyl}ethyl)-1-methyl-1H-indole-2-carboxamide |
| I-6 | 5-{(1R)-1-[(2,2-dimethylpropanoyl)amino]ethyl}-N-hydroxythiophene-2-carboxamide |
| I-7 | 5-{1-[({[2-fluoro-5-(trifluoromethyl)phenyl]amino}carbonyl)amino]ethyl}-N-hydroxythiophene-2-carboxamide |
| I-8 | 5-((1R)-1-{[(tert-butylamino)carbonyl]amino}ethyl)-N-hydroxythiophene-2-carboxamide |
| I-9 | N-hydroxy-5-{(1R)-1-[(4-methoxybenzoyl)amino]ethyl}thiophene-2-carboxamide |
| I-10 | 5-{1-[({[4-chloro-3-(trifluoromethyl)phenyl]amino}carbonyl)amino]ethyl}-N-hydroxythiophene-2-carboxamide |
| I-11 | 5-{(1R)-1-[(1-adamantylcarbonyl)amino]ethyl}-N-hydroxythiophene-2-carboxamide |
| I-12 | 5-{1-[(anilinocarbonyl)amino]ethyl}-N-hydroxythiophene-2-carboxamide |
| I-13 | 5-[1-({[(2,4-dimethylphenyl)amino]carbonyl}amino)ethyl]-N-hydroxythiophene-2-carboxamide |
| I-14 | N-hydroxy-5-[1-({[(4-phenoxyphenyl)amino]carbonyl}amino)ethyl]thiophene-2-carboxamide |
| I-15 | N-((1R)-1-{5-[(hydroxyamino)carbonyl]-2-thienyl}ethyl)-3-methyl-1-benzofuran-2-carboxamide |
| I-16 | N-((1R)-1-{5-[(hydroxyamino)carbonyl]-2-thienyl}ethyl)-1-benzothiophene-2-carboxamide |
| I-17 | 4,5-dichloro-N-((1R)-1-{5-[(hydroxyamino)carbonyl]-2-thienyl}ethyl)-1-methyl-1H-pyrrole-2-carboxamide |
| I-18 | 5-(1-{[(benzylamino)carbonyl]amino}ethyl)-N-hydroxythiophene-2-carboxamide |
| I-19 | N-hydroxy-5-[1-({[(2-methoxy-5-methylphenyl)amino]carbonyl}amino)ethyl]thiophene-2-carboxamide |

| | |
|---|---|
| I-20 | 5-[1-({[(2,6-difluorophenyl)amino]carbonyl}amino)ethyl]-N-hydroxythiophene-2-carboxamide |
| I-21 | N-((1S)-1-{5-[(hydroxyamino)carbonyl]-2-thienyl}ethyl)-1-benzothiophene-2-carboxamide |
| I-22 | N-hydroxy-5-{1-[({[4-(trifluoromethoxy)phenyl]amino}carbonyl)amino]ethyl}thiophene-2-carboxamide |
| I-23 | N-hydroxy-5-[(1R)-1-({[4-(trifluoromethyl)phenyl]sulfonyl}amino)ethyl]thiophene-2-carboxamide |
| I-24 | 5-(1-{[(cyclohexylamino)carbonyl]amino}ethyl)-N-hydroxythiophene-2-carboxamide |
| I-25 | 5-{1-[({[2-chloro-4-(trifluoromethyl)phenyl]amino}carbonyl)amino]ethyl}-N-hydroxythiophene-2-carboxamide |
| I-26 | 5-[(1R)-1-({[(3S,5S,1S)-1-adamantylamino]carbonyl}amino)ethyl]-N-hydroxythiophene-2-carboxamide |
| I-27 | 5-(1-{[(biphenyl-2-ylamino)carbonyl]amino}ethyl)-N-hydroxythiophene-2-carboxamide |
| I-28 | N-hydroxy-5-[1-({[(1-phenylethyl)amino]carbonyl}amino)ethyl]thiophene-2-carboxamide |
| I-29 | N-((1R)-1-{5-[(hydroxyamino)carbonyl]-2-thienyl}ethyl)-1-methyl-1H-pyrrole-2-carboxamide |
| I-30 | N-hydroxy-5-[1-({[(3-methylphenyl)amino]carbonyl}amino)ethyl]thiophene-2-carboxamide |
| I-31 | N-((1R)-1-{5-[(hydroxyamino)carbonyl]-2-thienyl}ethyl)-3-methyl-1-benzothiophene-2-carboxamide |
| I-32 | 5-[1-({[(2,6-dimethylphenyl)amino]carbonyl}amino)ethyl]-N-hydroxythiophene-2-carboxamide |
| I-33 | N-hydroxy-5-(1-{[(1-methyl-1H-imidazol-4-yl)sulfonyl]amino}ethyl)thiophene-2-carboxamide |
| I-34 | 5-(1-{[(tert-butylamino)carbonyl]amino}ethyl)-N-hydroxythiophene-2-carboxamide |
| I-35 | N-hydroxy-5-(1-{[(2-methylphenyl)sulfonyl]amino}ethyl)thiophene-2-carboxamide |
| I-36 | 5-[1-({[(4-tert-butylphenyl)amino]carbonyl}amino)ethyl]-N-hydroxythiophene-2-carboxamide |
| I-37 | 5-{1-[({[4-(difluoromethoxy)phenyl]amino}carbonyl)amino]ethyl}-N-hydroxythiophene-2-carboxamide |
| I-38 | 5-[1-({[(3,4-dimethylphenyl)amino]carbonyl}amino)ethyl]-N-hydroxythiophene-2-carboxamide |
| I-39 | N-((1R)-1-{5-[(hydroxyamino)carbonyl]-2-thienyl}ethyl)-1-benzofuran-2-carboxamide |
| I-40 | N-hydroxy-5-[1-({[(2-methylphenyl)amino]carbonyl}amino)ethyl]thiophene-2-carboxamide |
| I-41 | N-hydroxy-5-[1-({[(3-methyl-5-phenylisoxazol-4-yl)amino]carbonyl}amino)ethyl]thiophene-2-carboxamide |
| I-42 | N-hydroxy-5-[1-({[(2-methylbenzyl)amino]carbonyl}amino)ethyl]thiophene-2-carboxamide |
| I-43 | N-hydroxy-5-((1R-1-{[(1-methylcyclohexyl)carbonyl]amino}ethyl)thiophene-2-carboxamide |
| I-44 | N-hydroxy-5-[1-({[(2-phenoxyphenyl)amino]carbonyl}amino)ethyl]thiophene-2-carboxamide |
| I-45 | N-hydroxy-5-{1-[({[4-(trifluoromethyl)phenyl]amino}carbonyl)amino]ethyl}thiophene-2-carboxamide |
| I-46 | 5-{(1R)-1-[(biphenyl-4-ylcarbonyl)amino]ethyl}-N-hydroxythiophene-2-carboxamide |
| I-47 | 5-(1-{[(2-fluorophenyl)sulfonyl]amino}ethyl)-N-hydroxythiophene-2-carboxamide |
| I-48 | N-hydroxy-5-{1-[(phenylsulfonyl)amino]ethyl}thiophene-2-carboxamide |
| I-49 | 2-(1-{[4-(benzyloxy)benzoyl]amino}ethyl)-N-hydroxy-1,3-thiazole-5-carboxamide |
| I-50 | 2-(1-{[(5-chloro-1-benzofuran-2-yl)carbonyl]amino}ethyl)-N-hydroxy-1,3-thiazole-5-carboxamide |
| I-51 | N-(1-{5-[(hydroxyamino)carbonyl]-1,3-thiazol-2-yl}ethyl)-1-methyl-1H-indole-2-carboxamide |
| I-52 | N-hydroxy-2-(1-{[(1-methyl-1H-pyrrol-2-yl)carbonyl]amino}ethyl)-1,3-thiazole-5-carboxamide |
| I-53 | 2-{1-[(2,2-dimethylpropanoyl)amino]ethyl}-N-hydroxy-1,3-thiazole-5-carboxamide |
| I-54 | 2-{1-[(1-benzothien-2-ylcarbonyl)amino]ethyl}-N-hydroxy-1,3-thiazole-5-carboxamide |
| I-55 | 2-[1-({[1-(4-chlorophenyl)cyclobutyl]carbonyl}amino)ethyl]-N-hydroxy-1,3-thiazole-5-carboxamide |
| I-56 | N-(1-{5-[(hydroxyamino)carbonyl]-3-thienyl}ethyl)-1-methylpiperidine-4-carboxamide |
| I-57 | 2-{(1S)-1-[(1-adamantylcarbonyl)amino]-2-methylpropyl}-N-hydroxy-4-(trifluoromethyl)-1,3-thiazole-5-carboxamide |
| I-58 | N-hydroxy-4-(trifluoromethyl)-2-[(1R)-1-({[4-(trifluoromethyl)phenyl]sulfonyl}amino)ethyl]-1,3-thiazole-5-carboxamide |
| I-59 | 5-((1S)-1-{[(dimethylamino)acetyl]amino}ethyl)-N-hydroxy-2-methyl-3-furamide |
| I-60 | 3-{(1S)-1-[(2,2-dimethylpropanoyl)amino]ethyl}-N-hydroxyisoxazole-5-carboxamide |
| I-61 | N-((1S)-1-{4-[(hydroxyamino)carbonyl]-5-methyl-2-furyl}ethyl)-1-methyl-1H-pyrrole-2-carboxamide |
| I-62 | 3-((1S)-1-{[(dimethylamino)acetyl]amino}ethyl)-N-hydroxyisothiazole-5-carboxamide |
| I-63 | 3-chloro-5-((1S)-1-{[(dimethylamino)acetyl]amino}ethyl)-N-hydroxythiophene-2-carboxamide |
| I-64 | 3-{(1S)-1-[(cyclopentylacetyl)amino]ethyl}-N-hydroxyisothiazole-5-carboxamide |
| I-65 | 5-((1R)-1-{[(1-adamantylamino)carbonyl]amino}butyl)-2-chloro-N-hydroxythiophene-3-carboxamide |
| I-66 | 5-{(1S)-1-[(1-adamantylcarbonyl)amino]ethyl}-3-chloro-N-hydroxythiophene-2-carboxamide |
| I-67 | N-((1S)-1-{5-[(hydroxyamino)carbonyl]-4-methyl-2-thienyl}propyl)-1-methylpiperidine-4-carboxamide |

-continued

| | |
|---|---|
| I-68 | 2-{(1S)-1-[(1-benzothien-2-ylcarbonyl)amino]ethyl}-N-hydroxy-4-methyl-1,3-oxazole-5-carboxamide |
| I-69 | 2-((1S)-1-{[(dimethylamino)acetyl]amino}-2-methylpropyl)-N-hydroxy-4-(trifluoromethyl)-1,3-thiazole-5-carboxamide |
| I-70 | N-((1S)-1-{5-chloro-4-[(hydroxyamino)carbonyl]-2-thienyl}ethyl)-1-methylpiperidine-4-carboxamide |
| I-71 | N-((1S)-1-{5-[(hydroxyamino)carbonyl]-4-methyl-2-thienyl}propyl)-1-methyl-1H-pyrrole-2-carboxamide |
| I-72 | 3-{(1S)-1-[(1-benzothien-2-ylcarbonyl)amino]ethyl}-N-hydroxyisothiazole-5-carboxamide |
| I-73 | N-((1S)-1-{5-[(hydroxyamino)carbonyl]isothiazol-3-yl}ethyl)-1-methylpiperidine-4-carboxamide |
| I-74 | 2-{(1S)-1-[(cyclopentylacetyl)amino]-2-methylpropyl}-N-hydroxy-4-(trifluoromethyl)-1,3-thiazole-5-carboxamide |
| I-75 | N-(1-{5-[(hydroxyamino)carbonyl]-3-thienyl}ethyl)-1-benzothiophene-2-carboxamide |
| I-76 | 2-{(1S)-1-[(2,2-dimethylpropanoyl)amino]ethyl}-N-hydroxy-4-methyl-1,3-oxazole-5-carboxamide |
| I-77 | 5-{(1S)-1-[(1-adamantylcarbonyl)amino]propyl}-N-hydroxy-3-methylthiophene-2-carboxamide |
| I-78 | 5-((1S)-1-{[(dimethylamino)acetyl]amino}ethyl)-N-hydroxy-1-methyl-1H-pyrrole-3-carboxamide |
| I-79 | N-((1S)-1-{5-[(hydroxyamino)carbonyl]-4-methyl-1,3-oxazol-2-yl}ethyl)-1-methyl-1H-indole-2-carboxamide |
| I-80 | 2-{(1S)-1-[(2,2-dimethylpropanoyl)amino]-2-methylpropyl}-N-hydroxy-4-(trifluoromethyl)-1,3-thiazole-5-carboxamide |
| I-81 | N-hydroxy-1-methyl-5-[(1R)-1-({[4-(trifluoromethyl)phenyl]sulfonyl}amino)ethyl]-1H-pyrrole-3-carboxamide |
| I-82 | 4-{1-[(biphenyl-4-ylcarbonyl)amino]ethyl}-N-hydroxy-2-furamide |
| I-83 | N-((1S)-1-{4-chloro-5-[(hydroxyamino)carbonyl]-2-thienyl}ethyl)-1-methylpiperidine-4-carboxamide |
| I-84 | 5-{(1S)-1-[(1-adamantylcarbonyl)amino]ethyl}-N-hydroxy-2-methyl-3-furamide |
| I-85 | 3-{(1S)-1-[(cyclopentylacetyl)amino]ethyl}-N-hydroxyisoxazole-5-carboxamide |
| I-86 | N-((1S)-1-{4-[(hydroxyamino)carbonyl]-1-methyl-1H-pyrrol-2-yl}ethyl)-1-methyl-1H-indole-2-carboxamide |
| I-87 | 4-{1-[(biphenyl-4-ylcarbonyl)amino]ethyl}-N-hydroxythiophene-2-carboxamide |
| I-88 | 2-chloro-5-{(1S)-1-[(cyclopentylacetyl)amino]ethyl}-N-hydroxythiophene-3-carboxamide |
| I-89 | 3-chloro-5-{(1S)-1-[(cyclopentylacetyl)amino]ethyl}-N-hydroxythiophene-2-carboxamide |
| I-90 | 5-{(1S)-1-[(biphenyl-4-ylcarbonyl)amino]ethyl}-N-hydroxy-1-methyl-1H-pyrrole-3-carboxamide |
| I-91 | 4-{1-[(2,2-dimethylpropanoyl)amino]ethyl}-N-hydroxy-2-furamide |
| I-92 | N-hydroxy-4-methyl-2-((1S)-1-{[(1-methyl-1H-pyrrol-2-yl)carbonyl]amino}ethyl)-1,3-oxazole-5-carboxamide |
| I-93 | N-((1S)-1-{4-[(hydroxyamino)carbonyl]-2-thienyl}-2,2-dimethylpropyl)-1-methylpiperidine-4-carboxamide |
| I-94 | N-((1S)-1-{5-[(hydroxyamino)carbonyl]isoxazol-3-yl}ethyl)-1-methylpiperidine-4-carboxamide |
| I-95 | 2-{(1S)-1-[(biphenyl-4-ylcarbonyl)amino]ethyl}-N-hydroxy-4-methyl-1,3-oxazole-5-carboxamide |
| I-96 | 2-{(1S)-1-[(biphenyl-4-ylcarbonyl)amino]-2-methylpropyl}-N-hydroxy-4-(trifluoromethyl)-1,3-thiazole-5-carboxamide |
| I-97 | 5-{(1S)-1-[(1-adamantylcarbonyl)amino]butyl}-N-hydroxy-2-furamide |
| I-98 | N-((1S)-1-{5-[(hydroxyamino)carbonyl]-2-furyl}butyl)-1-methyl-1H-indole-2-carboxamide |
| I-99 | 5-{(1S)-1-[(1-adamantylcarbonyl)amino]-2,2-dimethylpropyl}-N-hydroxythiophene-3-carboxamide |
| I-100 | 5-{(1S)-1-[(1-benzothien-2-ylcarbonyl)amino]butyl}-N-hydroxy-2-furamide |
| I-101 | N-hydroxy-4-methyl-2-[(1R)-1-({[4-(trifluoromethyl)phenyl]sulfonyl}amino)ethyl]-1,3-oxazole-5-carboxamide |
| I-102 | N-(1-{5-[(hydroxyamino)carbonyl]-3-furyl}ethyl)-1-methyl-1H-indole-2-carboxamide |
| I-103 | 2-chloro-5-{(1S)-1-[(2,2-dimethylpropanoyl)amino]ethyl}-N-hydroxythiophene-3-carboxamide |
| I-104 | 4-{1-[(cyclopentylacetyl)amino]ethyl}-N-hydroxythiophene-2-carboxamide |
| I-105 | N-hydroxy-2-((1S)-2-methyl-1-{[(1-methyl-1H-pyrrol-2-yl)carbonyl]amino}propyl)-4-(trifluoromethyl)-1,3-thiazole-5-carboxamide |
| I-106 | N-hydroxy-3-((1S)-1-{[(1-methyl-1H-pyrrol-2-yl)carbonyl]amino}ethyl)isothiazole-5-carboxamide |
| I-107 | N-((1S)-1-{4-chloro-5-[(hydroxyamino)carbonyl]-2-thienyl}ethyl)-1-methyl-1H-pyrrole-2-carboxamide |
| I-108 | 5-{(1S)-1-[(2,2-dimethylpropanoyl)amino]ethyl}-N-hydroxy-1-methyl-1H-pyrrole-3-carboxamide |
| I-109 | N-{(1S)-1-[5-[(hydroxyamino)carbonyl]-4-(trifluoromethyl)-1,3-thiazol-2-yl]-2-methylpropyl}-1-methylpiperidine-4-carboxamide |
| I-110 | 4-{1-[(2,2-dimethylpropanoyl)amino]ethyl}-N-hydroxythiophene-2-carboxamide |
| I-111 | N-(1-{5-[(hydroxyamino)carbonyl]-3-furyl}ethyl)-1-methyl-1H-pyrrole-2-carboxamide |
| I-112 | N-((1S)-1-{5-[(hydroxyamino)carbonyl]isoxazol-3-yl}ethyl)-1-methyl-1H-indole-2-carboxamide |

| | |
|---|---|
| I-113 | 5-{(1S)-1-[(biphenyl-4-ylcarbonyl)amino]butyl}-N-hydroxy-2-furamide |
| I-114 | N-((1S)-1-{5-[(hydroxyamino)carbonyl]-2-furyl}butyl)-1-methylpiperidine-4-carboxamide |
| I-115 | 3-((1R)-1-{[(1-adamantylamino)carbonyl]amino}-2-methylpropyl)-N-hydroxyisothiazole-5-carboxamide |
| I-116 | 3-((1S)-1-{[(dimethylamino)acetyl]amino}ethyl)-N-hydroxyisoxazole-5-carboxamide |
| I-117 | 2-{(1S)-1-[(cyclopentylacetyl)amino]ethyl}-N-hydroxy-4-methyl-1,3-oxazole-5-carboxamide |
| I-118 | N-((1S)-1-{5-chloro-4-[(hydroxyamino)carbonyl]-2-thienyl}ethyl)-1-methyl-1H-indole-2-carboxamide |
| I-119 | 5-{(1S)-1-[(biphenyl-4-ylcarbonyl)amino]-2,2-dimethylpropyl}-N-hydroxythiophene-3-carboxamide |
| I-120 | N-((1S)-1-{5-[(hydroxyamino)carbonyl]isothiazol-3-yl}ethyl)-1-methyl-1H-indole-2-carboxamide |
| I-121 | 4-{1-[(cyclopentylacetyl)amino]ethyl}-N-hydroxy-2-furamide |
| I-122 | 5-{(1S)-1-[(2,2-dimethylpropanoyl)amino]ethyl}-N-hydroxy-2-methyl-3-furamide |
| I-123 | 5-{(1S)-1-[(cyclopentylacetyl)amino]propyl}-N-hydroxy-3-methylthiophene-2-carboxamide |
| I-124 | 5-{(1S)-1-[(cyclopentylacetyl)amino]ethyl}-N-hydroxy-1-methyl-1H-pyrrole-3-carboxamide |
| I-125 | 3-{(1S)-1-[(2,2-dimethylpropanoyl)amino]ethyl}-N-hydroxyisothiazole-5-carboxamide |
| I-126 | 5-{(1S)-1-[(1-benzothien-2-ylcarbonyl)amino]ethyl}-N-hydroxy-1-methyl-1H-pyrrole-3-carboxamide |
| I-127 | N-((1S)-1-{5-chloro-4-[(hydroxyamino)carbonyl]-2-thienyl}ethyl)-1-methyl-1H-pyrrole-2-carboxamide |
| I-128 | 4-(1-{[(dimethylamino)acetyl]amino}ethyl)-N-hydroxy-2-furamide |
| I-129 | 5-((1S)-1-{[(dimethylamino)acetyl]amino}butyl)-N-hydroxy-2-furamide |
| I-130 | 3-((1R)-1-{[(1-adamantylamino)carbonyl]amino}ethyl)-N-hydroxyisoxazole-5-carboxamide |
| I-131 | 5-{(1S)-1-[(biphenyl-4-ylcarbonyl)amino]ethyl}-2-chloro-N-hydroxythiophene-3-carboxamide |
| I-132 | 4-{1-[(1-adamantylcarbonyl)amino]ethyl}-N-hydroxy-2-furamide |
| I-133 | 5-((1S)-1-{[(dimethylamino)acetyl]amino}propyl)-N-hydroxy-3-methylthiophene-2-carboxamide |
| I-134 | 5-{(1S)-1-[(biphenyl-4-ylcarbonyl)amino]ethyl}-3-chloro-N-hydroxythiophene-2-carboxamide |
| I-135 | 4-{1-[(1-benzothien-2-ylcarbonyl)amino]ethyl}-N-hydroxy-2-furamide |
| I-136 | 5-{(1S)-1-[(cyclopentylacetyl)amino]ethyl}-N-hydroxy-2-methyl-3-furamide |
| I-137 | 5-{(1S)-1-[(2,2-dimethylpropanoyl)amino]propyl}-N-hydroxy-3-methylthiophene-2-carboxamide |
| I-138 | N-hydroxy-5-[(1R)-1-({[4-(trifluoromethyl)phenyl]sulfonyl}amino)propyl]-2-furamide |
| I-139 | 3-{(1S)-1-[(biphenyl-4-ylcarbonyl)amino]ethyl}-N-hydroxyisothiazole-5-carboxamide |
| I-140 | 3-{(1S)-1-[(1-benzothien-2-ylcarbonyl)amino]ethyl}-N-hydroxyisoxazole-5-carboxamide |
| I-141 | 2-chloro-5-((1S)-1-{[(dimethylamino)acetyl]amino}ethyl)-N-hydroxythiophene-3-carboxamide |
| I-142 | N-((1S)-1-{4-[(hydroxyamino)carbonyl]-2-thienyl}-2,2-dimethylpropyl)-1-methyl-1H-indole-2-carboxamide |
| I-143 | N-((1S)-1-{4-[(hydroxyamino)carbonyl]-5-methyl-2-furyl}ethyl)-1-methylpiperidine-4-carboxamide |
| I-144 | 5-{(1S)-1-[(biphenyl-4-ylcarbonyl)amino]ethyl}-N-hydroxy-2-methyl-3-furamide |
| I-145 | 2-{(1S)-1-[(1-benzothien-2-ylcarbonyl)amino]-2-methylpropyl}-N-hydroxy-4-(trifluoromethyl)-1,3-thiazole-5-carboxamide |
| I-146 | N-((1S)-1-{5-[(hydroxyamino)carbonyl]-4-methyl-2-thienyl}propyl)-1-benzothiophene-2-carboxamide |
| I-147 | N-((1S)-1-{5-[(hydroxyamino)carbonyl]-4-methyl-2-thienyl}propyl)-1-methyl-1H-indole-2-carboxamide |
| I-148 | 3-{(1S)-1-[(1-adamantylcarbonyl)amino]ethyl}-N-hydroxyisoxazole-5-carboxamide |
| I-149 | 5-{(1S)-1-[(2,2-dimethylpropanoyl)amino]-2,2-dimethylpropyl}-N-hydroxythiophene-3-carboxamide |
| I-150 | 3-chloro-5-{(1S)-1-[(2,2-dimethylpropanoyl)amino]ethyl}-N-hydroxythiophene-2-carboxamide |
| I-151 | N-((1S)-1-{4-chloro-5-[(hydroxyamino)carbonyl]-2-thienyl}ethyl)-1-methyl-1H-indole-2-carboxamide |
| I-152 | 2-((1S)-1-{[(dimethylamino)acetyl]amino}ethyl)-N-hydroxy-4-methyl-1,3-oxazole-5-carboxamide |
| I-153 | 5-((1S)-1-{[(dimethylamino)acetyl]amino}-2,2-dimethylpropyl)-N-hydroxythiophene-3-carboxamide |
| I-154 | N-((1S)-1-{5-[(hydroxyamino)carbonyl]-2-furyl}butyl)-1-methyl-1H-pyrrole-2-carboxamide |
| I-155 | N-((1S)-1-{4-[(hydroxyamino)carbonyl]-1-methyl-1H-pyrrol-2-yl}ethyl)-1-methylpiperidine-4-carboxamide |
| I-156 | N-((1R)-1-{4-[(hydroxyamino)carbonyl]-1-methyl-1H-pyrrol-2-yl}ethyl)-4-methyl-2-pyridin-2-yl-1,3-thiazole-5-carboxamide |
| I-157 | N-hydroxy-3-((1R)-1-{[(1-methylcyclohexyl)carbonyl]amino}ethyl)isoxazole-5-carboxamide |
| I-158 | 3-{(1R)-1-[(biphenyl-4-ylcarbonyl)amino]ethyl}-N-hydroxyisoxazole-5-carboxamide |
| I-159 | 2-{(1S)-1-[(1-benzofuran-2-ylcarbonyl)amino]ethyl}-N-hydroxy-1,3-thiazole-5-carboxamide |

-continued

| | |
|---|---|
| I-160 | N-hydroxy-2-((1S)-1-{[(1-methyl-1H-pyrrol-2-yl)carbonyl]amino}ethyl)-1,3-thiazole-5-carboxamide |
| I-161 | 2-{(1S)-1-[(biphenyl-4-ylcarbonyl)amino]ethyl}-N-hydroxy-1,3-thiazole-5-carboxamide |
| I-162 | N-hydroxy-2-((1R)-1-{[(1-methylcyclohexyl)carbonyl]amino}ethyl)-1,3-thiazole-5-carboxamide |
| I-163 | N-hydroxy-3-((1R)-1-{[(4-methyl-2-pyridin-2-yl-1,3-thiazol-5-yl)carbonyl]amino}ethyl)isoxazole-5-carboxamide |
| I-164 | N-hydroxy-3-{(1R)-1-[(4-methoxybenzoyl)amino]ethyl}isoxazole-5-carboxamide |
| I-165 | 2-{(1R)-1-[(1-benzofuran-2-ylcarbonyl)amino]ethyl}-N-hydroxy-1,3-thiazole-5-carboxamide |
| I-166 | 2-{(1R)-1-[(2,2-dimethylpropanoyl)amino]ethyl}-N-hydroxy-1,3-thiazole-5-carboxamide |
| I-167 | N-((1R)-1-{5-[(hydroxyamino)carbonyl]-1,3-thiazol-2-yl}ethyl)-4-methyl-2-pyridin-2-yl-1,3-thiazole-5-carboxamide |
| I-168 | N-((1S)-1-{5-[(hydroxyamino)carbonyl]-1,3-thiazol-2-yl}ethyl)-4-methyl-2-pyridin-2-yl-1,3-thiazole-5-carboxamide |
| I-169 | N-hydroxy-2-{(1R)-1-[(4-methoxybenzoyl)amino]ethyl}-1,3-thiazole-5-carboxamide |
| I-170 | 3-{(1R)-1-[(1-adamantylcarbonyl)amino]ethyl}-N-hydroxyisoxazole-5-carboxamide |
| I-171 | N-hydroxy-2-((1S)-1-{[(1-methylcyclohexyl)carbonyl]amino}ethyl)-1,3-thiazole-5-carboxamide |
| I-172 | 2-((1R)-1-{[1-adamantylcarbonyl]amino}ethyl)-N-hydroxy-1,3-thiazole-5-carboxamide |
| I-173 | N-((1S)-1-{5-[(hydroxyamino)carbonyl]-1,3-thiazol-2-yl}ethyl)-1-methyl-1H-benzimidazole-2-carboxamide |
| I-174 | N-hydroxy-2-((1R)-1-{[(1-methyl-1H-pyrrol-2-yl)carbonyl]amino}ethyl)-1,3-thiazole-5-carboxamide |
| I-175 | N-hydroxy-2-{(1S)-1-[(4-methoxybenzoyl)amino]ethyl}-1,3-thiazole-5-carboxamide |
| I-176 | 3-{(1R)-1-[(1-benzothien-2-ylcarbonyl)amino]ethyl}-N-hydroxyisoxazole-5-carboxamide |
| I-177 | N-hydroxy-2-((1S)-1-{[4-(methylsulfonyl)benzoyl]amino}ethyl)-1,3-thiazole-5-carboxamide |
| I-178 | 2-{(1R)-1-[(1-benzothien-2-ylcarbonyl)amino]ethyl}-N-hydroxy-1,3-thiazole-5-carboxamide |
| I-179 | 2-((1S)-1-{[1-adamantylcarbonyl]amino}ethyl)-N-hydroxy-1,3-thiazole-5-carboxamide |
| I-180 | 2-{(1S)-1-[(1-benzothien-2-ylcarbonyl)amino]ethyl}-N-hydroxy-1,3-thiazole-5-carboxamide |
| I-181 | 3-{(1R)-1-[(1-benzofuran-2-ylcarbonyl)amino]ethyl}-N-hydroxyisoxazole-5-carboxamide |
| I-182 | 3-{(1R)-1-[(2,2-dimethylpropanoyl)amino]ethyl}-N-hydroxyisoxazole-5-carboxamide |
| I-183 | 2-{(1S)-1-[(2,2-dimethylpropanoyl)amino]ethyl}-N-hydroxy-1,3-thiazole-5-carboxamide |
| I-184 | N-hydroxy-5-[(1S)-1-({3-[(pyrrolidin-3-ylamino)carbonyl]benzyl}amino)ethyl]thiophene-2-carboxamide |
| I-185 | N-hydroxy-2-((1S)-1-{[(1-isopropylpiperidin-4-yl)methyl]amino}ethyl)-1,3-thiazole-5-carboxamide |
| I-186 | N-(4-{[((1R)-1-{5-[(hydroxyamino)carbonyl]isoxazol-3-yl}propyl)amino]methyl}pyridin-2-yl)-4-methylpiperidine-4-carboxamide |
| I-187 | N-(4-{[((1R)-1-{5-[(hydroxyamino)carbonyl]-2-thienyl}ethyl)amino]methyl}phenyl)-1-methylpiperidine-4-carboxamide |
| I-188 | 5-((1R)-1-{[(1-ethylpiperidin-4-yl)methyl]amino}ethyl)-N-hydroxythiophene-2-carboxamide |

4. General Synthetic Methods and Intermediates

The compounds of the present invention can be prepared by methods known to one of ordinary skill in the art and/or by reference to the schemes shown below and the synthetic examples. Exemplary synthetic routes are set forth in Schemes below, and in the Examples.

Scheme 1: General route to single enantiomers of substituted tert-butyl 5-(aminoalkyl)thiazole-2-carboxylates

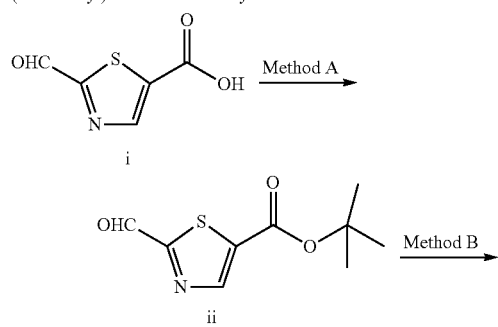
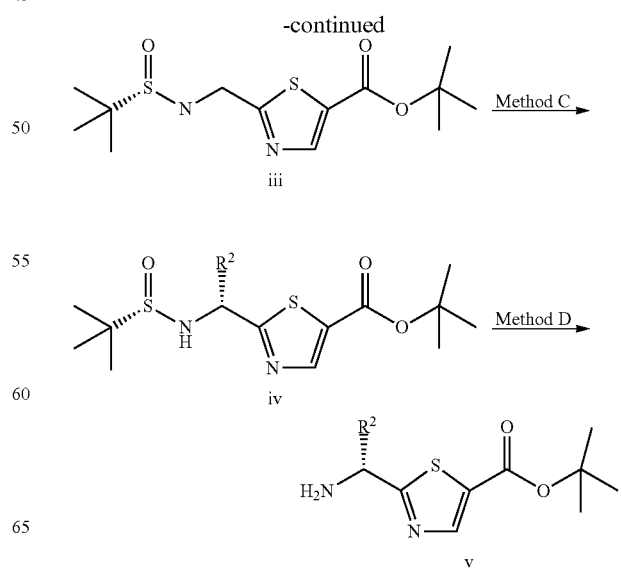

Scheme 1 shows a route for the preparation of compounds of formula v. Conversion of 2-formyl-1,3-thiazole-5-carboxylic acid i (prepared as described in WO 03/076440) to the corresponding tert-butyl ester ii can be accomplished by treatment with di-tert-butyldicarbonate in the presence of catalytic N,N-dimethylaminopyridine (Method A; WO 04/103278). Conversion to the N-(tert-butanesulfinyl)imine iii is carried out by reaction with one enantiomer of 2-methyl-2-propanesulfinamide under dehydrative conditions (Method B; Ti(OEt)$_4$ or Ti(O$^i$Pr)$_4$, DCM; Ellman et al., *Acc. Chem. Res.* 2002, 35:984; Ellman et al., *J. Org. Chem.* 1999, 64:1278; Ellman et al., *J. Am. Chem. Soc.* 1999, 121:268; Davis et al., *J. Org. Chem.* 1999, 64:1403). Diastereoselective addition of the R$^2$ group by the use of the appropriate Grignard reagent (Method C; as described by Liu et al., *J. Am. Chem. Soc.* 1997, 119:9913) provides α-branched sulfinamides iv. Isolation of single diastereomers by chromatography followed by removal of the chiral auxiliary (1 equiv. HCl; Method D) provides enantiomerically pure amine v.

FIG. 1: Examples of enantiomerically pure amines accessible via route outlined in Scheme 1

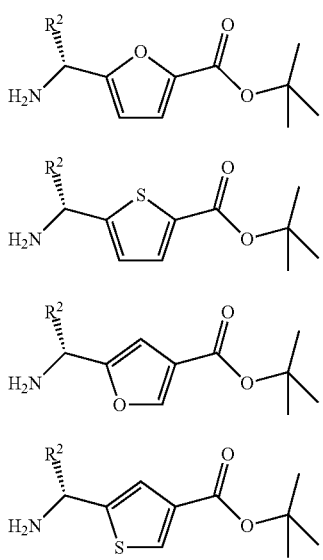

Compounds of formula vi can be prepared starting from commercially available 5-formyl-2-furoic acid. Elaboration using methods A-D as outlined in Scheme 1 provides access to enantomerically pure vi. Compounds of formula vii can be prepared starting from commercially available 5-formyl-2-thiophenecarboxylic acid. Elaboration using methods A-D as outlined in Scheme 1 provides access to enantomerically pure vii. Compounds of formula viii can be prepared starting from 5-formyl-3-furoic acid (prepared as described in WO 03/076440). Elaboration using methods A-D as outlined in Scheme 1 provides access to enantomerically pure viii. Compounds of formula ix can be prepared starting from 5-formyl-3-thiophene carboxylic acid (prepared as described in WO 03/076440). Elaboration using methods A-D as outlined in Scheme 1 provides access to enantomerically pure ix. It will be appreciated that the other optical isomer of each of the amines of formulas vi-ix will be isolated following column chromatography of the diastereomers prior to removal of the chiral auxiliary as described in Scheme 1.

Scheme 2: General route to single enantiomers of substituted ethyl-butyl 2-(aminoalkyl)oxazole-5-carboxylates.

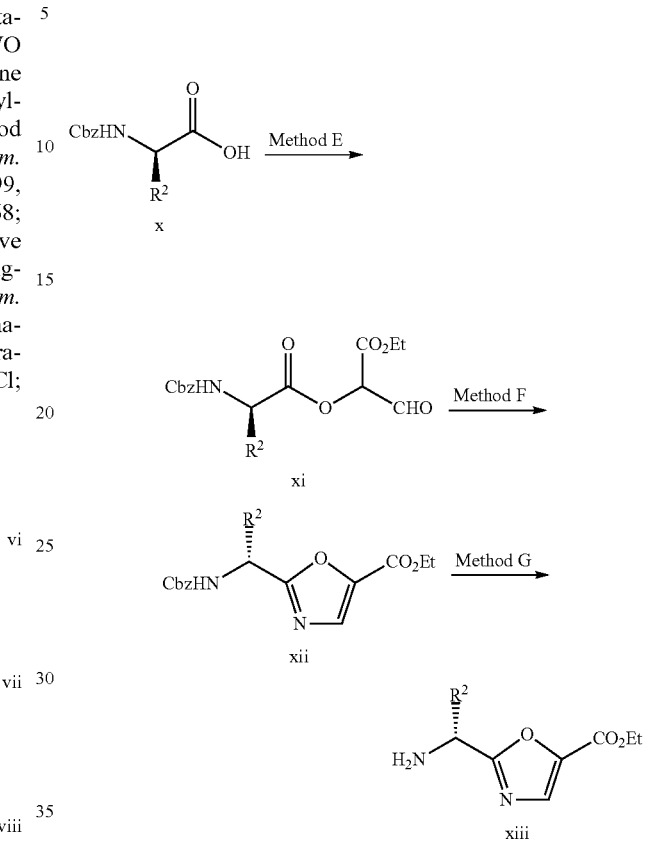

Scheme 2 shows a general route for the preparation of ethyl-(1-amino(substituted)methyl)oxazole-5-carboxylates having formula xiii. Commercially available optically pure Cbz protected α-amino acid x can be converted to xi upon treatment with ethyl-2-chloro-2-formylacetate (Method E) followed by cyclization upon heating in neat ammonium acetate (Method F) in a fashion analogous to that described by Trukhin et al., *Synlett* 2005, 13:2072-2076. Hydrogenolysis of the protecting group under an H$_2$ atmosphere over a palladium catalyst (Method G) affords the desired enantomerically pure amino ester xiii.

FIG 2:

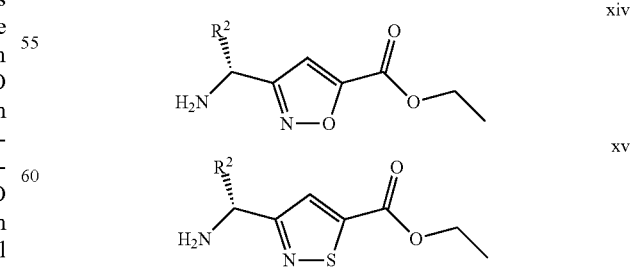

Figure 2 depicts optically pure amino esters; substituted ethyl 3-(aminomethyl)isoxazole-5-carboxylate (xiv) and substituted ethyl 3-(aminomethyl)isothiazole-5-carboxylate (xv) which can be prepared as described by Oslob et al., WO 07/058,942.

Scheme 3: General route to single enantiomers of substituted tert-butyl 5-(aminoalkyl)-1-methyl-1H-pyrrole-3-carboxylates

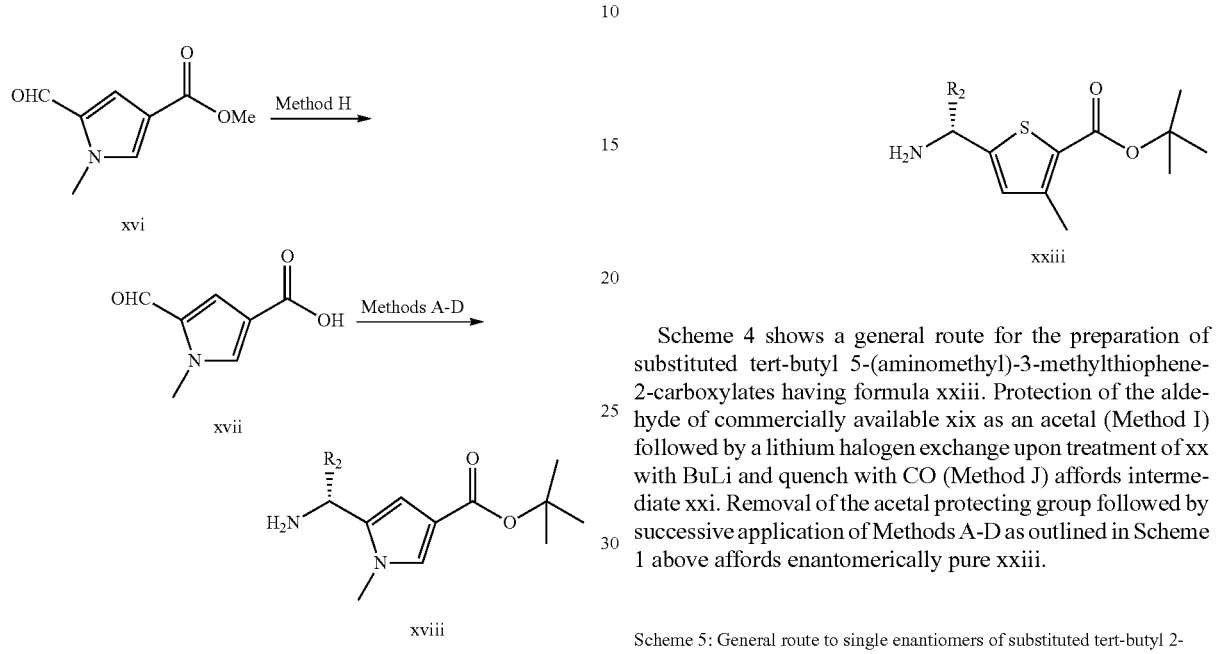

Scheme 3 shows a general route for the preparation of substituted tert-butyl 5-(aminomethyl)-1-methyl-1H-pyrrole-3-carboxylates having formula xviii. Saponification of commercially available xvi followed by methods A through D as outlined in Scheme 1 above yields the desired enantiomerically pure amino ester xviii.

Scheme 4: General route to single enantiomers of substituted tert-butyl 5-(aminoalkyl)-3-methylthiophene-2-carboxylates

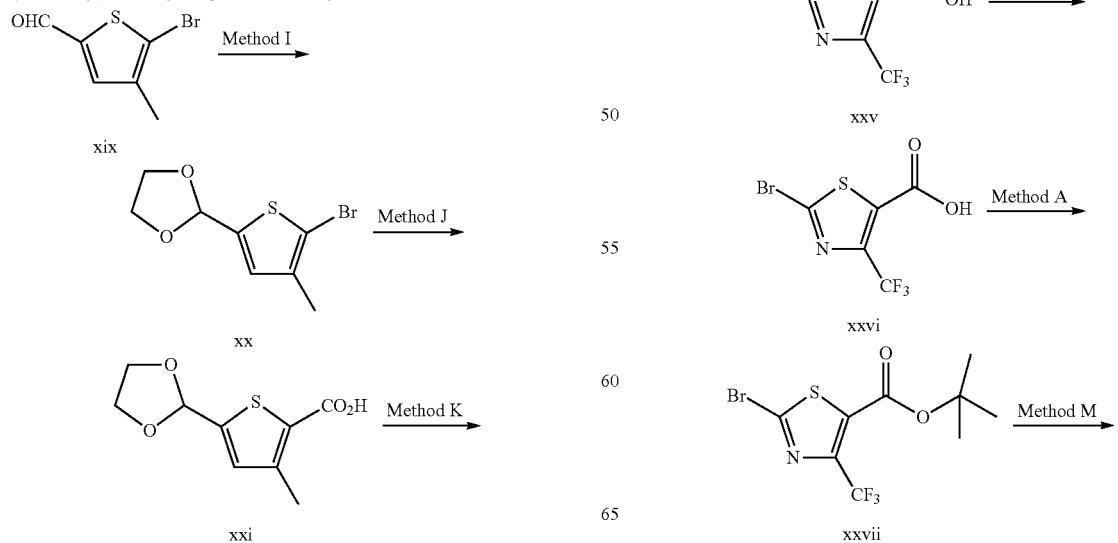

Scheme 4 shows a general route for the preparation of substituted tert-butyl 5-(aminomethyl)-3-methylthiophene-2-carboxylates having formula xxiii. Protection of the aldehyde of commercially available xix as an acetal (Method I) followed by a lithium halogen exchange upon treatment of xx with BuLi and quench with $CO_2$ (Method J) affords intermediate xxi. Removal of the acetal protecting group followed by successive application of Methods A-D as outlined in Scheme 1 above affords enantiomerically pure xxiii.

Scheme 5: General route to single enantiomers of substituted tert-butyl 2-(aminoalkyl)-4-(trifluoromethyl)thiazole-5-carboxylates

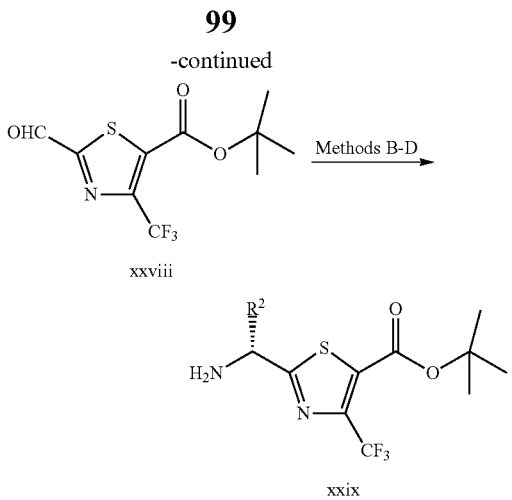

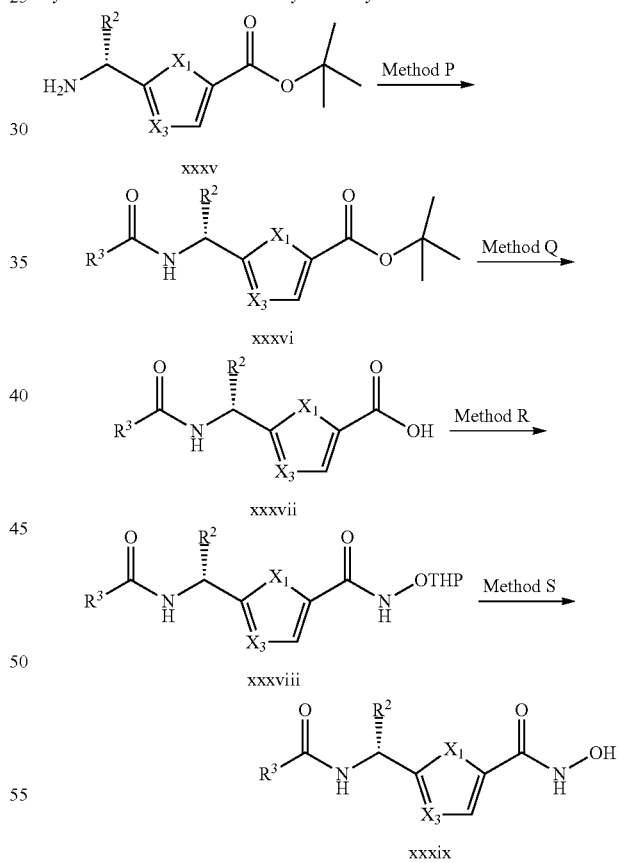

Scheme 5 shows a general route for the preparation of substituted tert-butyl 2-(aminomethyl)-4-(trifluoromethyl)thiazole-5-carboxylates having formula xxix. A Sandmeyer reaction employing t-butyl nitrite and copper bromide (as described in WO 06/085815) on xxiv (prepared as described by Park and Kim, *Tetrahedron Lett.* 1999, 40(35):6439-6442) provides the corresponding bromide of formula xxv. Saponification (Method H) followed by installation of the t-butyl ester (Method A) yields xxvii. Treatment with BuLi at reduced temperature to carry out lithium halogen exchange followed by quench with DMF (WO 06/131884) affords aldehyde xxviii. Methods B-D as outlined in Scheme 1 above provides compounds of general formula xxix.

Scheme 6: General route to single enantiomers of substituted tert-butyl 5-(aminoalkyl)-3-chlorothiophene-2-carboxylates

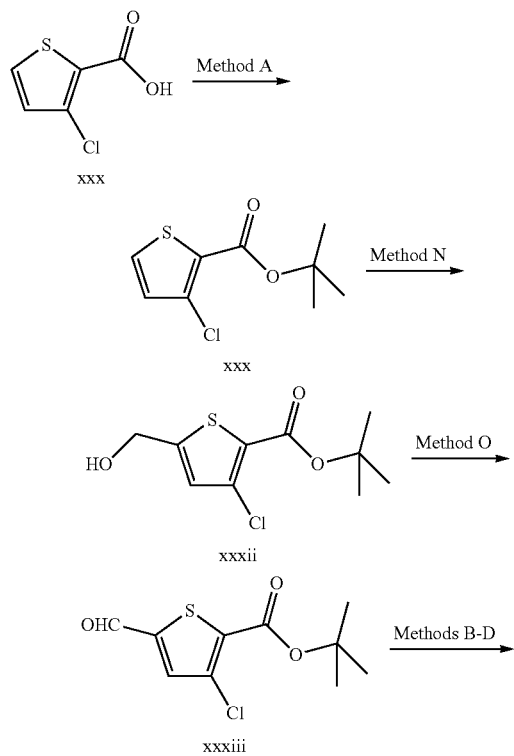

Scheme 6 shows a general route for the preparation of substituted tert-butyl 5-(aminomethyl)-3-chlorothiophene-2-carboxylate analogs. Conversion of the commercially available acid xxx to the t-butyl ester (Method A) followed by lithiation with LDA and quench with either acetaldehyde or 1,3,5-trioxane generates the corresponding primary alcohol xxxii (Method N, WO 06/086488). Subsequent oxidation using conditions such as utilized in a Swern reaction (Method O) leads to formation of the aldehyde xxxiii. Methods B-D as outlined in Scheme 1 above provides compounds of general formula xxxiv.

Scheme 7: General method for the preparation of enantiomerically pure hydroxamates derived from N-acyl heterocyclic amino acids Scheme 7 shows a general method for the preparation of enantiomerically pure hydroxamates derived from N-acyl heterocyclic amino acids. Reaction of t-butyl ester protected amino acids represented by xxxv (wherein $X_1$ and $X_3$ have the values described herein) with carboxylic acids ($R^3$—$CO_2H$) employing coupling agents such as HBTU leads to the formation of the corresponding amide xxxvi (Method P). The t-butyl ester can be removed under treatment with suitable acids such as HCl or TFA (Method Q), and the carboxylic acid xxxvii generated can be reacted with an O protected variant of hydroxylamine such as O-(tetrahydropyran-2-yl)hydroxylamine, O-(tert-butyldimethylsilyl)hydroxylamine or O-tritylhydroxylamine in the presence of an activating agent such as HATU (Method R) to provide the protected hydroxamate xxxviii. Final removal of the protecting group, for example, when O-(tetrahydropyran-2-yl)hydroxylamine is employed in Method R using acidic conditions (Method S) affords the corresponding appropriate free hydroxamic acid represented by formula xxxix.

Scheme 8: General method for the preparation of enantiomerically pure hydroxamates derived from uriedo heterocyclic amino acids

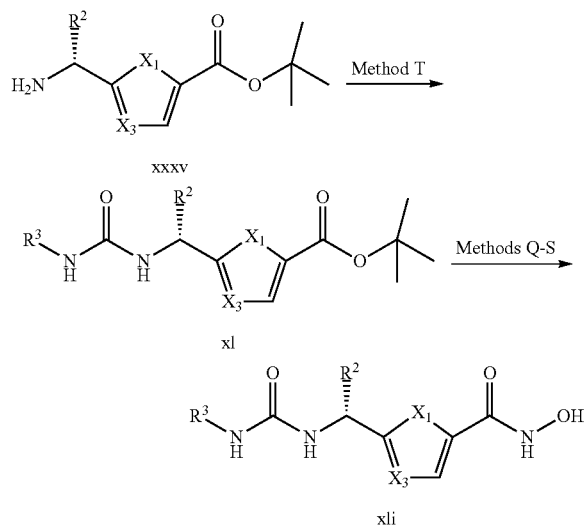

In Scheme 8, the reaction of the compounds of formula xxxv with the appropriate isocyanates (R³—NCO; Method T) leads to the formation of the corresponding urea xl. Employing an analogous reaction sequence as depicted in Scheme 7 (Methods Q-S) affords the correspond hydroxamate as represented by compound xli.

Scheme 9: General method for the preparation of enantiomerically pure hydroxamates derived from sulfonamides of heterocyclic amino acids

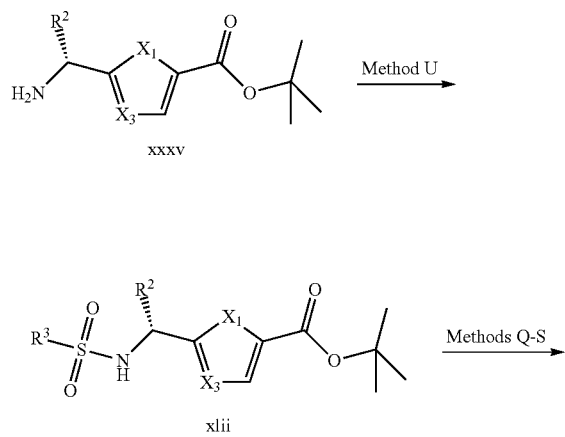

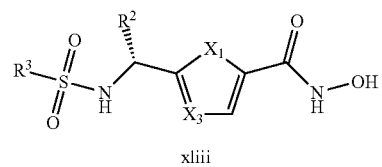

In Scheme 9, the reaction of t-butyl ester protected amino acids represented by xxxv with sulfonyl chlorides (Method U) leads to the formation of the corresponding sulfonamide xlii. Employing an analogous reaction sequence as depicted in Scheme 7 (Methods Q-S) affords the correspond hydroxamate as represented by compound xliii.

Scheme 10: General method for the preparation of (±) substituted 5-(1-aminoethyl)thiophene-2-carboxylate

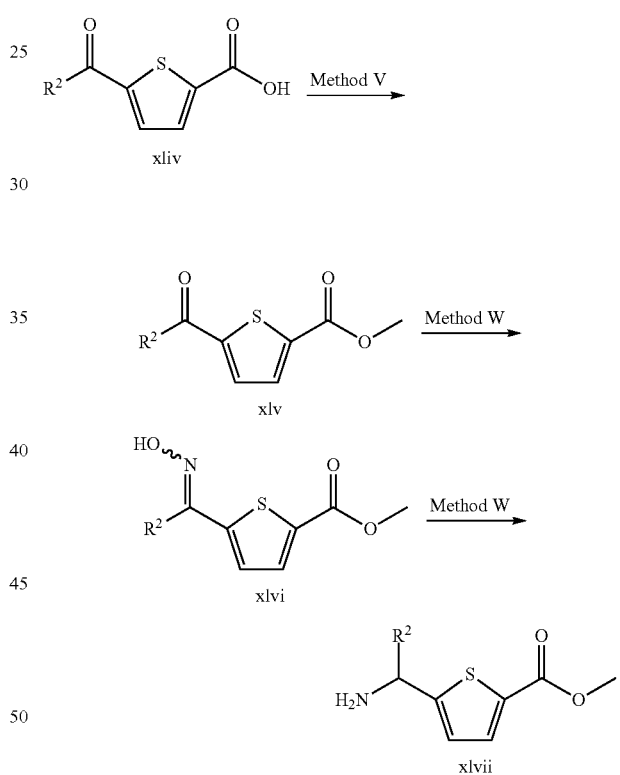

In Scheme 10, the ketone substituted thiophene-2-carboxylic acid (xliv) can be converted to the corresponding methyl ester either through treatment with diazomethane or under Fischer esterification type conditions (Method V). Condensation with hydroxylamine (Method W) affords the resulting oxime (method W) which can be reduced to generate racemic substituted methyl 5-(1-aminoethyl)thiophene-2-carboxylate (xlvii). It will be recognized that this reaction sequence can be carried out with different ketone substituents in the 5-position of the thiophene ring to generate other racemic amines.

Scheme 11: General method for the preparation of (±) substituted 2-(1-aminoalkyl)thiazole-5-carboxylates

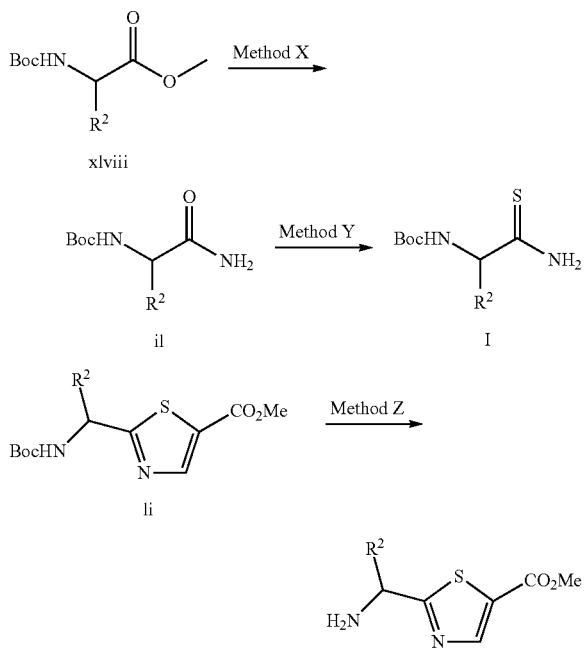

In Scheme 11, commercially available Boc protected amino acid methyl esters (xlviii) can be directly converted to the corresponding primary amide upon heating in the presence of ammonia in a sealed tube (Method X). The thioamide l is generated by the reaction of il with Lawesson's reagent (Method Y) which can be cyclized to the desired thiazole li upon condensation with ethyl 2-chloro-2-formylacetate (Method Z; Xi et al., *Bioorg. Med. Chem. Lett.* 2005, 15(23): 5211-5217).

Scheme 12: General method for the preparation of enantiomerically pure hydroxamates

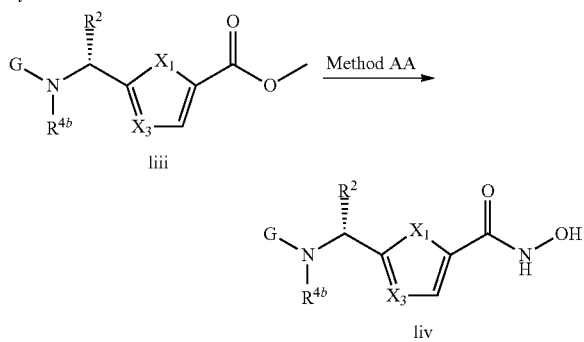

Scheme 12 shows a method for installation of the hydroxamate portion of the molecule from the appropriate heteroaromatic methyl ester liii, wherein G, $R^2$ and $R^{4b}$ have the values described herein. Reaction of liii with the potassium salt of hydroxylamine (Method AA; Huang et al., *J. Med. Chem.* 2009, 52(21):6757) leads to the formation of the corresponding hydroxamate liv.

Scheme 13: General method for the preparation of enantiomerically pure hydroxamates derived from secondary amines of heterocyclic amino acids

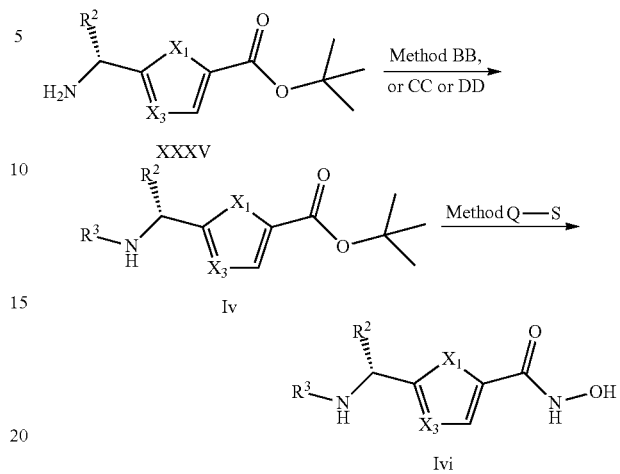

Scheme 13 shows a general route for the preparation of enantiomerically pure hydroxamates represented by formula lvi, derived from secondary amines of heterocyclic amino acids. Treatment of amine xxxv with an aldehyde under standard reductive amination conditions, such as in the presence of a borohydride such as sodium cyanoborohydride affords the secondary amine lv (Method BB). Amine xxxv may also be arylated using standard nucleophilic aromatic substitution of a suitable electrophile such as 2-chloro-nitropyridine, in the presence of suitable base, such as DIPEA at elevated temperatures (Method CC). Amine xxxv may also be N-arylated through a copper(II)-acetate mediated coupling with a suitable arylboronic acid (Method DD; Chan et al. *Tetrahedron Lett.* 1998, 39(19):2933). Employing an analogous reaction sequence as depicted in Scheme 7 (Methods Q-S) affords the correspond hydroxamate as represented by compound lvi 5. Uses, Formulation and Administration As discussed above, the present invention provides compounds and pharmaceutical compositions that are useful as inhibitors of HDAC enzymes, particularly HDAC6, and thus the present compounds are useful for treating proliferative, inflammatory, infectious, neurological or cardiovascular disorders.

The compounds and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors that can be treated with the disclosed inhibitors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

Non-limiting examples of hematologic malignancies that can be treated with the disclosed inhibitors include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, compounds of the invention are suitable for the treatment of breast cancer, lung cancer, ovarian cancer, multiple myeloma, acute myeloid leukemia or acute lymphoblastic leukemia.

In other embodiments, compounds of the invention are suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of HDAC6.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes;

oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, infectious, neurological or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, infectious, neurological or cardiovascular disorder, or is that amount effective for treating cancer. In other embodiments, an "effective amount" of a compound is an amount which inhibits binding of HDAC6, and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the method of the present invention, may be administered using any amount and any route of administration effective for treating the disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, a compound of formula (I) or a pharmaceutical composition thereof is administered in conjunction with an anticancer agent. As used herein, the term "anticancer agent" refers to any agent that is administered to a subject with cancer for purposes of treating the cancer. Combination therapy includes administration of the therapeutic agents concurrently or sequentially. Alternatively, the therapeutic agents can be combined into one composition which is administered to the patient.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which down-regulates cell replication. In certain embodiments, a compound of the invention is administered in conjunction with a proteasome inhibitor.

Another aspect of the invention relates to inhibiting HDAC6, activity in a biological sample or a patient, which method comprises administering to the patient, or contacting said biological sample with a compound of formula (I), or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where HDAC6 plays a role.

EXPERIMENTAL PROCEDURES

I. Preparation of Exemplary Compounds

Definitions

ATP adenosine triphosphate
DCE dichloroethane
DCM dichloromethane
DIPEA diisopropylethyl amine
DMF N,N-dimethylformamide
DMFDMA N,N-dimethylformamide dimethyl acetal
DMSO dimethylsulfoxide EDCI N-(3-dimethylaminopropyl)-N'-ethylcarbodiimide hydrochloride
EDTA ethylenediaminetetraacetic acid
EtOAc ethyl acetate
EtOH ethanol
FA formic acid
FBS fetal bovine serum
h hours
HATU N,N,N',N'-tetramethyl-o-(7-azabenzotriazole-1-yl) uronium hexafluorophosphate
HBTU o-benzotriazol-1-yl-N,N,N',N'-tetramethyluronium hexafluorophosphate
HEPES N-(2-Hydroxyethyl)piperazine-N'-(2-ethanesulfonic acid)
HOBT 1-hydroxybenztriazole hydrate
HRMS high resolution mass spectrum
IPA isopropyl alcohol
LAH lithium aluminum hydride
LC-MS liquid chromatography mass spectrum
m/z mass to charge
Me methyl
MEM minimum essential media
MeOH methanol
min minutes
MS mass spectrum
MWI microwave irradiation
NMM N-methyl morpholine
PBS phosphate buffered saline
rt room temperature
TEA triethylamine
TFA trifluoroacetic acid
TFAA trifluoroacetic anhydride
THF tetrahydrofuran Analytical Methods NMR: $^1$H NMR spectra are run on a 400 MHz Bruker unless otherwise stated.

LCMS: LC-MS spectra are run using an Agilent 1100 LC interfaced to a micromass Waters® Micromass® Zspray™ Mass Detector (ZMD).

HPLC: Preparative HPLC are conducted using 18×150 mm Sunfire C-18 columns eluting with water-MeCN gradients using a Gilson instrument operated by 322 pumps with the UV/visible 155 detector triggered fraction collection set to between 200 nm and 400 nm. Mass gated fraction collection is conducted on an Agilent 1100 LC/MSD instrument.

Example 1

Tert-Butyl 5-formylthiophene-2-carboxylate

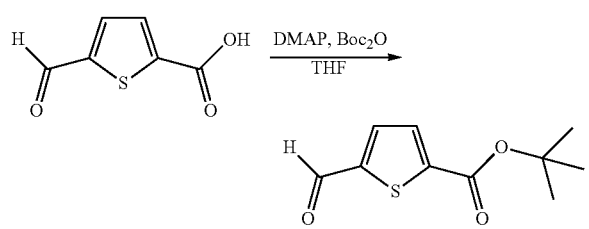

To a 100-mL round-bottom flask was added 5-formyl-2-thiophenecarboxylic acid (1.85 g, 11.8 mmol), di-tert-butyl-dicarbonate (5.69 g, 26.06 mmol), and N,N dimethylaminopyridine (0.289 g, 2.37 mmol) and THF (22 mL). The mixture was stirred at rt for 24 h. The solvent was then removed to give a solid residue to which was added EtOAc (50 mL), sat. NaHCO$_3$ solution (10 mL), and water (10 mL). After separation, the aqueous layer was extracted with EtOAc (2×50 mL). The combined organic phases were washed with brine (25 mL), dried (MgSO$_4$), and concentrated. Purification via flash chromatography (hexanes to 10% EtOAc-hexanes) afforded tert-butyl 5-formylthiophene-2-carboxylate (2.51 g, 68%) as a white solid; $^1$H NMR (CDCl$_3$, 400 MHz) δ 9.96 (s, 1H), 7.75 (d, J=3.8 Hz, 1H), 7.70 (d, J=4.0 Hz, 1H), 1.59 (s, 9H).

Example 2

(S,E)-tert-Butyl 5-((tert-butylsulfinylimino)methyl)thiophene-2-carboxylate

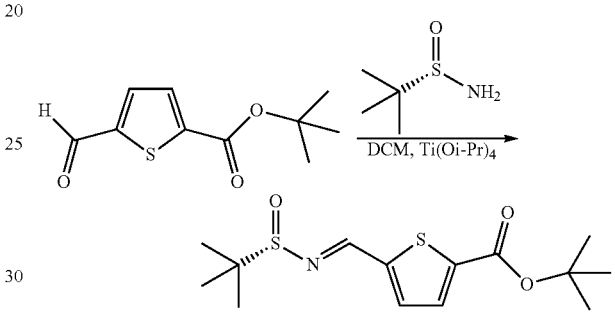

To a 500-mL round-bottom flask was added (S)-(−)-2-methyl-2-propanesulfinamide (1.62 g, 13.4 mmol), and tert-butyl 5-formylthiophene-2-carboxylate (2.37 g, 11.2 mmol), and DCM (100 mL). The mixture was cooled to 0° C., then titanium tetraisopropoxide (19.8 mL, 67.0 mmol) was added. After the solution was warmed to rt and stirred for 16 h, the reaction mixture was diluted with DCM (200 mL). To the flask was added water (19.8 mL) slowly. The mixture was vigorously stirred at rt for 30 min, then filtered through a pad of Celite. The filtrate was concentrated to give a solid. Purification via flash chromatography (hexanes to 10% EtOAc-hexanes) afforded (S,E)-tert-butyl 5-((tert-butylsulfinylimino)methyl)thiophene-2-carboxylate (3.07 g, 87%) as a white solid. $^1$H NMR (CDCl$_3$, 400 MHz) δ 8.65 (s, 1H), 7.72 (d, J=4.0 Hz, 1H), 7.65 (d, J=3.8 Hz, 1H), 1.58 (s, 9H), 1.24 (s, 9H).

Example 3

Tert-Butyl 5-[(1R)-1-{[(S)-tert-butylsulfinyl]amino}ethyl]thiophene-2-carboxylate and tert-butyl-5-[(1S)-1-{[(S)-tert-butylsulfinyl]amino}ethyl]thiophene-2-carboxylate

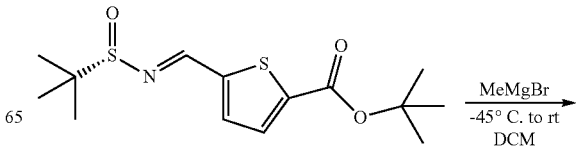

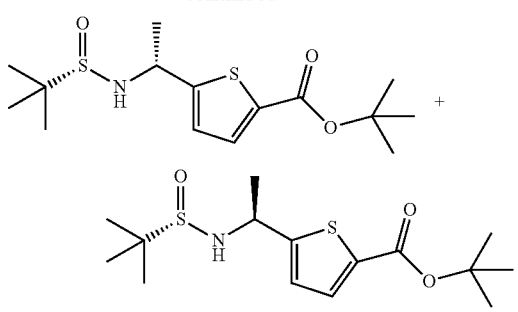

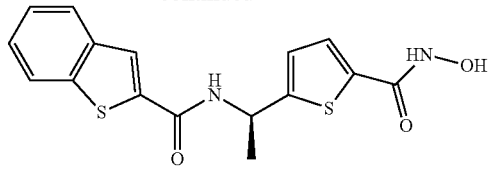

To an oven-dried 100-mL round-bottom flask was added (S,E)-tert-butyl 5-((tert-butylsulfinylimino)methyl)thiophene-2-carboxylate (1.00 g, 3.2 mmol) and DCM (15.8 mL). The solution was cooled to −45° C. under nitrogen, then methylmagnesium bromide (2.11 mL, 6.36 mmol, 3.0 M in ether) was slowly added via syringe. The resulting reaction mixture was stirred at −45° C. for 4 h, then gradually warmed to rt and stirred for 2 h. To the reaction was added DCM (50 mL) and sat. NH₄Cl solution (10 mL). After separation, the aqueous layer was extracted with DCM (2×30 mL). The combined organic layers were washed with brine, dried (MgSO₄), and concentrated. Purification via flash chromatography (20% EtOAc-hexanes to 50% EtOAc-hexanes) afforded major diastereomer tert-butyl-5-[(1R)-1-{[(S)-tert-butylsulfinyl]amino}ethyl]thiophene-2-carboxylate (0.51 g, 48%) as a white solid; $^1$H NMR (Methanol-d4, 400 MHz) δ 7.55 (d, J=3.8 Hz, 1H), 7.00 (d, J=3.8 Hz, 1H), 4.73 (q, J=6.5 Hz, 1H), 3.30 (br, 1H), 1.65 (d, J=6.8 Hz, 3H), 1.55 (s, 9H), 1.25 (s, 9H). Minor diastereomer tert-butyl-5-[(1S)-1-{[(S)-tert-butylsulfinyl]amino}ethyl]thiophene-2-carboxylate (0.061 g, 6%) was isolated as a white solid. $^1$H NMR (Methanol-d4, 400 MHz) δ 7.55 (d, J=3.5 Hz, 1H), 7.00 (d, J=3.5 Hz, 1H), 4.73 (q, J=6.8 Hz, 1H), 3.30 (br, 1H), 1.61 (d, J=6.8 Hz, 3H), 1.55 (s, 9H), 1.23 (s, 9H).

Example 4

N-((1R)-1-{5-[(hydroxyamino)carbonyl]-2-thienyl}ethyl)-1-benzothiophene-2-carboxamide
Compound I-16

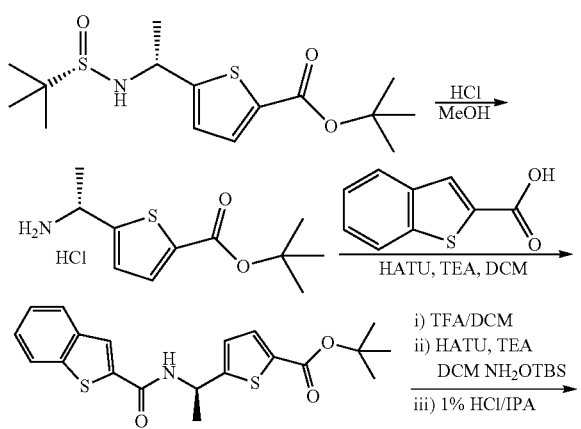

Step 1: (R)-tert-butyl 5-(1-aminoethyl)thiophene-2-carboxylate Hydrochloride

To a vial was added 5-[(1R)-1-{[(S)-tert-butylsulfinyl]amino}ethyl]thiophene-2-carboxylate (0.093 g, 0.28 mmol), hydrochloric acid (0.21 mL, 0.84 mmol, 4.0 M in 1,4-dioxane), and methanol (3 mL). The mixture was stirred at rt for 2 h. The solvent was completely removed to give (R)-tert-butyl 5-(1-aminoethyl)thiophene-2-carboxylate hydrochloride as a white solid. LC-MS: (FA) ES+ 228.

Step 2: (R)-tert-butyl 5-(1-(benzothiophene-2-carboxamido)ethyl)thiophene-2-carboxylate To a 2-dram vial was added triethylamine (0.156 mL, 1.12 mmol), HATU (0.106 g, 0.28 mmol), 1-benzothiophene-2-carboxylic acid (0.050 g, 0.28 mmol), and DCM (3 mL). The solution was stirred at rt for 30 min, then transferred to another 2-dram vial containing solid (R)-tert-butyl 5-(1-aminoethyl)thiophene-2-carboxylate hydrochloride. The mixture was stirred at rt for 16 h. To the reaction was then added DCM (3 mL) and water (1 mL). After separation, the aqueous layer was extracted with DCM (2×3 mL). The combined organic phases were evaporated to dryness to give (R)-tert-butyl 5-(1-(benzothiophene-2-carboxamido)ethyl)thiophene-2-carboxylate as a brown solid. LC-MS: (FA) ES+ 388.

Step 3: N-((1R)-1-{5-[(hydroxyamino)carbonyl]-2-thienyl}ethyl)-1-benzothiophene-2-carboxamide To the vial containing crude (R)-tert-butyl 5-(1-(benzothiophene-2-carboxamido)ethyl)thiophene-2-carboxylate from Step 2 was added DCM (4 mL) and trifluoroacetic acid (0.43 mL, 5.6 mmol). The mixture was stirred at rt for 16 h and then completely evaporated to give an oil residue. To the residue was added HATU (0.160 g, 0.42 mmol), triethylamine (0.39 mL, 2.80 mmol), and DCM (4 mL). After stirring at rt for 30 min, O-(tert-butyldimethylsilyl)hydroxylamine (0.083 g, 0.56 mmol) was added. The mixture was stirred at rt for 2 h then the solvent was completely removed to give a sticky brown oil. To this oil residue was added hydrochloric acid (6.0 mL, 1% v/v in IPA). After stirring at rt for 30 min, the mixture was evaporated to dryness to give a solid to which was added DMSO (1.1 mL). The solution was filtered and purified by Gilson prep-HPLC [25-50% MeCN—H₂O] to give the title compound (0.0098 g, 10.1%) as a white solid. LC-MS: (FA) ES+ 347; $^1$H NMR (Methanol-d₄, 400

MHz) δ 8.00 (s, 1H), 7.89 (m, 2H), 7.42 (m, 3H), 7.06 (d, J=4.0 Hz, 1H), 5.51 (q, J=7.5 Hz, 1H), 1.69 (d, J=7.0 Hz, 3H).

Example 5

N-hydroxy-5-((1R)-1-{[(1-methylcyclohexyl)carbonyl]amino}ethyl)thiophene-2-carboxamide Compound I-43

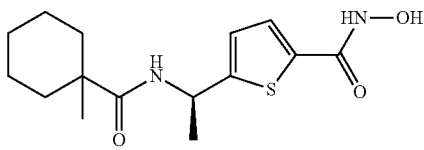 [SMILES: C[C@@H](NC(=O)C1(C)CCCCC1)c1ccc(C(=O)NO)s1]

The title compound was prepared in an analogous fashion to that described in Example 4 starting from tert-butyl 5-[(1R)-1-{[(S)-tert-butylsulfinyl]amino}ethyl]thiophene-2-carboxylate. LC-MS: (FA) ES+ 311.

Example 6

N-((1R)-1-{5-[(hydroxyamino)carbonyl]-2-thienyl}ethyl)-1-benzofuran-2-carboxamide Compound I-39

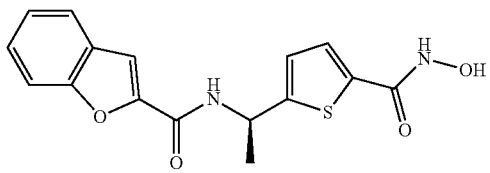 [SMILES: C[C@@H](NC(=O)c1cc2ccccc2o1)c1ccc(C(=O)NO)s1]

The title compound was prepared in an analogous fashion to that described in Example 4 starting from tert-butyl 5-[(1R)-1-{[(S)-tert-butylsulfinyl]amino}ethyl]thiophene-2-carboxylate. LC-MS: (FA) ES+ 331.

Example 7

N-((1R)-1-{5-[(hydroxyamino)carbonyl]-2-thienyl}ethyl)-3-methyl-1-benzothiophene-2-carboxamide Compound I-31

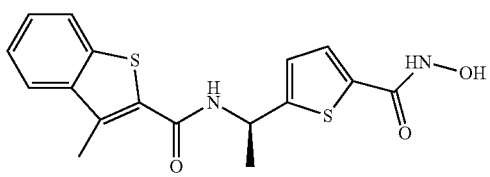 [SMILES: Cc1c(C(=O)N[C@H](C)c2ccc(C(=O)NO)s2)sc2ccccc12]

The title compound was prepared in an analogous fashion to that described in Example 4 starting from tert-butyl 5-[(1R)-1-{[(S)-tert-butylsulfinyl]amino}ethyl]thiophene-2-carboxylate. LC-MS: (FA) ES+ 361.

Example 8

5-{(1R)-1-[(biphenyl-4-ylcarbonyl)amino]ethyl}-N-hydroxythiophene-2-carboxamide Compound I-46

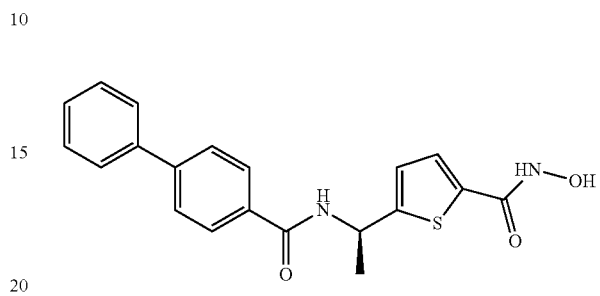

The title compound was prepared in an analogous fashion to that described in Example 4 starting from tert-butyl 5-[(1R)-1-{[(S)-tert-butylsulfinyl]amino}ethyl]thiophene-2-carboxylate. LC-MS: (FA) ES+ 367.

Example 9

N-((1R)-1-{5-[(hydroxyamino)carbonyl]-2-thienyl}ethyl)-1-methyl-1H-pyrrole-2-carboxamide Compound I-29

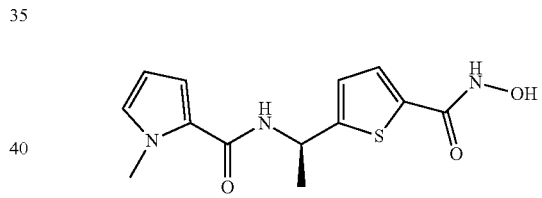

The title compound was prepared in an analogous fashion to that described in Example 4 starting from tert-butyl 5-[(1R)-1-{[(S)-tert-butylsulfinyl]amino}ethyl]thiophene-2-carboxylate. LC-MS: (FA) ES+ 294.

Example 10

5-{(1R)-1-[(1-adamantylcarbonyl)amino]ethyl}-N-hydroxythiophene-2-carboxamide Compound I-11

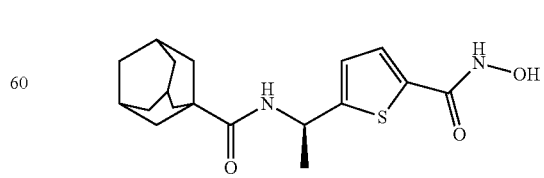

The title compound was prepared in an analogous fashion to that described in Example 4 starting from tert-butyl 5-[(1R)-1-{[(S)-tert-butylsulfinyl]amino}ethyl]thiophene-2-carboxylate. LC-MS: (FA) ES+ 349.

Example 11

N-hydroxy-5-{(1R)-1-[(4-methoxybenzoyl)amino]ethyl}thiophene-2-carboxamide Compound I-9

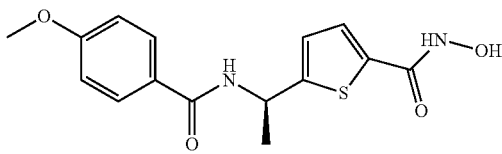 [SMILES: COc1ccc(C(=O)N[C@H](C)c2ccc(C(=O)NO)s2)cc1]

The title compound was prepared in an analogous fashion to that described in Example 4 starting from tert-butyl 5-[(1R)-1-{[(S)-tert-butylsulfinyl]amino}ethyl]thiophene-2-carboxylate. LC-MS: (FA) ES+ 321.

Example 12

4,5-dichloro-N-((1R)-1-{5-[(hydroxyamino)carbonyl]-2-thienyl}ethyl)-1-methyl-1H-pyrrole-2-carboxamide Compound I-17

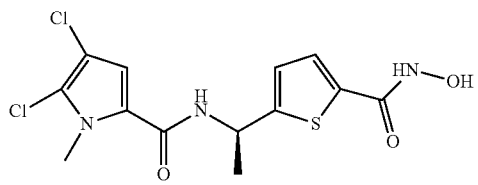 [SMILES: C[C@@H](NC(=O)c1cc(Cl)c(Cl)n1C)c1ccc(C(=O)NO)s1]

The title compound was prepared in an analogous fashion to that described in Example 4 starting from tert-butyl 5-[(1R)-1-{[(S)-tert-butylsulfinyl]amino}ethyl]thiophene-2-carboxylate. LC-MS: (FA) ES+ 363.

Example 13

N-((1R)-1-{5-[(hydroxyamino)carbonyl]-2-thienyl}ethyl)-3-methyl-1-benzofuran-2-carboxamide Compound I-15

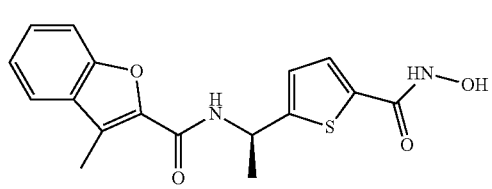 [SMILES: Cc1c(C(=O)N[C@H](C)c2ccc(C(=O)NO)s2)oc2ccccc12]

The title compound was prepared in an analogous fashion to that described in Example 4 starting from tert-butyl 5-[(1R)-1-{[(S)-tert-butylsulfinyl]amino}ethyl]thiophene-2-carboxylate. LC-MS: (FA) ES+ 345.

Example 14

5-{(1R)-1-[(2,2-dimethylpropanoyl)amino]ethyl}-N-hydroxythiophene-2-carboxamide Compound I-5

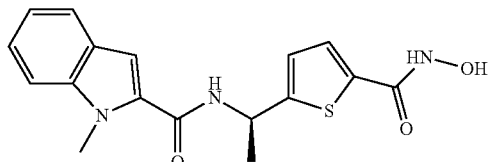

The title compound was prepared in an analogous fashion to that described in Example 4 starting from tert-butyl 5-[(1R)-1-{[(S)-tert-butylsulfinyl]amino}ethyl]thiophene-2-carboxylate. LC-MS: (FA) ES+ 344.

Example 15

5-{(1R)-1-[(2,2-dimethylpropanoyl)amino]ethyl}-N-hydroxythiophene-2-carboxamide Compound I-6

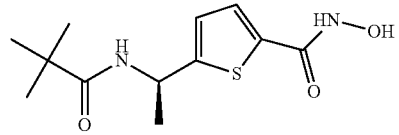 [SMILES: C[C@@H](NC(=O)C(C)(C)C)c1ccc(C(=O)NO)s1]

The title compound was prepared in an analogous fashion to that described in Example 4 starting from tert-butyl 5-[(1R)-1-{[(S)-tert-butylsulfinyl]amino}ethyl]thiophene-2-carboxylate. LC-MS: (FA) ES+ 271.

Example 16

N-((1S)-1-{5-[(hydroxyamino)carbonyl]-2-thienyl}ethyl)-1-benzothiophene-2-carboxamide Compound I-21

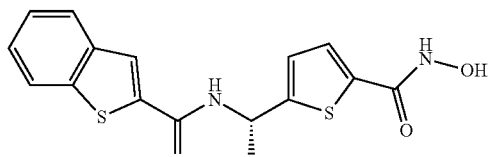

The title compound was prepared in an analogous fashion to that described in Example 4 starting from tert-butyl 5-[(1S)-1-{[(S)-tert-butylsulfinyl]amino}ethyl]thiophene-2-carboxylate. Yield: 18.0%; LC-MS: (FA) ES+ 347; $^1$H NMR (Methanol-d$_4$, 400 MHz) δ 8.00 (s, 1H), 7.89 (m, 2H), 7.42 (m, 3H), 7.06 (d, J=4.0 Hz, 1H), 5.51 (q, J=7.5 Hz, 1H), 1.69 (d, J=7.0 Hz, 3H).

Example 17

N-hydroxy-5-[(1R)-1-({[4-(trifluoromethyl)phenyl]sulfonyl}amino)ethyl]thiophene-2-carboxamide Compound I-23

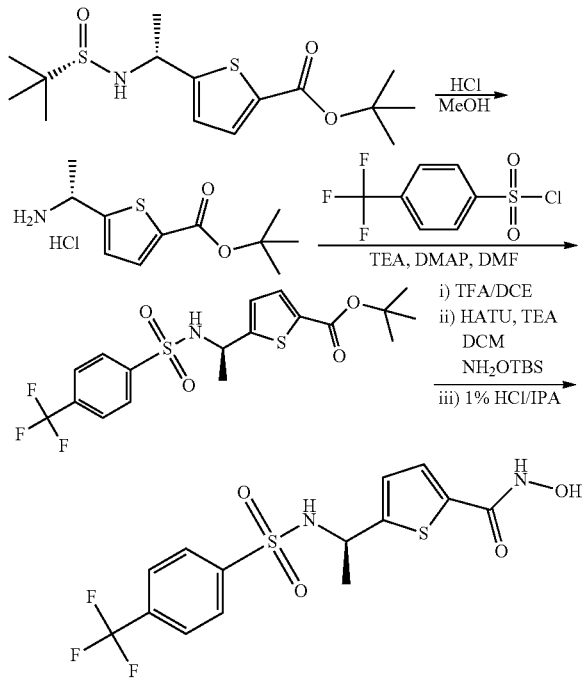

Step 1: (R)-tert-butyl 5-(1-aminoethyl)thiophene-2-carboxylate Hydrochloride To a vial containing 5-[(1R)-1-{[(S)-tert-butylsulfinyl]amino}ethyl]thiophene-2-carboxylate (0.053 g, 0.16 mmol) was added hydrochloric acid (0.080 mL, 0.320 mmol, 4.0 M of in 1,4-dioxane), and methanol (2 mL). This mixture was stirred at rt for 2 h, then evaporated to dryness to afford (R)-tert-butyl 5-(1-aminoethyl)thiophene-2-carboxylate hydrochloride as a white solid. LC-MS: (FA) ES+ 228.

Step 2: (R)-tert-butyl 5-(1-(4-(trifluoromethyl)phenylsulfonamido)ethyl)thiophene-2-carboxylate To the vial containing (R)-tert-butyl 5-(1-aminoethyl)thiophene-2-carboxylate hydrochloride from Step 1 was added N,N-dimethylaminopyridine (3.91 mg, 0.0320 mmol), 4-(trifluoromethyl)benzenesulfonyl chloride (0.059 g, 0.24 mmol), N,N-dimethylformamide (2 mL), and triethylamine (0.178 mL, 1.28 mmol). The mixture was stirred at rt for 16 h and then evaporated. To the residue was added 1,2-dichloroethane (3 mL), sat. NaHCO$_3$ solution (0.5 mL), and water (0.5 mL). After separation, the aqueous layer was extracted with 1,2-dichloroethane (2×3 mL). The combined organic phases were evaporated to dryness to give crude (R)-tert-butyl 5-(1-(4-(trifluoromethyl)phenylsulfonamido)ethyl)thiophene-2-carboxylate as a brown solid. LC-MS: (FA) ES– 434.

Step 3: N-hydroxy-5-[(1R)-1-({[4-(trifluoromethyl)phenyl]sulfonyl}amino)ethyl]thiophene-2-carboxamide To a 2-dram vial containing crude (R)-tert-butyl 5-(1-(4-(trifluoromethyl)phenylsulfonamido)ethyl)thiophene-2-carboxylate from Step 2 was added 1,2-dichloroethane (2 mL), and trifluoroacetic acid (0.246 mL, 3.20 mmol). After shaking at rt for 4 h, the mixture was evaporated to dryness to give a solid which was azeotroped with toluene (2×5 mL). To the resulting solid residue in another microwave vial was added HATU (0.0912 g, 0.240 mmol), N,N-dimethylformamide (1.5 mL), and triethylamine (0.178 mL, 1.28 mmol). The mixture was stirred for 10 min then O-(tert-butyldimethylsilyl)hydroxylamine (0.0471 g, 0.320 mmol) in DCM (0.5 mL) was added. The solution was shaken at rt for 2 h and then evaporated to dryness to afford a brown oil. To this oil in a microwave vial was added hydrochloric acid (3.5 mL, 1% in IPA). After shaking at rt for 30 min, solid NaHCO$_3$ was added to quench the excess acid and the solvent was then removed. To the resulting solid residue was added DMSO (1.2 mL). After filtration, the DMSO solution was filtered and purified by Gilson prep-HPLC to give the title compound (0.0148 g, 23%) as a white solid. LC-MS: (FA) ES– 393. $^1$H NMR (Methanol-d$_4$, 300 MHz) δ 7.92 (d, J=8.3 Hz, 2H), 7.76 (d, J=8.3 Hz, 2H), 7.24 (m, 1H), 6.77 (d, J=4.1 Hz, 1H), 4.78 (q, J=7.0 Hz, 1H), 1.44 (d, J=6.8 Hz, 3H).

Example 18

5-((1R)-1-{[(tert-butylamino)carbonyl]amino}ethyl)-N-hydroxythiophene-2-carboxamide Compound I-8

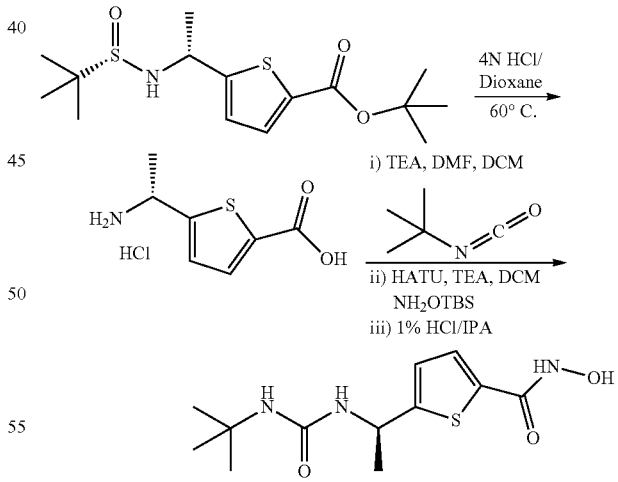

Step 1: (R)-5-(1-aminoethyl)thiophene-2-carboxylic Acid Hydrochloride

To a vial containing 5-[(1R)-1-{[(S)-tert-butylsulfinyl]amino}ethyl]thiophene-2-carboxylate (0.050 g, 0.15 mmol) was added hydrochloric acid (3 mL, 12.0 mmol, 4.0 M of in 1,4-dioxane). This mixture was capped and heated at 60° C. for 2 h, after which it was evaporated to dryness to afford (R)-5-(1-aminoethyl)thiophene-2-carboxylic acid hydrochloride as a white solid. LC-MS: (FA) ES+ 172.

Step 2: 5-((1R)-1-{[(tert-butylamino)carbonyl]amino}ethyl)-N-hydroxythiophene-2-carboxamide To the vial containing (R)-4-(1-aminoethyl)benzoic acid hydrochloride from Step 1 was added tert-butyl isocyanate (0.026 mL, 0.23 mmol), N,N dimethylformamide (2.5 mL) and triethylamine (0.21 mL, 1.50 mmol). After the reaction was stirred at rt for 16 h, HATU (0.057 g, 0.150 mmol) in N,N-dimethylformamide (0.5 mL) was added, immediately followed by the addition of O-(tert-butyldimethylsilyl)hydroxylamine (0.0331 g, 0.225 mmol) in DCM (1.0 mL). This mixture was shaken at rt for 1 hr after which it was evaporated to dryness. To the resulting residue was added hydrochloric acid (4 mL, 1% in IPA). After shaking at rt for 30 min, solid NaHCO$_3$ was added to quench excess acid and the solvent was then completely evaporated to dryness to give a solid residue. This solid was dissolved in DMSO (1.2 mL), and the solution was filtered and purified via Gilson prep-HPLC to give the title compound (0.015 g, 35%) as a white solid. LC-MS: (FA) ES+ 286; $^1$H NMR (Methanol-d$_4$, 300 MHz) δ 7.41 (m, 1H), 6.91 (d, J=4.7 Hz, 1H), 5.03 (q, J=6.8 Hz, 1H), 2.03 (m, 4H), 1.96 (m, 8H), 1.69 (m, 8H), 1.47 (d, J=7.0 Hz, 3H).

Example 19

5-[(1R)-1-({[1-adamantylamino]carbonyl}amino)ethyl]-N-hydroxythiophene-2-carboxamide Compound I-26

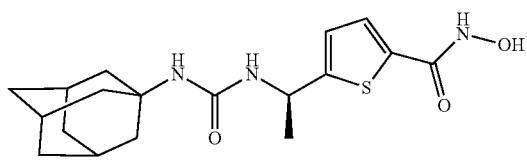 [SMILES: C[C@@H](NC(=O)NC12CC3CC(CC(C3)C1)C2)c1ccc(C(=O)NO)s1]

The title compound was prepared in an analogous fashion to that described in Example 18 starting from tert-butyl 3-[(1R)-1-{[(S)-tert-butylsulfinyl]amino}-2-methylpropyl]benzoate. LC-MS: (FA) ES+ 349; $^1$H NMR (Methanol-d$_4$, 300 MHz) δ 7.41 (m, 1H), 6.92 (d, J=3.8 Hz, 1H), 5.04 (q, J=6.4 Hz, 1H 1.47 (d, J=7.0 Hz, 3H), 1.29 (s, 9H).

Example 20

Methyl 5-(1-aminoethyl)thiophene-2-carboxylate

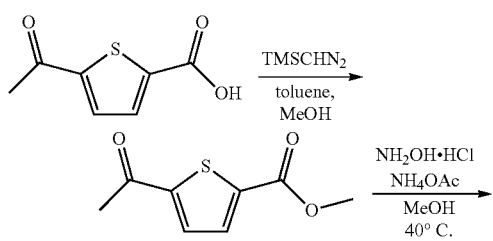

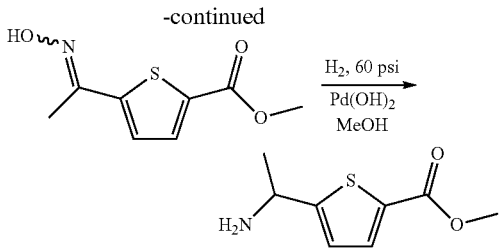

Step 1: Methyl 5-acetylthiophene-2-carboxylate

To a solution of 5-acetylthiophene-2-carboxylic acid (3.24 g, 19.0 mmol) dissolved in a mixture of toluene (50 mL) and methanol (50 mL) cooled to 0° C. was added 2.0 M trimethylsilyldiazomethane in ether (19.0 mL, 38.1 mmol) dropwise. Upon complete addition, the reaction mixture was allowed to warm to room temperature overnight. The reaction was quenched with the addition of acetic acid and the solvent was removed. The residue thus obtained was partitioned between ethyl acetate and saturated aqueous NaHCO$_3$ and upon separation, the organic layer was dried over anhydrous magnesium sulfate and concentrated to afford the desired product (3.49 g, 100%). LC-MS: (FA) ES+ 185)

Step 2: Methyl 5-1-N-(hydroxyimino)ethyl)thiophene-2-carboxylate

A solution of methyl 5-acetylthiophene-2-carboxylate from Step 1 (3.49 g, 18.9 mmol), hydroxylamine hydrochloride (10.53 g, 151.6 mmol) and sodium acetate (12.43 g, 151.6 mmol) in methanol (250 mL) was heated at 40° C. for 2 hours. The solvent was completely removed and the residue obtained was partitioned between EtOAc (50 mL) and water (30 mL). The organic layer was further washed with brine (20 mL), dried over anhydrous magnesium sulfate and concentrated to afford a white powder (3.43 g, 91%). LC-MS: (FA) ES+ 200).

Step 3: Methyl 5-(1-aminoethyl)thiophene-2-carboxylate Hydrochloride

To a degassed solution of methyl 5-[(1E)-N-hydroxyethanimidoyl]thiophene-2-carboxylate (3.43 mg, 17.2 mmol) and hydrochloric acid (12.0 M, 1.8 mL, 22.4 mmol) in methanol (100 mL) was added Pearlman's catalyst (84.6 mg, 0.2 mmol). The resulting reaction mixture was shaken under a 60 psi atmosphere of H$_2$ for 4 days. The catalyst was removed by filtration through celite and the solvent was removed to afford a white solid (3.55 g, 93%). LC-MS: (FA) ES+ 186)

Example 21

5-(1-(3-cyclopentylureido)ethyl)-N-hydroxythiophene-2-carboxamide Compound I-1

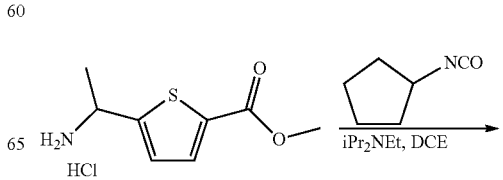

123

-continued

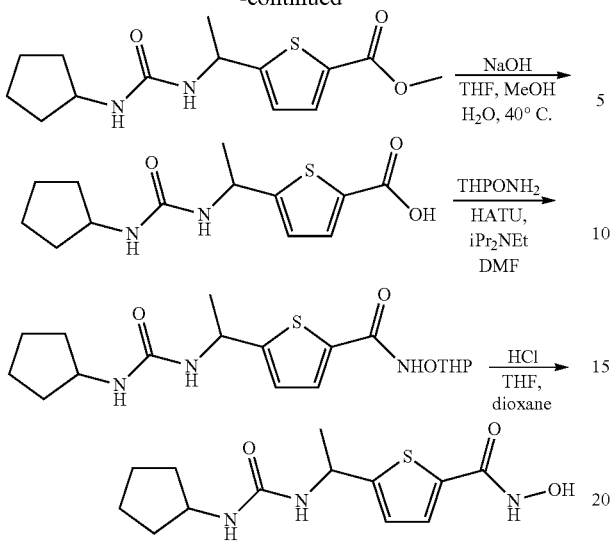

Step 1: Methyl 5-(1-(3-cyclopentylureido)ethyl)thiophene-2-carboxylate

To a solution of methyl 5-(1-aminoethyl)thiophene-2-carboxylate hydrochloride (33.2 mg, 0.150 mmol) and N,N-diisopropylethylamine (104 μL, 0.60 mmol) dissolved in 1,2-dichloroethane (1 mL) was added isocyanatocyclopentane (24 mg, 0.22 mmol). The reaction solution was shaken at room temperature overnight. The solution was further diluted with DCE (2 mL) and washed with saturated aqueous NaHCO₃ (2 mL). The layers were separated and the organic layer concentrated to afford methyl 5-(1-(3-cyclopentylureido)ethyl)thiophene-2-carboxylate as an oil residue. LC-MS: (FA) ES+ 297.

Step 2: 5-(1-(3-cyclopentylureido)ethyl)thiophene-2-carboxylic Acid

To a solution of methyl 5-(1-(3-cyclopentylureido)ethyl)thiophene-2-carboxylate obtained from step 1 in tetrahydrofuran (1 mL) and methanol (0.5 mL) was added 1.0 M aqueous NaOH (0.5 mL) and the reaction solution was heated to 40° C. for 8 hours. The reaction was neutralized with the addition of 1M aqueous HCl (0.5 mL) and the solution was evaporated to dryness to afford 5-(1-(3-cyclopentylureido)ethyl)thiophene-2-carboxylic acid. LC-MS: (FA) ES+ 283.

Step 3: 5-(1-(3-cyclopentylureido)ethyl)-N-(tetrahydro-2H-pyran-2-yloxy)thiophene-2-carboxamide To a mixture of 5-(1-(3-cyclopentylureido)ethyl)thiophene-2-carboxylic acid obtained in step 2 in DMF (1 mL) was added HATU (62 mg, 0.165 mmol) and N,N-diisopropylethylamine (130 μL, 0.75 mmol) was added a solution of O-(tetrahydropyran-2-yl)hydroxylamine (19.3 mg, 0.165 mmol) in N,N-dimethylformamide (1.0 mL). The reaction was stirred at room temperature for 12 hours. The solution was evaporated to dryness and to the residue was added 1,2-dichloroethane (3 mL), sat. NaHCO₃ solution (0.5 mL), and water (0.5 mL). After separation, the aqueous layer was extracted with 1,2-dichloroethane (2×3 mL). The combined organic phases were evaporated to dryness to give crude 5-(1-(3-cyclopentylureido)ethyl)-N-(tetrahydro-2H-pyran-2-yloxy)thiophene-2-carboxamide. LC-MS: (FA) ES+ 382.

Step 4: 5-(1-(3-cyclopentylureido)ethyl)-N-hydroxythiophene-2-carboxamide

To a solution of 5-(1-(3-cyclopentylureido)ethyl)-N-(tetrahydro-2H-pyran-2-yloxy)thiophene-2-carboxamide obtained in step 3 was dissolved in THF (1 mL) was added 4.0 M HCl in dioxane (0.25 mL). The reaction was stirred for 4 hours at room temperature, evaporated to dryness, redissolved in DMSO (1 mL) and purified on Agilent 1100 LC/MSD instrument to afford the title compounds as a white solid (2.7 mg, 16%) LC-MS: (FA) ES+ 298.

Example 22

N-hydroxy-5-[(1R)-1-({[4-(trifluoromethyl)phenyl]sulfonyl}amino)ethyl]thiophene-2-carboxamide Compound I-23

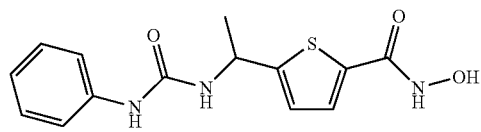 [SMILES: CC(NC(=O)Nc1ccccc1)c1ccc(C(=O)NO)s1]

The title compound was prepared in an analogous fashion to that described in Example 21 using phenyl isocyanate. LC-MS: (FA) ES+ 306.

Example 23

5-(1-{[(benzylamino)carbonyl]amino}ethyl)-N-hydroxythiophene-2-carboxamide Compound I-18

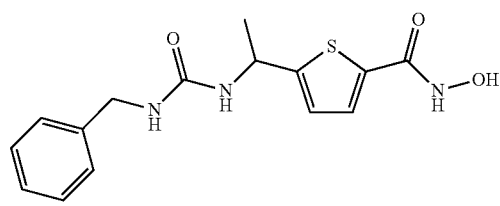 [SMILES: CC(NC(=O)NCc1ccccc1)c1ccc(C(=O)NO)s1]

The title compound was prepared in an analogous fashion to that described in Example 21 using benzyl isocyanate. LC-MS: (FA) ES+ 320.

Example 24

5-(1-{[(cyclohexylamino)carbonyl]amino}ethyl)-N-hydroxythiophene-2-carboxamide Compound I-24

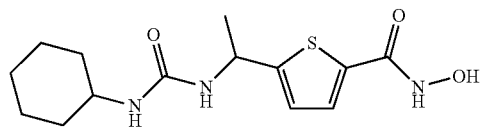 [SMILES: CC(NC(=O)NC1CCCCC1)c1ccc(C(=O)NO)s1]

The title compound was prepared in an analogous fashion to that described in Example 21 using cyclohexyl isocyanate. LC-MS: (FA) ES+ 312.

Example 25

N-hydroxy-5-[1-({[(2-methylphenyl)amino]carbonyl}amino)ethyl]thiophene-2-carboxamide Compound I-40

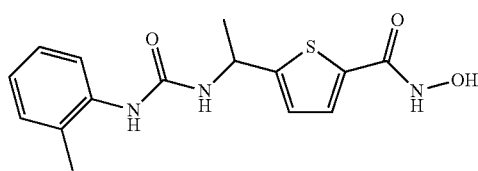 [SMILES: Cc1ccccc1NC(=O)NC(C)c1ccc(C(=O)NO)s1]

The title compound was prepared in an analogous fashion to that described in Example 21 using o-tolyl isocyanate. LC-MS: (FA) ES+ 320.

Example 26

5-(1-{[(tert-butylamino)carbonyl]amino}ethyl)-N-hydroxythiophene-2-carboxamide Compound I-34

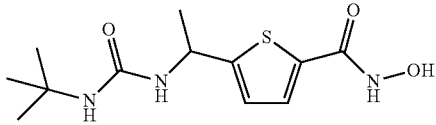 [SMILES: CC(NC(=O)NC(C)(C)C)c1ccc(C(=O)NO)s1]

The title compound was prepared in an analogous fashion to that described in Example 21 using t-butyl isocyanate. LC-MS: (FA) ES+ 286.

Example 27

N-hydroxy-5-[1-({[(1-phenylethyl)amino]carbonyl}amino)ethyl]thiophene-2-carboxamide Compound I-28

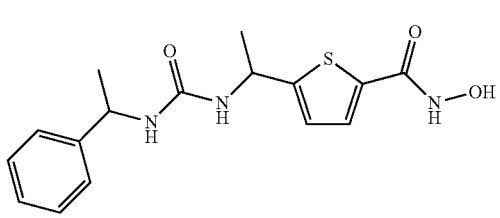 [SMILES: CC(NC(=O)NC(C)c1ccc(C(=O)NO)s1)c1ccccc1]

The title compound was prepared in an analogous fashion to that described in Example 21 using α-methylbenzyl isocyanate. LC-MS: (FA) ES+ 334.

Example 28

N-hydroxy-5-[1-({[(2-methoxy-5-methylphenyl)amino]carbonyl}amino)ethyl]thiophene-2-carboxamide Compound I-19

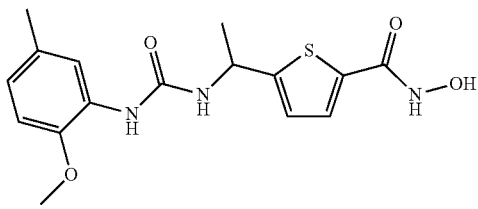 [SMILES: COc1ccc(C)cc1NC(=O)NC(C)c1ccc(C(=O)NO)s1]

The title compound was prepared in an analogous fashion to that described in Example 21 using 2-methoxy-5-methylphenyl isocyanate. LC-MS: (FA) ES+ 350.

Example 29

5-[1-({[(2,6-difluorophenyl)amino]carbonyl}amino)ethyl]-N-hydroxythiophene-2-carboxamide Compound I-20

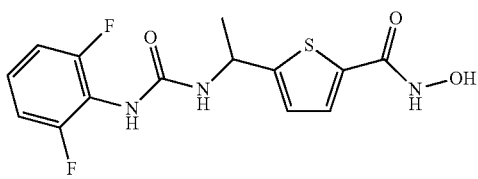 [SMILES: CC(NC(=O)Nc1c(F)cccc1F)c1ccc(C(=O)NO)s1]

The title compound was prepared in an analogous fashion to that described in Example 21 using 2,6-difluorophenyl isocyanate. LC-MS: (FA) ES+ 342.

Example 30

5-(1-{[(biphenyl-2-ylamino)carbonyl]amino}ethyl)-N-hydroxythiophene-2-carboxamide Compound I-27

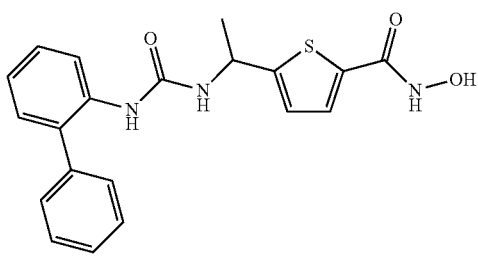 [SMILES: CC(NC(=O)Nc1ccccc1-c1ccccc1)c1ccc(C(=O)NO)s1]

The title compound was prepared in an analogous fashion to that described in Example 21 using 2-biphenylyl isocyanate. LC-MS: (FA) ES+ 382.

Example 31

N-hydroxy-5-[1-({[(3-methylphenyl)amino]carbonyl}amino)ethyl]thiophene-2-carboxamide Compound I-30

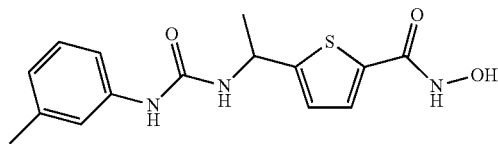 [SMILES: Cc1cccc(NC(=O)NC(C)c2ccc(C(=O)NO)s2)c1]

The title compound was prepared in an analogous fashion to that described in Example 21 using m-tolyl phenyl isocyanate. LC-MS: (FA) ES+ 320.

Example 32

N-hydroxy-5-{1-[({[4-(trifluoromethoxy)phenyl]amino}carbonyl)amino]ethyl}thiophene-2-carboxamide Compound I-22

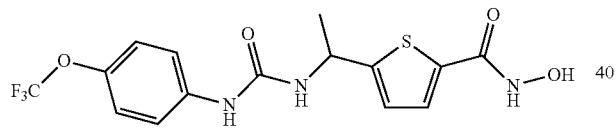

The title compound was prepared in an analogous fashion to that described in Example 21 using 4-trifluoromethoxyphenyl isocyanate. LC-MS: (FA) ES+ 390.

Example 33

5-[1-({[(4-tert-butylphenyl)amino]carbonyl}amino)ethyl]-N-hydroxythiophene-2-carboxamide Compound I-36

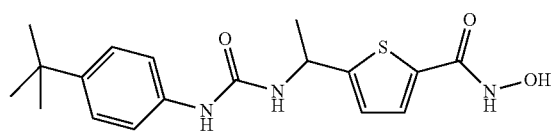 [SMILES: CC(NC(=O)Nc1ccc(C(C)(C)C)cc1)c1ccc(C(=O)NO)s1]

The title compound was prepared in an analogous fashion to that described in Example 21 using 4-tert-butylphenyl isocyanate. LC-MS: (FA) ES+ 362.

Example 34

5-[1-({[(2,6-dimethylphenyl)amino]carbonyl}amino)ethyl]-N-hydroxythiophene-2-carboxamide Compound I-32

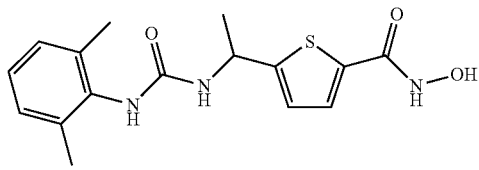 [SMILES: Cc1cccc(C)c1NC(=O)NC(C)c1ccc(C(=O)NO)s1]

The title compound was prepared in an analogous fashion to that described in Example 21 using 2,6-dimethylphenyl isocyanate. LC-MS: (FA) ES+ 334.

Example 35

5-[1-({[(3,5-dichlorophenyl)amino]carbonyl}amino)ethyl]-N-hydroxythiophene-2-carboxamide Compound I-4

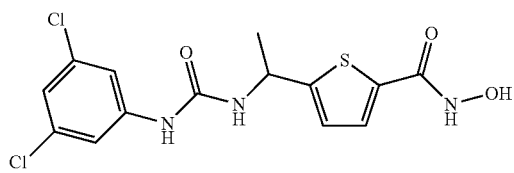 [SMILES: CC(NC(=O)Nc1cc(Cl)cc(Cl)c1)c1ccc(C(=O)NO)s1]

The title compound was prepared in an analogous fashion to that described in Example 21 using 3,5-dichlorophenyl isocyanate. LC-MS: (FA) ES+ 374.

Example 36

5-{1-[({[4-chloro-3-(trifluoromethyl)phenyl]amino}carbonyl)amino]ethyl}-N-hydroxythiophene-2-carboxamide Compound I-10

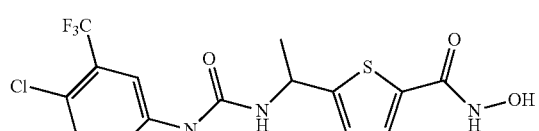

The title compound was prepared in an analogous fashion to that described in Example 21 using 3-trifluoromethyl-4-chlorophenyl isocyanate. LC-MS: (FA) ES+ 408.

Example 37

N-hydroxy-5-[1-({[(2-methylbenzyl)amino]carbonyl}amino)ethyl]thiophene-2-carboxamide Compound I-42

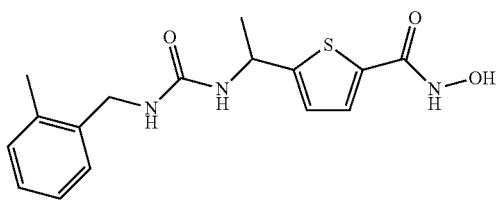 [SMILES: Cc1ccccc1CNC(=O)NC(C)c1ccc(C(=O)NO)s1]

The title compound was prepared in an analogous fashion to that described in Example 21 using 2-methylbenzyl isocyanate. LC-MS: (FA) ES+ 334.

Example 38

5-[1-({[(3,4-dimethylphenyl)amino]carbonyl}amino)ethyl]-N-hydroxythiophene-2-carboxamide Compound I-38

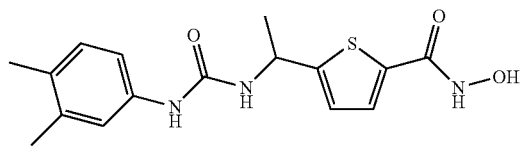 [SMILES: Cc1ccc(NC(=O)NC(C)c2ccc(C(=O)NO)s2)cc1C]

The title compound was prepared in an analogous fashion to that described in Example 21 using 3,4-dimethylphenyl isocyanate. LC-MS: (FA) ES+ 334.

Example 39

5-{1-[({[2-fluoro-5-(trifluoromethyl)phenyl]amino}carbonyl)amino]ethyl}-N-hydroxythiophene-2-carboxamide Compound I-7

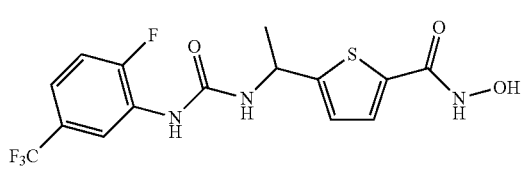 [SMILES: CC(NC(=O)Nc1cc(C(F)(F)F)ccc1F)c1ccc(C(=O)NO)s1]

The title compound was prepared in an analogous fashion to that described in Example 21 using 2-fluoro-5-trifluoromethylphenyl isocyanate. LC-MS: (FA) ES+ 392.

Example 40

N-hydroxy-5-[1-({[(3-methyl-5-phenylisoxazol-4-yl)amino]carbonyl}amino)ethyl]thiophene-2-carboxamide Compound I-41

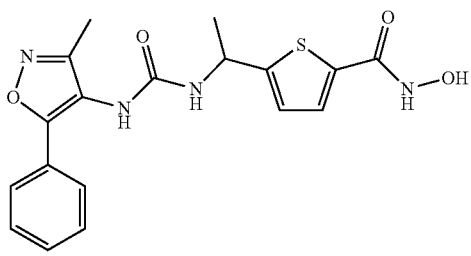 [SMILES: Cc1noc(-c2ccccc2)c1NC(=O)NC(C)c1ccc(C(=O)NO)s1]

The title compound was prepared in an analogous fashion to that described in Example 21 using 3-methyl-5-phenyl-isoxazol-4-yl isocyanate. LC-MS: (FA) ES+ 387.

Example 41

5-[1-({[(4-fluorophenyl)amino]carbonyl}amino)ethyl]-N-hydroxythiophene-2-carboxamide Compound I-2

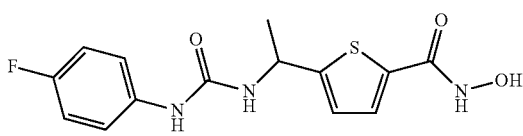 [SMILES: CC(NC(=O)Nc1ccc(F)cc1)c1ccc(C(=O)NO)s1]

The title compound was prepared in an analogous fashion to that described in Example 21 using 4-fluorophenyl isocyanate. LC-MS: (FA) ES+ 324.

Example 42

5-[1-({[(2,4-dimethylphenyl)amino]carbonyl}amino)ethyl]-N-hydroxythiophene-2-carboxamide Compound I-13

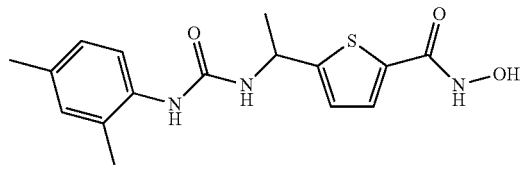 [SMILES: Cc1ccc(NC(=O)NC(C)c2ccc(C(=O)NO)s2)c(C)c1]

The title compound was prepared in an analogous fashion to that described in Example 21 using 2,4-dimethylphenyl isocyanate. LC-MS: (FA) ES+ 334.

Example 43

N-hydroxy-5-[1-({[(4-phenoxyphenyl)amino]carbonyl}amino)ethyl]thiophene-2-carboxamide Compound I-14

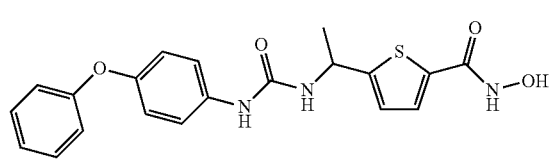 [SMILES: CC(NC(=O)Nc1ccc(Oc2ccccc2)cc1)c1ccc(C(=O)NO)s1]

The title compound was prepared in an analogous fashion to that described in Example 21 using 4-phenoxyphenyl isocyanate. LC-MS: (FA) ES+ 398.

Example 44

N-hydroxy-5-{1-[({[3-(trifluoromethyl)phenyl]amino}carbonyl)amino]ethyl}thiophene-2-carboxamide Compound I-3

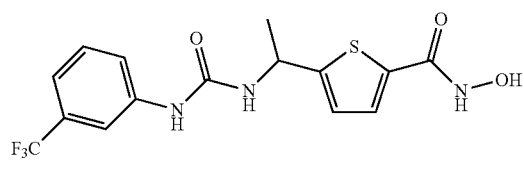 [SMILES: CC(NC(=O)Nc1cccc(C(F)(F)F)c1)c1ccc(C(=O)NO)s1]

The title compound was prepared in an analogous fashion to that described in Example 21 using 3-trifluoromethylphenyl isocyanate. LC-MS: (FA) ES+ 374.

Example 45

N-hydroxy-5-{1-[({[4-(trifluoromethyl)phenyl]amino}carbonyl)amino]ethyl}thiophene-2-carboxamide Compound I-45

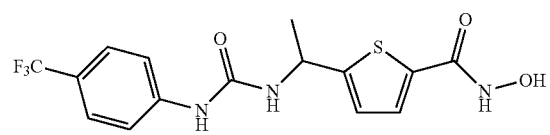 [SMILES: CC(NC(=O)Nc1ccc(C(F)(F)F)cc1)c1ccc(C(=O)NO)s1]

The title compound was prepared in an analogous fashion to that described in Example 21 using 4-trifluoromethylphenyl isocyanate. LC-MS: (FA) ES+ 374.

Example 46

N-hydroxy-5-[1-({[(2-phenoxyphenyl)amino]carbonyl}amino)ethyl]thiophene-2-carboxamide Compound I-44

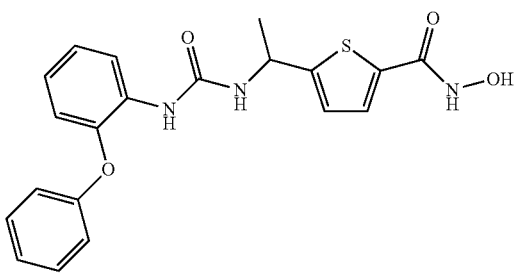 [SMILES: CC(NC(=O)Nc1ccccc1Oc1ccccc1)c1ccc(C(=O)NO)s1]

The title compound was prepared in an analogous fashion to that described in Example 21 using o-phenoxyphenyl isocyanate. LC-MS: (FA) ES+ 398.

Example 47

5-{1-[({[4-(difluoromethoxy)phenyl]amino}carbonyl)amino]ethyl}-N-hydroxythiophene-2-carboxamide Compound I-37

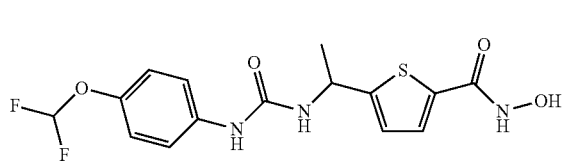 [SMILES: CC(NC(=O)Nc1ccc(OC(F)F)cc1)c1ccc(C(=O)NO)s1]

The title compound was prepared in an analogous fashion to that described in Example 21 using 4-difluorophenyl isocyanate. LC-MS: (FA) ES+ 372.

Example 48

5-{1-[({[2-chloro-4-(trifluoromethyl)phenyl]amino}carbonyl)amino]ethyl}-N-hydroxythiophene-2-carboxamide Compound I-25

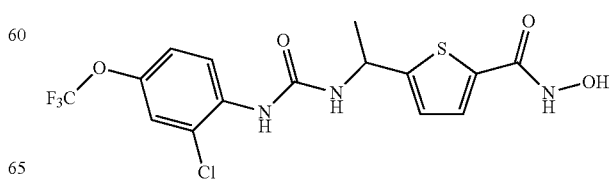

The title compound was prepared in an analogous fashion to that described in Example 21 using 2-chloro-4-trimethoxyphenyl isocyanate LC-MS: (FA) ES+ 424

Example 49

5-(1-{[(2-fluorophenyl)sulfonyl]amino}ethyl)-N-hydroxythiophene-2-carboxamide Compound I-47

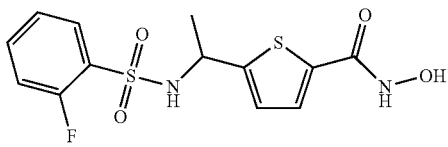 [SMILES: CC(NS(=O)(=O)c1ccccc1F)c1ccc(C(=O)NO)s1]

To a solution of methyl 5-(1-aminoethyl)thiophene-2-carboxylate hydrochloride (0.0332 g, 0.150 mmol) and N,N-diisopropylethylamine (12 uL, 0.71 mmol) in 1,2-dichloroethane (1 mL) was added 4-fluorobenzenesulfonyl chloride (45 mg, 0.23 mmol). The reaction solution was stirred at room temperature overnight. The solution was diluted with additional DCE (2 mL) and washed with saturated aqueous sodium bicarbonate (2 mL). The layers were separated and the organic layer evaporated to dryness. The material obtained was redissolved in a mixture of methanol (0.5 mL) and TI-IF (1 mL). 1.0 M aqueous sodium hydroxide (0.50 mL, 0.5 mmol) was added and the reaction solution was stirred at 40° C. overnight. Upon cooling to room temperature, the reaction was neutralized with 1.0 M hydrochloric acid (0.50 mL) and evaporated to dryness. The crude material obtained was taken up in DMF (1 mL) and to the solution was added HATU (62.7 mg, 0.16 mmol) and N,N-diisopropylethylamine (78.4 uL, 0.450 mmol). The reaction mixture was stirred at room temperature for 10 minutes whereupon a solution of 0.2M O-(tetrahydropyran-2-yl)hydroxylamine in DMF (1 mL, 0.2 mmol) was added. The reaction solution was stirred at room temperature overnight. To the residue was added 1,2-dichloroethane (3 mL), sat. NaHCO₃ solution (0.5 mL), and water (0.5 mL). After separation, the aqueous layer was extracted with 1,2-dichloroethane (2×3 mL). The combined organic phases were concentrated to dryness. The crude material was dissolved in THF (1.00 mL) and to the solution was added 4.0 M HCl in 1,4-dioxane (0.25 mL, 1 mmol). The reaction was stirred for 2 hours at room temperature, evaporated to dryness, redissolved in DMSO (1 mL) and purified using an Agilent 1100 LC/MSD instrument to afford the title compound as a white solid (3.3 mg, 15%) LC-MS: (FA) ES+ 345.

Example 50

N-hydroxy-5-{1-[(phenylsulfonyl)amino]ethyl}thiophene-2-carboxamide Compound I-48

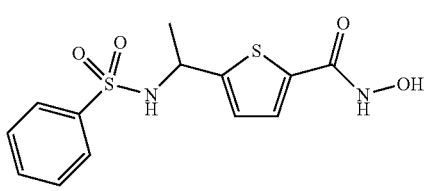 [SMILES: CC(NS(=O)(=O)c1ccccc1)c1ccc(C(=O)NO)s1]

The title compound was prepared in an analogous fashion to that described in Example 49 using benzenesulfonyl chloride. LC-MS: (FA) ES+ 327.

Example 51

N-hydroxy-5-(1-{[(1-methyl-1H-imidazol-4-yl)sulfonyl]amino}ethyl)thiophene-2-carboxamide Compound I-33

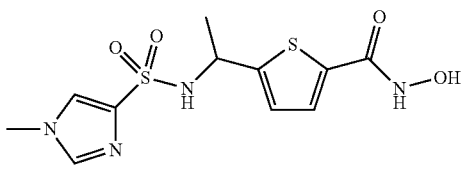 [SMILES: CC(NS(=O)(=O)c1cn(C)cn1)c1ccc(C(=O)NO)s1]

The title compound was prepared in an analogous fashion to that described in Example 49 using 1-methyl-1H-imidazole-4-sulfonyl chloride. LC-MS: (FA) ES+ 331.

Example 52

N-hydroxy-5-(1-{[(2-methylphenyl)sulfonyl]amino}ethyl)thiophene-2-carboxamide Compound I-35

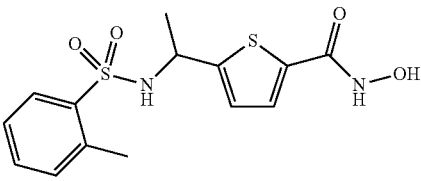 [SMILES: Cc1ccccc1S(=O)(=O)NC(C)c1ccc(C(=O)NO)s1]

The title compound was prepared in an analogous fashion to that described in Example 49 using 2-methylbenzene-1-sulfonyl chloride. LC-MS: (FA) ES+ 341.

Example 53

5-(1-aminoethyl)thiophene-2-carboxylate Hydrochloride

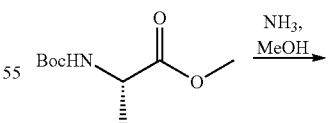

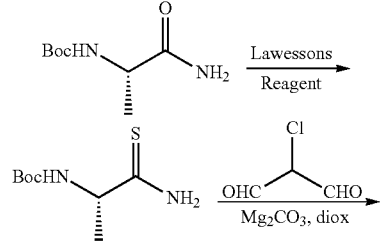

-continued

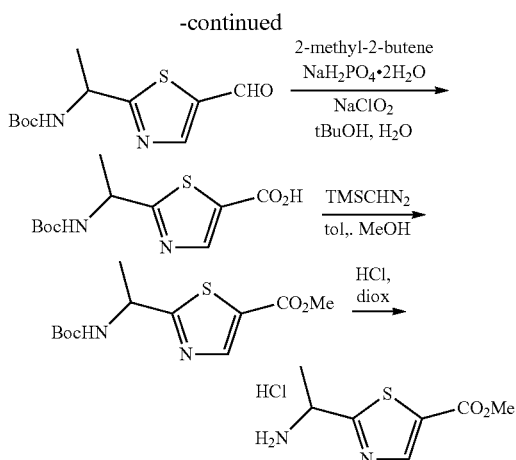

Step 1: N-tert-Butoxycarbonyl-L-alanine Amide

A mixture of Boc-L-alanine methyl ester (5.1 g, 25 mmol) and 4M $NH_3$ in MeOH (100 mL) was stirred overnight. Evaporation of the reaction to dryness afforded white solid (4.6 g, 97%). LC-MS: (FA) ES+ 189.

Step 2: (S)-tert-butyl 1-amino-1-thioxopropan-2-ylcarbamate

A mixture of N-tert-butoxycarbonyl-L-alanine amide (5.8 g, 0.031 mol) and 2,4-bis(4-methoxyphenyl)-2,4-dithioxo-1,3,2,4-dithiadiphosphetane (6.2 g, 0.015 mol) in THF (200 mL) was stirred at room temperature overnight. The solvent was removed by evaporation and the crude material purified by column chromatography (ethyl acetate/hexane, 1:2) to afford (S)-tert-butyl 1-amino-1-thioxopropan-2-ylcarbamate (5.5 g, 87%). LC-MS: (FA) ES+ 205.

Step 3: Tert-butyl 1-(5-formylthiazol-2-yl)ethylcarbamate

A mixture of (S)-tert-butyl 1-amino-1-thioxopropan-2-ylcarbamate (6.9 g, 0.03 mol), 2-chloromalonaldehyde (5.2 g, 0.049 mol) and magnesium carbonate (2.76 g, 0.03 mol) in 1,4-dioxane (400 mL) was heated at 60° C. for 3 hours and further at room temperature overnight. The reaction mixture was concentrated and the residue purified by column chromatography (50-80% EtOAc/hexane) to afford tert-butyl 1-(5-formylthiazol-2-yl)ethylcarbamate (5.5 g, 64%). LC-MS: (FA) ES+ 257.

Step 4: 2-(1-(tert-butoxycarbonylamino)ethyl)thiazole-5-carboxylic Acid

A mixture of tert-butyl 1-(5-formylthiazol-2-yl)ethylcarbamate (3.5 g, 0.014 mol), sodium dihydrogen phosphate dihydrate (2.9 g, 0.019 mol) and 2-methyl-2-butene (3.85 g, 0.055 mol) in tert-butyl alcohol (70 ml) and water (40 mL) was stirred at room temperature for 30 minutes. Sodium chlorite (3.22 g, 0.035 mol) was added and the reaction maintained at room temperature for an additional 2 hours. The reaction was concentrated, diluted with water (50 mL) and acidified (pH=4) with the addition of 3N $H_3PO_4$. The mixture was extracted with DCM, the organic layer dried over anhydrous $Na_2SO4$ and evaporated to dryness to afford 2-(1-(tert-butoxycarbonylamino)ethyl)thiazole-5-carboxylic acid (2.35 g, 60%). LC-MS: (FA) ES+ 273.

Step 5: Methyl 2-(1-(tert-butoxycarbonylamino)ethyl)thiazole-5-carboxylate

To a solution of 2-(1-(tert-butoxycarbonylamino)ethyl)thiazole-5-carboxylic acid (1.03 g, 3.8 mmol) in a mixture of MeOH (20 mL) and toluene (20 mL) cooled to 0° C. was added dropwise 2.0M trimethylsilyldiazomethane in ether (12 mL, 24 mmol). The resulting reaction mixture was warmed to room temperature overnight. Excess trimethylsilyldiazomethane was quenched with the addition of acetic acid and the solution concentrated to dryness. The residue was partitioned between EtOAc and saturated aqueous $NaHCO_3$, the organic layer dried over anhydrous $Mg_2SO4$ and concentrated to afford a yellow oil (0.90 g, 83%). LC-MS: (FA) ES+ 287.

Step 6: Methyl 2-(1-aminoethyl)thiazole-5-carboxylate Hydrochloride

To a solution of methyl 2-(1-(tert-butoxycarbonylamino)ethyl)thiazole-5-carboxylate (0.9 g, 3 mmol) in MeOH (5 mL) was added 4M HCl in dioxane (4 mL). The reaction was stirred overnight at room temperature. The reaction was evaporated to dryness to afford 5-(1-aminoethyl)thiophene-2-carboxylate hydrochloride (0.7 g, 100%).

Example 54

N-hydroxy-2-(1-{[(1-methyl-1H-pyrrol-2-yl)carbonyl]amino}ethyl)-1,3-thiazole-5-carboxamide Compound I-52

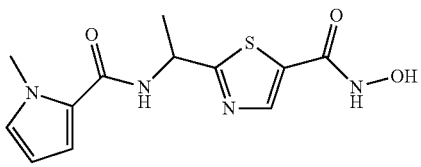 [SMILES: CC(NC(=O)c1cccn1C)c1ncc(C(=O)NO)s1]

To a solution of methyl 2-(1-aminoethyl)thiazole-5-carboxylate hydrochloride (33.4 mg, 0.150 mmol) and N-methylpyrrole-2-carboxylic acid (20 mg, 0.16 mmol) in DMF (1 mL) was added HATU (62.7 mg, 0.165 mmol) and N,N-diisopropylethylamine (52.2 uL, 0.300 mmol). The reaction mixture was stirred at room temperature overnight. The solution was evaporated to dryness. To the residue was added 1,2-dichloroethane (3 mL), sat. $NaHCO_3$ solution (0.5 mL), and water (0.5 mL). After separation, the aqueous layer was extracted with 1,2-dichloroethane (2×3 mL). The combined organic phases were concentrated to dryness. The material obtained was dissolved in MeOH (1 mL) and to the solution was added hydroxylamine hydrochloride (20 mg, 0.3 mmol) and potassium hydroxide (50 mg, 0.9 mmol). The reaction mixture was heated to 80° C. for 30 minutes. Upon cooling to room temperature, the reaction was quenched with the addition of acetic acid (0.05 mL), concentrated to dryness, redissolved in DMSO and purified on Agilent 1100 LC/MSD instrument to afford the title compound as a white solid (3.9 mg, 11%) LC-MS: (FA) ES+ 295.

Example 55

2-{1-[(2,2-dimethylpropanoyl)amino]ethyl}-N-hydroxy-1,3-thiazole-5-carboxamide Compound I-53

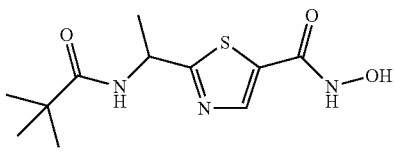 [SMILES: CC(NC(=O)C(C)(C)C)c1ncc(C(=O)NO)s1]

The title compound was prepared in an analogous fashion to that described in Example 54 using pivalic acid. LC-MS: (FA) ES+ 272.

Example 56

2-{1-[(1-benzothien-2-ylcarbonyl)amino]ethyl}-N-hydroxy-1,3-thiazole-5-carboxamide Compound I-54

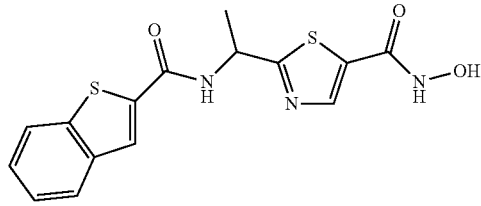 [SMILES: CC(NC(=O)c1cc2ccccc2s1)c1ncc(C(=O)NO)s1]

The title compound was prepared in an analogous fashion to that described in Example 54 using benzo[b]thiophene-2-carboxylic acid. LC-MS: (FA) ES+ 366.

Example 57

2-[1-({[1-(4-chlorophenyl)cyclobutyl]carbonyl}amino)ethyl]-N-hydroxy-1,3-thiazole-5-carboxamide Compound I-55

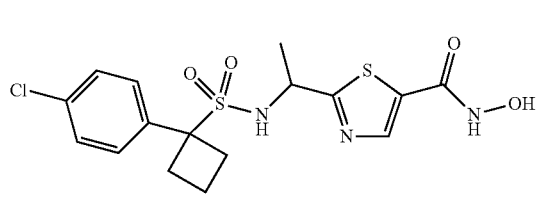 [SMILES: CC(NS(=O)(=O)C1(c2ccc(Cl)cc2)CCC1)c1ncc(C(=O)NO)s1]

The title compound was prepared in an analogous fashion to that described in Example 54 using 1-(4-chlorophenyl)cyclobutanecarboxylic acid. LC-MS: (FA) ES+ 380.

Example 58

2-(1-{[4-(benzyloxy)benzoyl]amino}ethyl)-N-hydroxy-1,3-thiazole-5-carboxamide Compound I-49

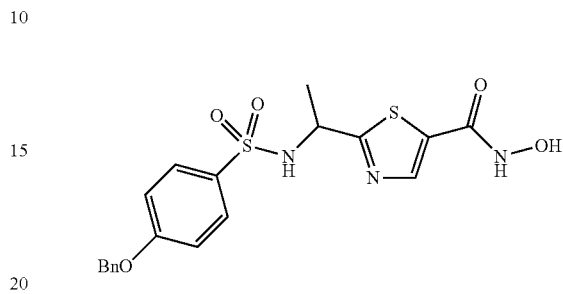

The title compound was prepared in an analogous fashion to that described in Example 54 using benzyloxybenzoic acid. LC-MS: (FA) ES+ 398.

Example 59

2-(1-{[(5-chloro-1-benzofuran-2-yl)carbonyl]amino}ethyl)-N-hydroxy-1,3-thiazole-5-carboxamide Compound I-50

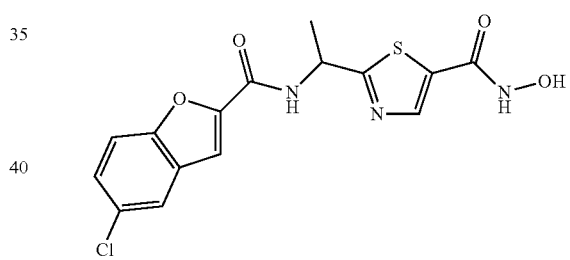

The title compound was prepared in an analogous fashion to that described in Example 54 using 5-chlorobenzofuran-2-carboxylic acid. LC-MS: (FA) ES+ 366.

Example 60

N-(1-{5-[(hydroxyamino)carbonyl]-1,3-thiazol-2-yl}ethyl)-1-methyl-1H-indole-2-carboxamide Compound I-51

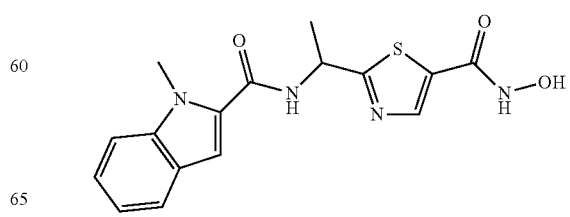

The title compound was prepared in an analogous fashion to that described in Example 54 using 1-methyl-1H-indole-2-carboxylic acid. LC-MS: (FA) ES+ 345.

Example 61

Benzyl 2-(1-aminoethyl)thiazole-5-carboxylate Hydrochloride

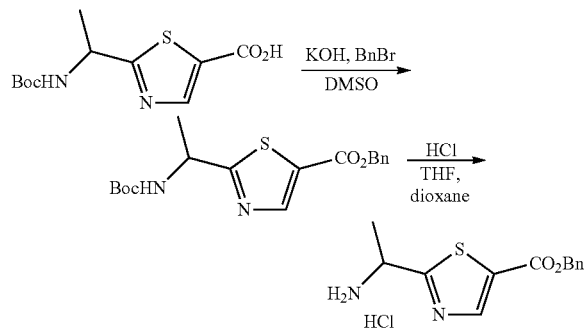

Step 1: Benzyl 2-(1-(tert-butoxycarbonylamino)ethyl)thiazole-5-carboxylate

To a solution of 2-(1-(tert-butoxycarbonylamino)ethyl)thiazole-5-carboxylic acid (0.14 g, 0.5 mmol) in DMSO (1 mL) was added KOH (0.031 g, 0.55 mmol). The mixture was stirred at room temperature until the full dissolution of KOH was observed. Benzyl bromide (0.06 mL, 0.53 mmol) was added and the reaction solution was stirred at room temperature overnight. The solution was partitioned between EtOAc and saturated aqueous $NaHCO_3$. The organic layer was dried over anhydrous $MgSO_4$, concentrated and purified by column chromatography to afford a colorless oil (0.133 g, 73%). LC-MS: (FA) ES+ 363.

Step 2: Benzyl 2-(1-aminoethyl)thiazole-5-carboxylate Hydrochloride

To a solution of benzyl 2-(1-(tert-butoxycarbonylamino)ethyl)thiazole-5-carboxylate (0.55 g, 0.55 mmol) in THF (2 mL) was added 4M HCl in dioxane (0.5 ml). The reaction solution was stirred at room temperature overnight. The solution was concentrated to dryness to afford a colorless oil (0.45 g, 100%). LC-MS: (FA) ES+ 263.

Example 62

(R)-ethyl 3-(1-aminoethyl)isoxazole-5-carboxylate Hydrochloride

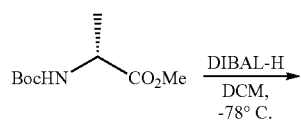

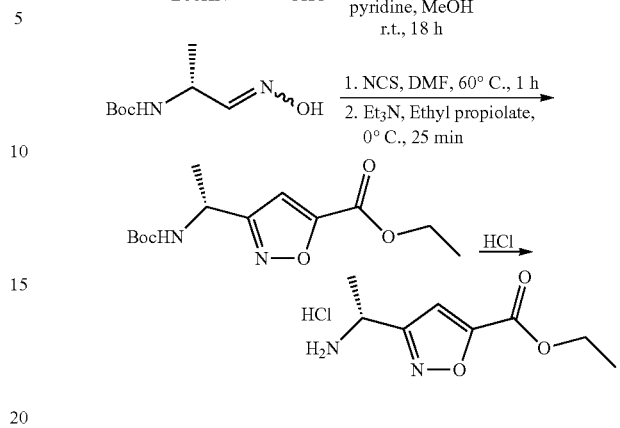

Step 1: (R)-tert-butyl 1-oxopropan-2-ylcarbamate

To a cooled solution of (R)-methyl 2-(tert-butoxycarbonylamino)propanoate (40.0 g, 98.0 mmol) in DCM (200 mL) at −78° C. was added diisobutylaluminum hydride (208 mL, 1.0 M in THF) dropwise over 30 min. The reaction mixture was stirred at −78° C. for 1.5 h then quenched with water (50 mL). After warmed to rt, the white precipitate was removed by filtration over Celite. The organic layer was then washed with brine, dried ($Na_2SO_4$), and concentrated. The crude residue was purified by flash chromatography (petroleum ether:EtOAc, 10:1) to give (R)-tert-butyl 1-oxopropan-2-ylcarbamate (28.0 g, 82%). $^1$H NMR (DMSO-$d_6$, 400 MHz) δ 9.43 (s, 1H), 7.33 (d, J=6.0 Hz, 1H), 3.85 (m, 1H), 1.39 (s, 9H), 1.12 (d, J=7.2 Hz, 3H).

Step 2: (R)-tert-butyl 1-(hydroxyimino)propan-2-ylcarbamate

A mixture of (R)-tert-butyl 1-oxopropan-2-ylcarbamate (28.0 g, 81.0 mmol), hydroxylamine hydrochloride (11.2 g, 81.0 mmol), pyridine (60 mL), MeOH (100 mL) was stirred at rt overnight. The solvent was then evaporated. To the residue was added water (100 mL) and the mixture was extracted with DCM (3×200 mL). The combined organic phases were dried ($Na_2SO_4$) and concentrated. The crude residue was purified by flash column chromatography (petroleum ether:EtOAc, 4:1) to give (R)-tert-butyl 1-(hydroxyimino)propan-2-ylcarbamate (24.0 g, 79%). $^1$H NMR (DMSO-$d_6$, 400 MHz) δ 10.63 (s, 1H), 7.20 (d, J=5.2 Hz, 1H), 4.12 (m, 1H), 1.38 (s, 9H), 1.15 (d, J=6.8 Hz, 3H).

Step 3: Diethyl (R)-ethyl 3-(1-(tert-butoxycarbonylamino)ethyl)isoxazole-5-carboxylate To a solution of diethyl (R)-tert-butyl 1-(hydroxyimino)propan-2-ylcarbamate (24.0 g, 21.0 mmol) in THF (300 mL) was added N-chlorosuccinimide (16.8 g, 21.0 mmol) and the mixture was heated at 60° C. for 1.5 h. The solution was then cooled to 0° C. and ethyl propiolate (30.0 mL, 42.0 mmol) was added followed slow addition of TEA (19.2 mL) in THF (120 mL) over 30 min. Water (300 mL) was added to quench the reaction and the aqueous solution was extracted with DCM (3×400 mL). The crude residue was purified by flash column chromatography (petroleum ether:EtOAc, 10:1) to give diethyl (R)-ethyl 3-(1-(tert-butoxycarbonylamino)ethyl)

isoxazole-5-carboxylate (17.0 g, 47%). ¹H NMR (CDCl₃, 400 MHz) δ 6.86 (s, 1H), 4.95 (m, 1H), 4.40 (q, J=7.2 Hz, 2H), 1.52 (t, J=7.2 Hz, 3H), 1.42 (s, 9H), 1.37 (t, J=7.2 Hz, 3H).

Step 4: (R)-ethyl 3-(1-aminoethyl)isoxazole-5-carboxylate Hydrochloride

To a flask pre-charged with diethyl (R)-ethyl 3-(1-(tert-butoxycarbonylamino)ethyl)isoxazole-5-carboxylate (17.0 g, 59.8 mmol) was added hydrochloric acid (200 mL, 4.0 M in dioxane) and the resulting mixture was stirred at rt for 4 h. The solvent was removed and to the residue was added water (30 mL). The aqueous solution was then washed with DCM (10 mL), and lyophilized to give (R)-ethyl 3-(1-aminoethyl)isoxazole-5-carboxylate hydrochloride (10.2 g, 92%). ¹H NMR (CD₃OD, 400 MHz) δ 7.26 (s, 1H), 4.75 (m, 1H), 4.43 (q, J=7.2 Hz, 2H), 1.69 (t, J=6.8 Hz, 3H), 1.39 (t, J=7.2 Hz, 3H).

Example 63

(R)-3-(1-(benzofuran-2-carboxamido)ethyl)-N-hydroxyisoxazole-5-carboxamide Compound I-181

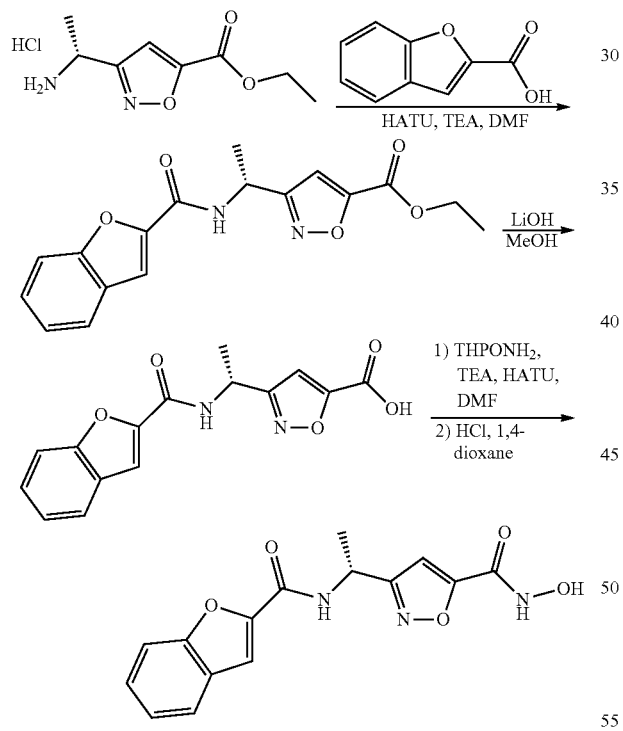

Step 1: (R)-ethyl 3-(1-(benzofuran-2-carboxamido)ethyl)isoxazole-5-carboxylate To a 2-dram vial containing benzofuran-2-carboxylic acid (0.0243 g, 0.150 mmol) was added HATU (0.057 g, 0.150 mmol.) in DMF (1.0 mL), and TEA (0.120 mL, 0.858 mmol). After shaking at rt for 30 min, (R)-ethyl 3-(1-aminoethyl)isoxazole-5-carboxylate hydrochloride (0.032 g, 0.143 mmol) was added. The mixture was shaken at rt for 16 h. The solvent was evaporated. To the residue was added water (1.0 mL) and DCE (3 mL). After separation, the aqueous layer was extracted with DCE (3 mL). The combined organic phases were concentrated to give (R)-ethyl 3-(1-(benzofuran-2-carboxamido)ethyl)isoxazole-5-carboxylate as a solid residue.

Step 2: (R)-3-(1-(benzofuran-2-carboxamido)ethyl) isoxazole-5-carboxylic Acid To the crude (R)-ethyl 3-(1-(benzofuran-2-carboxamido) ethyl)isoxazole-5-carboxylate was added lithium hydroxide (0.572 mL, 1.0 M in water), and MeOH (1.0 mL). The mixture was shaken at rt for 16 h, then hydrochloric acid (0.214 mL, 4.0 M in 1,4-dioxane) was added to acidify the reaction. Most of the solvent was evaporated. To the residue was added water (1.0 mL) and DCE (3 mL). After separation, the aqueous layer was extracted with DCE (3 mL). The combined organic phases were concentrated to give crude (R)-3-(1-(benzofuran-2-carboxamido)ethyl)isoxazole-5-carboxylic acid.

Step 3: ((R)-3-(1-(benzofuran-2-carboxamido)ethyl)-N-hydroxyisoxazole-5-carboxamide To the crude (R)-3-(1-(benzofuran-2-carboxamido)ethyl) isoxazole-5-carboxylic acid in a microwave vial was added HATU (0.0544 g, 0.143 mmol), TEA (0.087 g, 0.858 mmol) in DMF (1.0 mL), followed by O-(tetrahydropyran-2-yl)hydroxylamine (0.0335 g, 0.286 mmol) in DMF (1.0 mL). The mixture was shaken at rt for 16 h, then the solvent was evaporated. To the residue was added THF (2.0 mL) and hydrochloric acid (0.0715 mL, 4.0 M in 1,4-dioxane). After shaking at rt for 1 h, the solvent was evaporated. To the residue was added DMSO (1.2 mL). After filtration, the solution was purified by prep-HPLC to give ((R)-3-(1-(benzofuran-2-carboxamido)ethyl)-N-hydroxyisoxazole-5-carboxamide. LC-MS: (FA) ES+ 347.

Example 64

The following compounds were prepared in an analogous fashion to that described in Example 63 from appropriate starting materials

| Compound No | LC-MS (FA) |
|---|---|
| I-170 | ES+ 334 |
| I-176 | ES+ 332 |
| I-182 | ES+ 256 |
| I-158 | ES+ 352 |
| I-164 | ES+ 306 |
| I-163 | ES+ 374 |
| I-157 | ES+ 296 |

Example 65

Tert-butyl 5-((R)-1-((S)-1,1-dimethylethylsulfinamido)ethyl)-1-methyl-1H-pyrrole-3-carboxylate

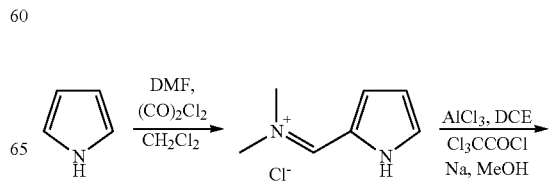

143

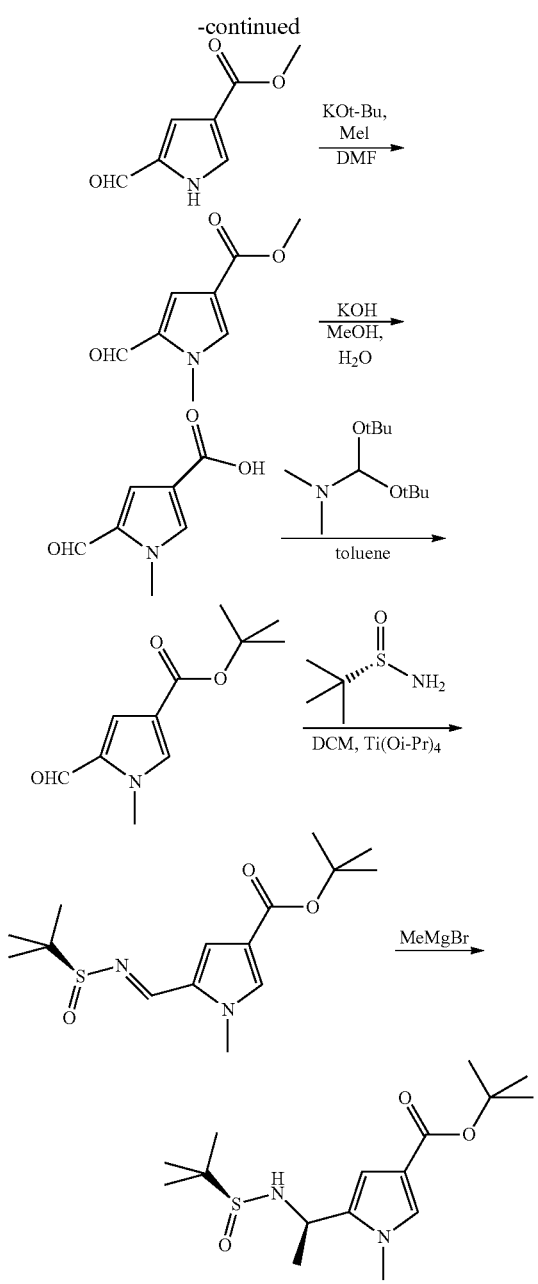

Step 1: N-((1H-pyrrol-2-yl)methylene)-N-methyl-methanaminium Chloride

A solution of DMF (60.0 mL, 738 mmol) in DCM (60 mL) was added to a stirred solution of oxalyl chloride in DCM (60 mL) at 0° C. The mixture was stirred at 0° C. for 20 min then a solution of pyrrole (45.0 g, 666 mmol) in DCM (150 mL) was added over 15 min. This reaction mixture was stirred at rt for 20 min and concentrated to roughly half its volume. Petroleum ether (200 mL) was added and the precipitate was collected by filtration to give N-((1H-pyrrol-2-yl)methylene)-N-methylmethanaminium chloride (90.0 g, 80%). $^1$H NMR (DMSO-d$_6$, 400 MHz) δ 13.23 (s, 1H), 8.65 (s, 1H), 7.79 (s, 1H), 7.45 (s, 1H), 6.68 (q, J=1.6 Hz, 1H), 3.70 (s, 3H), 3.64 (s, 3H).

144

Step 2: Methyl 5-formyl-1H-pyrrole-3-carboxylate

To a solution of N-((1H-pyrrol-2-yl)methylene)-N-methylmethanaminium chloride (45.0 g, 0.279 mol), aluminum trichloride (83.7 g, 0.63 mol) in DCE (90 mL) under nitrogen was added 2,2,2-trichloroacetyl chloride (32.4 mL, 0.093 mol). The mixture was heated to reflux for 4 h. After cooled to rt, MeOH (100 mL) was added followed by sodium methoxide solution [prepared with sodium (45.0 g, 1.98 mol) and MeOH (180 mL)]. The resulting mixture was then stirred at rt for 2 h. The solvent was then removed and the resulting residue was dissolved in water (100 mL), neutralized with 1 N HCl, and extracted with EtOAc (3×400 mL). The combined organic phases were washed with brine, dried, and concentrated to give methyl 5-formyl-1H-pyrrole-3-carboxylate (30.0 g, 60%). $^1$H NMR (DMSO-d$_6$, 400 MHz) δ 12.62 (s, 1H), 9.48 (s, 1H), 7.66 (s, 1H), 7.30 (s, 1H), 3.67 (s, 3H).

Step 3: Methyl 5-formyl-1-methyl-1H-pyrrole-3-carboxylate

To a solution of methyl 5-formyl-1H-pyrrole-3-carboxylate (60.0 g, 0.360 mol) in DMF (60 mL) was added potassium tert-butoxide (72.0 g, 0.576 mol). After stirring at rt for 30 min, the mixture was cooled to 0° C. and methyl iodide (132 mL, 1.45 mol) was added. The solution was then stirred at rt overnight. Water was added to quench the reaction and the solution was extracted with DCM (3×200 mL). The combined organic phases were washed with brine (50 mL), dried (Na$_2$SO$_4$), and concentrated to give methyl 5-formyl-1-methyl-1H-pyrrole-3-carboxylate (45.0 g, 80%). $^1$H NMR (CDCl$_3$, 400 MHz) δ 12.62 (s, 1H), 9.48 (s, 1H), 7.66 (s, 1H), 7.30 (s, 1H), 3.67 (s, 3H).

Step 4: Methyl 5-formyl-1-methyl-1H-pyrrole-3-carboxylic Acid

To a solution of methyl 5-formyl-1-methyl-1H-pyrrole-3-carboxylate (90.0 g, 0.540 mol), MeOH (1000 mL) and water (500 mL) was added sodium hydroxide solution (1000 mL, 1.0 M in water). The mixture was heated at 40° C. overnight. Solvent was then evaporated, and the aqueous residue was neutralized with 1 N HCl and extracted with EtOAc (3×500 mL) to give methyl 5-formyl-1-methyl-1H-pyrrole-3-carboxylic acid (70.0 g, 85%). $^1$H NMR (CDCl$_3$, 400 MHz) δ 9.54 (s, 1H), 7.45 (s, 1H), 7.32 (s, 1H), 3.93 (s, 3H).

Step 5: Tert-butyl 5-formyl-1-methyl-1H-pyrrole-3-carboxylate

To a solution of methyl 5-formyl-1-methyl-1H-pyrrole-3-carboxylic acid (45.0 g, 0.29 mol) in toluene (500 mL) at reflux condition was added 1,1-di-tert-butoxy-N,N-dimethylmethanamine (300 mL, 0.83 mol) dropwise. The mixture was then refluxed overnight and the solvent was then evaporated. The residue was purified by flash column chromatography (petroleum ether:EtOAc, 5:1) to give tert-butyl 5-formyl-1-methyl-1H-pyrrole-3-carboxylate (27.0 g, 65%). $^1$H NMR (CDCl$_3$, 400 MHz) δ 9.50 (s, 1H), 7.30 (s, 1H), 7.20 (s, 1H), 3.89 (s, 3H), 1.48 (s, 9H).

Step 6: (S,E)-tert-butyl 5-((tert-butylsulfinylimino)methyl)-1-methyl-1H-pyrrole-3-carboxylate To a solution of tert-butyl 5-formyl-1-methyl-1H-pyrrole-3-carboxylate (3.0 g, 14.5 mmol), (S)-2-methylpropane-2-sulfinamide (2.6 g, 21.8 mmol) in DCM (200 mL) was added titanium isopropoxide (24.8 g, 87 mmol). The mixture was stirred at rt for 20 h then water (30 mL) was added to quench the reaction. The solid precipitate was filtered and the filtrate was concentrated and purified by flash column chromatography (petroleum ether:EtOAc, 5:1) to give (S,E)-tert-butyl 5-((tert-butylsulfinylimino)methyl)-1-methyl-1H-pyrrole-3-carboxylate (2.9 g, 63%). $^1$H NMR (CDCl$_3$, 400 MHz) δ 8.30 (s, 1H), 7.29 (s, 1H), 7.02 (s, 1H), 3.89 (s, 3H), 1.48 (s, 9H), 1.16 (s, 9H).

Step 7: Tert-butyl 5-((R)-1-((S)-1,1-dimethylethylsulfinamido)ethyl)-1-methyl-1H-pyrrole-3-carboxylate To a solution of (S,E)-tert-butyl 5-((tert-butylsulfinylimino)methyl)-1-methyl-1H-pyrrole-3-carboxylate (3.0 g, 10 mmol) in DCM (60 mL) was slowly added methylmagnesium bromide (13.3 mL, 3.0 M in ether) at −78° C. After stirring at −78° C. for 1 h, the solution was warmed to rt and stirred for 2 h. The reaction was quenched with sat. NH$_4$Cl solution. After separation, the organic phase was washed with brine (5 mL), dried (Na$_2$SO$_4$) and concentrated. Flash column chromatography (petroleum ether:EtOAc, 10:1 to 1:1) afforded tert-butyl 5-((R)-1-((S)-1,1-dimethylethylsulfinamido)ethyl)-1-methyl-1H-pyrrole-3-carboxylate (2.2 g, 70%). $^1$H (CDCl$_3$, 400 MHz) δ 7.15 (s, 1H), 6.47 (s, 1H), 4.48 (m, 1H), 3.62 (s, 3H), 3.18 (m, 1H), 1.68 (d, J=6.6 Hz, 3H), 1.52 (s, 9H), 1.19 (s, 9H).

Example 66

Tert-butyl 2-((R)-1-((S)-1,1-dimethylethylsulfinamido)ethyl)thiazole-5-carboxylate

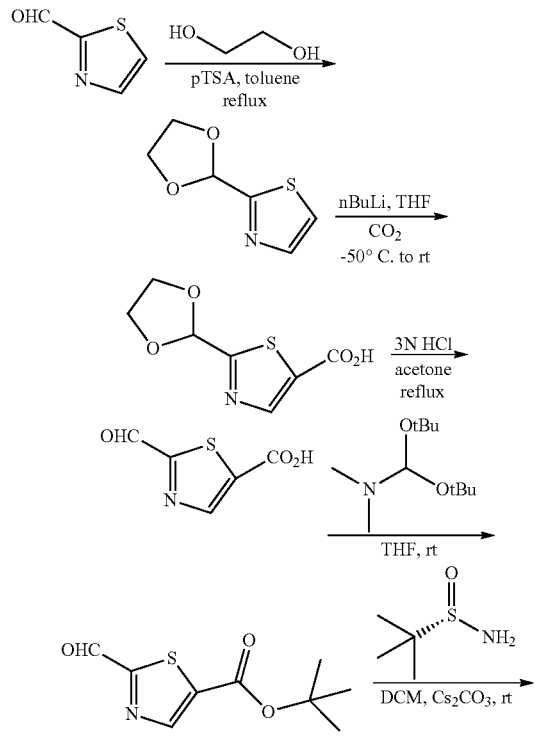

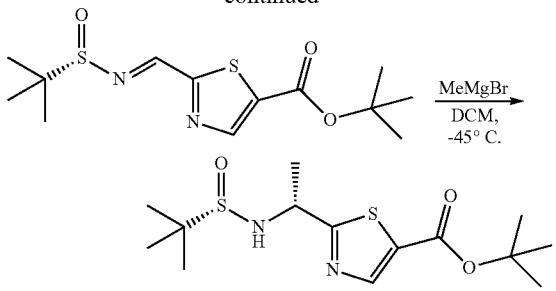

Step 1: 2-(1,3-dioxolan-2-yl)thiazole

A solution of thiazole-2-carbaldehyde (100 g, 0.88 mol), ethane-1,2-diol (164 g, 2.65 mol), p-toluenesulfonic acid monohydrate (50 g, 0.26 mol) in toluene (1000 mL) was refluxed overnight with azetropic removal of water. The mixture was cooled to rt, diluted with ether (1000 mL), and washed with sat. NaHCO$_3$ solution (200 mL), brine (200 mL), dried (Na$_2$SO$_4$), and concentrated to give a yellow oil. Flash column chromatography (petroleum ether:EtOAc, 100:1 to 50:1) afforded 2-(1,3-dioxolan-2-yl)thiazole (185 g, 66%). $^1$H NMR (CDCl$_3$, 300 MHz) δ 7.75 (s, 1H), 7.31 (s, 1H), 6.09 (s, 1H), 4.04 (m, 4H).

Step 2: 2-(1,3-dioxolan-2-yl)thiazole-5-carboxylic Acid

To a solution of 2-(1,3-dioxolan-2-yl)thiazole (65 g, 0.41 mol) in THF (900 mL) under nitrogen was slowly added n-BuLi (180 mL, 2.5 M in hexanes) at −78° C. The mixture was stirred at −78° C. for 2 h, and then solid dry ice was added. The solution was then warmed to rt and stirred overnight. Hydrochloric acid (2 N) was added to the solution until pH<4. The mixture was then extracted with ether (5×300 mL). Combined organic phases were washed with water (200 mL), brine (200 mL), dried (Na$_2$SO$_4$), and concentrated to give a yellow solid. This solid was then rinsed with petroleum ether to give 2-(1,3-dioxolan-2-yl)thiazole-5-carboxylic acid (72.5 g, 87%). $^1$H NMR (dmso-d$_6$, 400 MHz) δ 13.70 (s, 1H), 8.36 (s, 1H), 6.10 (s, 1H), 4.06 (m, 4H).

Step 3: 2-formylthiazole-5-carboxylic Acid

A solution of 2-(1,3-dioxolan-2-yl)thiazole-5-carboxylic acid (20 g, 0.1 mol) in hydrochloric acid (1000 mL, 3 N) and acetone (1000 mL) was heated to reflux for 6 h. The solution was then extracted with ether (5×500 mL). The combined organic phases were dried (Na$_2$SO$_4$) and concentrated. Flash column chromatography (petroleum ether:EtOAc, 100:1 to 5:1) afforded 2-formylthiazole-5-carboxylic acid (36 g, 76%). %). $^1$H NMR (DMSO-d$_6$, 300 MHz) δ 13.90 (br, 1H), 9.92 (s, 1H), 8.63 (s, 1H).

Step 4: Tert-butyl 2-formylthiazole-5-carboxylate

A solution of 2-formylthiazole-5-carboxylic acid (28.7 g, 0.18 mol) and 1,1-di-tert-butoxy-N,N-dimethylmethanamine (380 g, 1.8 mol) was heated to 40° C. to initiate the reaction, then cooled to rt immediately and stirred at rt for 3 h. The mixture was filtered and the filtrate was concentrated. The crude residue was purified by flash column chromatography (petroleum ether:EtOAc, 100:1) to give tert-butyl 2-formylthiazole-5-carboxylate (25 g, 64%). $^1$H NMR (CDCl$_3$, 400 MHz) δ 9.92 (s, 1H), 8.46 (s, 1H), 1.53 (s, 9H).

Step 5: (S,E)-tert-butyl 2-((tert-butylsulfinylimino)methyl)thiazole-5-carboxylate To a solution of tert-butyl 2-formylthiazole-5-carboxylate (15.7 g, 74 mmol) and (S)-2-methylpropane-2-sulfinamide (10.7 g, 88 mmol) in DCM (750 mL) at 0° C. was added cesium carbonate (48.2 g, 148 mmol). The mixture was warmed to rt and stirred for 8 h. To the solution was added water (200 mL). After separation, the aqueous phase was extracted with DCM (3×200 mL). The combined organic phases were dried (Na$_2$SO$_4$), and concentrated. Flash column chromatography (petroleum ether:EtOAc, 100:1 to 10:1) afforded (S,E)-tert-butyl 2-((tert-butylsulfinylimino)methyl)thiazole-5-carboxylate (18.9 g, 81%). $^1$H NMR (CDCl$_3$, 400 MHz) δ 8.67 (s, 1H), 8.39 (s, 1H), 1.52 (s, 9H), 1.22 (s, 9H).

Step 6: Tert-butyl 2-((R)-1-(S)-1,1-dimethylethylsulfinamido)ethyl)thiazole-5-carboxylate To a solution of (S,E)-tert-butyl 2-((tert-butylsulfinylimino)methyl)thiazole-5-carboxylate (15 g, 47 mmol) in DCM (500 mL) at −70° C. was slowly added methylmagnesium bromide (63 mL, 3 M in ether). The mixture was stirred at −70° C. for 3 h then quenched with sat. NH$_4$Cl solution. The solution was then warmed to rt. After separation, the aqueous phase was extracted with DCM (3×200 mL). Combined organic phases were dried (Na$_2$SO$_4$), and concentrated. Flash column chromatography (DCM:MeOH, 100:0 to 100:1) afforded tert-butyl 2-((R)-1-((S)-1,1-dimethylethylsulfinamido)ethyl)thiazole-5-carboxylate (10 g, 64%). $^1$H NMR (CDCl$_3$, 400 MHz) δ 8.14 (s, 1H), 4.76 (m, 1H), 4.15 (m, 1H), 1.60 (d, J=6.8 Hz, 3H), 1.50 (s, 9H), 1.20 (s, 9H).

Example 67

Tert-butyl 2-((S)-1-((R)-1,1-dimethylethylsulfinamido)ethyl)thiazole-5-carboxylate

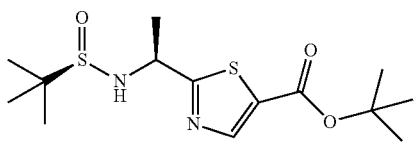 [SMILES: C[C@H](N[S@](=O)C(C)(C)C)c1ncc(C(=O)OC(C)(C)C)s1]

The title compound was prepared in an analogous fashion to that described in Example 66 starting from 2-formylthiazole-5-carboxylic acid and (R)-2-methylpropane-2-sulfinamide.

Example 68

The following compounds were prepared in an analogous fashion to that described in Example 4 from appropriate starting materials.

| Compound No | LC-MS (FA) |
|---|---|
| I-179 | ES+ 350 |
| I-160 | ES+ 295 |
| I-177 | ES+ 370 |
| I-180 | ES+ 348 |
| I-161 | ES+ 368 |
| I-173 | ES+ 346 |
| I-159 | ES+ 332 |
| I-175 | ES+ 322 |
| I-168 | ES+ 390 |
| I-183 | ES+ 272 |
| I-171 | ES+ 312 |
| I-167 | ES+ 390 |
| I-166 | ES+ 272 |
| I-172 | ES+ 350 |
| I-174 | ES+ 295 |
| I-178 | ES+ 348 |
| I-169 | ES+ 322 |
| I-165 | ES+ 332 |
| I-162 | ES+ 312 |
| I-156 | ES+ 386 |

II. Biological Data

Example 69

HDAC6 Enzyme Assay

To measure the inhibition of HDAC6 activity, purified human HDAC6 (BPS Bioscience; Cat. No. 5006) is incubated with substrate Ac-Arg-Gly-Lys(Ac)-AMC peptide (Bachem Biosciences; Cat. No. I-1925) for 1 hour at 30° C. in the presence of test compounds or vehicle DMSO control. The reaction is stopped with the HDAC inhibitor trichostatin A (Sigma; Cat. No. T8552) and the amount of Arg-Gly-Lys-AMC generated is quantitated by digestion with trypsin (Sigma; Cat. No. T1426) and subsequent measurement of the amount of AMC released using a fluorescent plate reader (Pherastar; BMG Technologies) set at Ex 340 nm and Em 460 nm. Concentration response curves are generated by calculating the fluorescence increase in test compound-treated samples relative to DMSO-treated controls, and enzyme inhibition (IC$_{50}$) values are determined from those curves.

Example 70

Nuclear Extract HDAC Assay

As a screen against Class I HDAC enzymes, HeLa nuclear extract (BIOMOL; Cat. No. KI-140) is incubated with Ac-Arg-Gly-Lys(Ac)-AMC peptide (Bachem Biosciences; Cat. No. I-1925) in the presence of test compounds or vehicle DMSO control. The HeLa nuclear extract is enriched for Class I enzymes HDAC1, -2 and -3. The reaction is stopped with the HDAC inhibitor Trichostatin A (Sigma; Cat. No. T8552) and the amount of Arg-Gly-Lys-AMC generated is quantitated by digestion with trypsin (Sigma; Cat. No. T1426) and subsequent measurement of the amount of AMC released using a fluorescent plate reader (Pherastar; BMG Technologies) set at Ex 340 nm and Em 460 nm. Concentration response curves are generated by calculating the fluorescence increase in test compound-treated samples relative to DMSO-treated controls, and enzyme inhibition (IC$_{50}$) values are determined from those curves.

Example 71

Cell Assays

Western Blot and Immunofluorescence Assays

Cellular potency and selectivity of compounds are determined using a published assay (Haggarty et al., *Proc. Natl. Acad. Sci. USA* 2003, 100 (8): 4389-4394) using Hela cells (ATCC cat# CCL-2™) which are maintained in MEM medium (Invitrogen) supplemented with 10% FBS; or multiple myeloma cells RPMI-8226 (ATCC cat# CCL-155™) which are maintained in RPMI 1640 medium (Invitrogen) supplemented with 10% FBS. Briefly, cells are treated with inhibitors for 6 or 24 h and either lysed for Western blotting, or fixed for immunofluorescence analyses. HDAC6 potency is determined by measuring K40 hyperacetylation of alpha-tubulin with an acetylation selective monoclonal antibody (Sigma cat# T7451) in IC50 experiments. Selectivity against Class I HDAC activity is determined similarly using an antibody that recognizes hyperacetylation of histone H4 (Upstate cat#06-866) in the Western blotting assay or nuclear acetylation (Abcam cat# ab21623) in the immunofluorescence assay.

Example 72

Anti-Proliferation Assays

ATPlite Assay

The ATPLite™ (Perkin-Elmer) Assay measures cellular adenosine-triphosphate (ATP) through the generation of a luminescent signal formed from the ATP dependent enzyme firefly luciferase. The luminescent signal intensity can be used as a measure of cellular proliferation, and therefore the anti-proliferative effects of HDAC6 inhibitors with or without combinations of other cytotoxic compounds. Test compound(s) (4 µL in 100% DMSO) are diluted in 75 µL of Hanks Buffered Saline Solution (Invitrogen). The diluted test compounds (8 µL) are then added to 384-well TC-treated Black/Clear plates (Falcon). HCT-116 cells (ATCC cat# CCL-247™) maintained in McCoy's 5a modified media (Invitrogen) containing 10% Fetal Bovine Serum and 1% Penicillin-Streptavadin are added at 1000 cells/well for a 72 hour assay. For 48 hour incubation assays, the cell seeding densities are RPMI-8226 (ATCC cat# CCL-155™)—6000 cells/well; U266B1 (ATCC cat# TIB-196™)—8000 cells/well; NCIH929 (ATCC cat# CRL-9068™)—10000 cells/well. For 72 hour incubation assays, the cell seeding densities are RPMI-8226—3000 cells/well; U266B1—4000 cells/well; NCIH929—7500 cells/well. RPMI-8226 cells are maintained in RPMI 1640 medium (ATCC) with 2 mM L-Glutamine, 10 mM HEPES, 1 mM sodium pyruvate. 4.5 g/L glucose, 1.5 g/L sodium bicarbonate, 10% FBS; U266B1 cells in RPMI 1640 medium (ATCC) with 2 mM L-Glutamine, 10 mM HEPES, 1 mM sodium pyruvate. 4.5 g/L glucose, 1.5 g/L sodium bicarbonate, 15% FBS; and NCI-H929 cells in RPMI 1640 medium (ATCC) with 2 mM L-Glutamine, 10 mM HEPES, 1 mM sodium pyruvate. 4.5 g/L glucose, 1.5 g/L sodium bicarbonate, 0.05 mM 2-mercaptoethanol, 10% FBS. The cells are incubated with compound in a humidified chamber at 37° C. for 72 hours. The plates are removed from the cell culture chambers and allowed to equilibrate to room temperature for 30 min. All but 25 µL of cell culture media is removed from each well, and 25 ul of ATPlite reagent (Perkin Elmer) is added to each well. Luminescence is measured within 5 minutes of adding the ATPlite reagent on a LEADSeeker Luminescence Counter (GE Healthcare Life Sciences). Concentration response curves are generated by calculating the luminescence decrease in test compound-treated samples relative to DMSO-treated controls, and growth inhibition ($IC_{50}$) values are determined from those curves.

As detailed above, compounds of the invention inhibit HDAC6. In certain embodiments, compounds of the invention inhibit HDAC6 with an IC50 value of less than 100 nM including compounds: I-1, I-2, I-3, I-5, I-7, I-9, I-10, I-12, I-13, I-14, I-15, I-16, I-17, I-18, I-19, I-21, I-22, I-25, I-29, I-30, I-31, I-36, I-37, I-38, I-39, I-40, I-42, I-44, I-45, I-46, I-49, I-50, I-51, I-54, I-159, I-161, I-165, I-167, I-168, I-173, I-178, I-180.

In certain embodiments, compounds of the invention inhibit HDAC6 with an IC50 value of greater than 100 nM and less than 500 nM including compounds: I-4, I-8, I-20, I-23, I-24, I-26, I-27, I-28, I-32, I-33, I-34, I-35, I-41, I-47, I-48, I-52, I-160, I-169, I-174, I-175, I-177.

In certain embodiments, compounds of the invention inhibit HDAC6 with an IC50 value of greater than 500 nM including compounds: I-6, I-11, I-43, I-53, I-55, I-156, I-157, I-158, I-162, I-163, I-164, I-166, I-170, I-171, I-172, I-176, I-179, I-181, I-182, I-183.

As detailed above, compounds of the invention are selective for HDAC6 over other Class I HDAC enzymes. In certain embodiments, the ratio of HDAC IC50 (as obtained in the nuclear extract assay described above) to HDAC6 IC50 is less than 5 (HDAC IC50/HDAC6 IC50). In certain embodiments, the ratio of HDAC IC50 to HDAC6 IC50 is between 5 and 10. In certain embodiments, the ratio of HDAC IC50 to HDAC6 IC50 is between 10 and 100.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

What is claimed is:

1. A compound of formula (I-i), (I-v), or (I-xi):

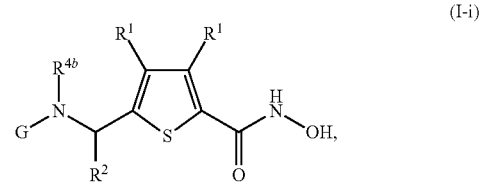

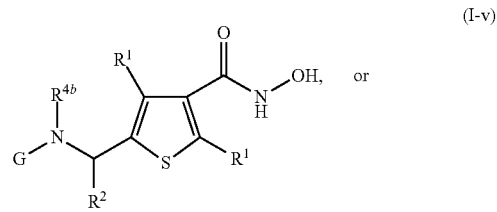

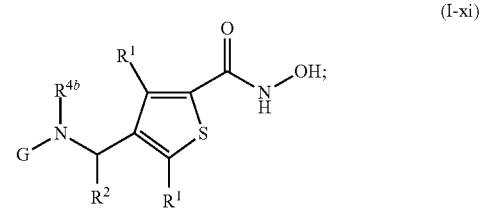

or a pharmaceutically acceptable salt thereof; wherein:

each occurrence of $R^1$ is independently hydrogen, halogen, $C_{1-4}$ alkyl, $C_{1-3}$ fluoroalkyl, —O—$C_{1-3}$ alkyl, —O—$C_{1-3}$ fluoroalkyl, cyano, hydroxy, —NHC(O)$C_{1-3}$ alkyl, —C(O)NH$C_{1-3}$ alkyl, —NHC(O)NH$C_{1-3}$ alkyl, or —NHS(O)$_2$$C_{1-3}$ alkyl;

$R^2$ is $C_{1-6}$ aliphatic, $C_{1-6}$ fluoroaliphatic, or unsubstituted or substituted 6-10-membered aryl;

$R^{4b}$ is hydrogen, or $C_{1-4}$ aliphatic;

G is —$R^3$, —$V_1$—$R^3$, —$V_1$-$L_1$-$R^3$, -$L_2$-$V_1$—$R^3$, -$L_2$-$V_2$—$R^3$, or -$L_1$-$R^3$, $L_1$ is an unsubstituted or substituted $C_{1-3}$ alkylene chain;

$L_2$ is an unsubstituted or substituted $C_{2-3}$ alkylene chain;

$V_1$ is —C(O)—, —C(O)—$CR^A$=$CR^A$—, —C(O)—N($R^{4a}$)—, —C(O)—O—, or —S(O)$_2$—;

$V_2$ is —C(S)—, —N($R^{4a}$)—, —N($R^{4a}$)—C(O)—, —SO$_2$—N($R^{4a}$)—, —N($R^{4a}$)—SO$_2$—, —O—, —S—, —S(O)—, —N($R^{4a}$)—C(O)—N($R^{4a}$)—, —N($R^{4a}$)—C(O)—O—, —O—C(O)—N($R^{4a}$)—, or —N($R^{4a}$)—SO$_2$—N($R^{4a}$)—;

$R^3$ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur;

each occurrence of $R^A$ is independently hydrogen, fluoro, or unsubstituted or substituted $C_{1-4}$ aliphatic; and each occurrence of $R^{4a}$ is independently hydrogen, or unsubstituted or substituted $C_{1-4}$ aliphatic.

2. The compound of claim 1, wherein:

$R^{4b}$ is H; and $R^2$ is methyl, ethyl, isopropyl, n-propyl, trifluoromethyl, tert-butyl, cyclopropyl, or phenyl.

3. The compound of claim 1, wherein:

G is —$V_1$—$R^3$; and $V_1$ is —C(O)—, —C(O)—N($R^{4a}$)—, or —S(O)$_2$—.

4. The compound of claim 1, wherein $R^1$ is hydrogen, chloro, fluoro, hydroxy, methoxy, ethoxy, n-propoxy, isopropoxy, cyano, trifluoromethyl, methyl, ethyl, isopropyl, n-propyl, or tert-butyl.

5. The compound of claim 1, represented by formulas (II-a-i), (II-a-v) or (II-a-xi):

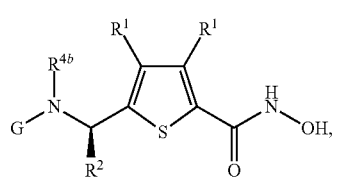

(II-a-i)

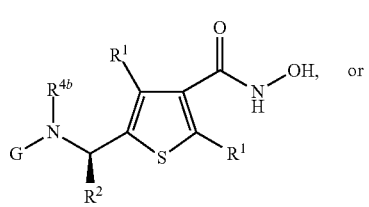

(II-a-v)

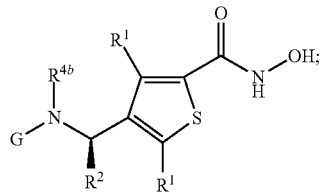

(II-a-xi)

wherein:

each occurrence of $R^1$ is independently hydrogen, halogen, $C_{1-4}$ alkyl, $C_{1-3}$ fluoroalkyl, —O—$C_{1-3}$ alkyl, —O—$C_{1-3}$ fluoroalkyl, cyano, hydroxy, —NHC(O)$C_{1-3}$ alkyl, —C(O)NH$C_{1-3}$ alkyl, —NHC(O)NH$C_{1-3}$ alkyl, or —NHS(O)$_2$$C_{1-3}$ alkyl;

$R^{1a}$ is hydrogen, or $C_{1-4}$ aliphatic;

$R^2$ is $C_{1-6}$ aliphatic, $C_{1-6}$ fluoroaliphatic, or unsubstituted or substituted 6-10-membered aryl;

$R^{4b}$ is hydrogen, or $C_{1-4}$ aliphatic;

G is —$R^3$, —$V_1$—$R^3$, —$V_1$-$L_1$-$R^3$, -$L_2$-$V_1$—$R^3$, -$L_2$-$V_2$—$R^3$, or -$L_1$-$R^3$, $L_1$ is an unsubstituted or substituted $C_{1-3}$ alkylene chain;

$L_2$ is an unsubstituted or substituted $C_{2-3}$ alkylene chain;

$V_1$ is —C(O)—, —C(O)—$CR^A$=$CR^A$—, —C(O)—N($R^{4a}$)—, —C(O)—O—, or —S(O)$_2$—;

$V_2$ is —C(S)—, —N($R^{4a}$)—, —N($R^{4a}$)—C(O)—, —SO$_2$—N($R^{4a}$)—, —N($R^{4a}$)—SO$_2$—, —O—, —S—, —S(O)—, —N($R^{4a}$)—C(O)—N($R^{4a}$)—, —N($R^{4a}$)—C(O)—O—, —O—C(O)—N($R^{4a}$)—, or —N($R^{4a}$)—SO$_2$—N($R^{4a}$)—;

$R^3$ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur;

each occurrence of $R^A$ is independently hydrogen, fluoro, or unsubstituted or substituted $C_{1-4}$ aliphatic; and each occurrence of $R^{4a}$ is independently hydrogen, or unsubstituted or substituted $C_{1-4}$ aliphatic.

6. The compound of claim 5, wherein:

$R^{4b}$ is H; and $R^2$ is methyl, ethyl, isopropyl, n-propyl, trifluoromethyl, tert-butyl, cyclopropyl, or phenyl.

7. The compound of claim 5, wherein:

G is —$V_1$—$R^3$; and $V_1$ is —C(O)—, —C(O)—N($R^{4a}$)—, or —S(O)$_2$—.

8. The compound of claim 5 wherein $R^1$ is hydrogen, chloro, fluoro, methoxy, ethoxy, n-propoxy, isopropoxy, cyano, trifluoromethyl, methyl, ethyl, isopropyl, n-propyl, or tert-butyl.

9. The compound of claim 5, wherein:

each substitutable carbon chain atom in $R^3$ is unsubstituted or substituted with 1-2 occurrences of —$R^{5dd}$;

each substitutable saturated ring carbon atom in $R^3$ is unsubstituted or substituted with =O, =S, =C($R^5$)$_2$, =N—N($R^4$)$_2$, =N—O$R^5$, =N—NHC(O)$R^5$, =N—NHCO$_2$$R^6$, =N—NHSO$_2$$R^6$, =N—$R^5$ or —$R^{5a}$;

each substitutable unsaturated ring carbon atom in $R^3$ is unsubstituted or is substituted with —$R^{5a}$;

each substitutable ring nitrogen atom in $R^3$ is unsubstituted or substituted with $-R^{9b}$;

each $R^{5a}$ is independently halogen, $-NO_2$, $-CN$, $-C(R^5)=C(R^5)_2$, $-C\equiv C-R^5$, $-OR^5$, $-SR^6$, $-S(O)R^6$, $-SO_2R^6$, $-SO_2N(R^4)_2$, $-N(R^4)_2$, $-NR^4C(O)R^5$, $-NR^4C(O)N(R^4)_2$, $-NR^4CO_2R^6$, $-OC(O)N(R^4)_2$, $-C(O)-C(O)R^5$, $-C(O)R^5$, $-C(O)N(R^4)_2$, $-C(=NR^4)-N(R^4)_2$, $-C(=NR^4)-OR^5$, $-N(R^4)-N(R^4)_2$, $-N(R^4)C(=NR^4)-N(R^4)_2$, $-N(R^4)SO_2R^6$, $-N(R^4)SO_2N(R^4)_2$, $-P(O)(R^5)_2$, $-P(O)(OR^5)_2$, unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two adjacent $R^{5a}$, taken together with the intervening ring atoms, form an unsubstituted or substituted fused aromatic ring or an unsubstituted or substituted nonaromatic ring having 0-3 heteroatoms independently selected from nitrogen, oxygen, and sulfur;

each occurrence of $R^{5dd}$ is independently halogen, $-OH$, $-O(C_{1-3}$ alkyl), $-CN$, $-N(R^4)_2$, $-C(O)(C_{1-3}$ alkyl), $-CO_2H$, $-CO_2(C_{1-3}$ alkyl), $-C(O)NH_2$, or $-C(O)NH(C_{1-3}$ alkyl);

each $R^4$ is independently hydrogen, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two $R^4$ on the same nitrogen atom, taken together with the nitrogen atom, form an unsubstituted or substituted 5- to 6-membered heteroaryl or an unsubstituted or substituted 4- to 8-membered heterocyclyl having, in addition to the nitrogen atom, 0-2 ring heteroatoms selected from nitrogen, oxygen, and sulfur;

each $R^5$ is independently hydrogen, unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur;

each $R^6$ is independently unsubstituted or substituted $C_{1-6}$ aliphatic, or unsubstituted or substituted 6-10-membered aryl;

each $R^7$ is independently unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur;

each $R^{9b}$ is independently $-C(O)R^5$, $-C(O)N(R^4)_2$, $-CO_2R^6$, $-SO_2R^6$, $-SO_2N(R^4)_2$, unsubstituted $C_{1-4}$ aliphatic, or $C_{1-4}$ aliphatic substituted with 1-2 occurrences of $R^7$ or $R^8$; and each $R^8$ is independently halogen, $-OH$, $-O(C_{1-3}$ alkyl), $-CN$, $-N(R^4)_2$, $-C(O)(C_{1-3}$ alkyl), $-CO_2H$, $-CO_2(C_{1-3}$ alkyl), $-C(O)NH_2$, or $-C(O)NH(C_{1-3}$ alkyl).

10. The compound of claim 9, wherein:
each substitutable saturated ring carbon atom in $R^3$ is unsubstituted or substituted with $-R^{5a}$;
the total number of $R^{5a}$ substituents is p;
p is 1-2;
each $R^{5a}$ is independently chloro, fluoro, hydroxy, methoxy, ethoxy, n-propoxy, isopropoxy, cyano, trifluoromethyl, methyl, ethyl, isopropyl, n-propyl, tert-butyl or phenyl; and
each occurrence of $R^{7a}$ is independently halogen, $C_{1-3}$ alkyl, $C_{1-3}$ fluoroalkyl, $-O-C_{1-3}$ alkyl, $-O-C_{1-3}$ fluoroalkyl, $-NHC(O)C_{1-3}$ alkyl, $-C(O)NHC_{1-3}$ alkyl, $-NHC(O)NHC_{1-3}$ alkyl, or $-NHS(O)_2C_{1-3}$ alkyl.

11. The compound of claim 9, represented by formula (III-a-i):

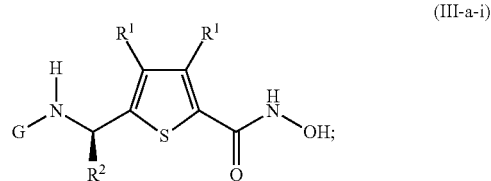

wherein:
each occurrence of $R^1$ is independently hydrogen, chloro, fluoro, hydroxy, trifluoromethyl, or methyl;
G is $-V_1-R^3$; and
$V_1$ is $-C(O)-$, $-C(O)-N(R^{4a})-$ or $-S(O)_2-$.

12. The compound of claim 11, wherein $R^1$ is hydrogen.

13. The compound of claim 11, wherein $R^2$ is methyl, ethyl, isopropyl, n-propyl, trifluoromethyl, tert-butyl, cyclopropyl, or phenyl.

14. The compound of claim 11, wherein $R^2$ is methyl, ethyl, isopropyl, or n-propyl.

15. The compound of claim 11, wherein:
each substitutable saturated ring carbon atom in $R^3$ is unsubstituted or substituted with $-R^{5a}$;
the total number of $R^{5a}$ substituents is p;
p is 1-2;
each $R^{5a}$ is independently chloro, fluoro, hydroxy, methoxy, ethoxy, n-propoxy, isopropoxy, cyano, trifluoromethyl, methyl, ethyl, isopropyl, n-propyl, tert-butyl or phenyl; and
each occurrence of $R^{7a}$ is independently halogen, $C_{1-3}$ alkyl, $C_{1-3}$ fluoroalkyl, $-O-C_{1-3}$ alkyl, $-O-C_{1-3}$ fluoroalkyl, $-NHC(O)C_{1-3}$ alkyl, $-C(O)NHC_{1-3}$ alkyl, $-NHC(O)NHC_{1-3}$ alkyl, or $-NHS(O)_2C_{1-3}$ alkyl.

16. A pharmaceutical composition comprising a compound of claim 1 and a pharmaceutically acceptable carrier.

17. The compound of claim 1, wherein the compound is:

I-1  5-(1-{[(cyclopentylamino)carbonyl]amino}ethyl)-N-hydroxythiophene-2-carboxamide;
I-2  5-[1-({[(4-fluorophenyl)amino]carbonyl}amino)ethyl]-N-hydroxythiophene-2-carboxamide;

-continued

| | |
|---|---|
| I-3 | N-hydroxy-5-{1-[({[3-(trifluoromethyl)phenyl]amino}carbonyl)-amino]ethyl}thiophene-2-carboxamide; |
| I-4 | 5-[1-({[(3,5-dichlorophenyl)amino]carbonyl}amino)ethyl]-N-hydroxythiophene-2-carboxamide; |
| I-5 | N-((1R)-1-{5-[(hydroxyamino)carbonyl]-2-thienyl}ethyl)-1-methyl-1H-indole-2-carboxamide; |
| I-6 | 5-{(1R)-1-[(2,2-dimethylpropanoyl)amino]ethyl}-N-hydroxythiophene-2-carboxamide; |
| I-7 | 5-{1-[({[2-fluoro-5-(trifluoromethyl)phenyl]amino}carbonyl)amino]ethyl}-N-hydroxythiophene-2-carboxamide; |
| I-8 | 5-((1R)-1-{[(tert-butylamino)carbonyl]amino}ethyl)-N-hydroxythiophene-2-carboxamide; |
| I-9 | N-hydroxy-5-{(1R)-1-[(4-methoxybenzoyl)amino]ethyl}thiophene-2-carboxamide; |
| I-10 | 5-{1-[({[4-chloro-3-(trifluoromethyl)phenyl]amino}carbonyl)-amino]ethyl}-N-hydroxythiophene-2-carboxamide; |
| I-11 | 5-{(1R)-1-[(1-adamantylcarbonyl)amino]ethyl}-N-hydroxythiophene-2-carboxamide; |
| I-12 | 5-{1-[(anilinocarbonyl)amino]ethyl}-N-hydroxythiophene-2-carboxamide; |
| I-13 | 5-[1-({[(2,4-dimethylphenyl)amino]carbonyl}amino)ethyl]-N-hydroxythiophene-2-carboxamide; |
| I-14 | N-hydroxy-5-[1-({[(4-phenoxyphenyl)amino]carbonyl}-amino)ethyl]thiophene-2-carboxamide; |
| I-15 | N-((1R)-1-{5-[(hydroxyamino)carbonyl]-2-thienyl}ethyl)-3-methyl-1-benzofuran-2-carboxamide; |
| I-16 | N-((1R)-1-{5-[(hydroxyamino)carbonyl]-2-thienyl}ethyl)-1-benzothiophene-2-carboxamide; |
| I-17 | 4,5-dichloro-N-((1R)-1-{5-[(hydroxyamino)carbonyl]-2-thienyl}ethyl)-1-methyl-1H-pyrrole-2-carboxamide; |
| I-18 | 5-(1-{[(benzylamino)carbonyl]amino}ethyl)-N-hydroxythiophene-2-carboxamide; |
| I-19 | N-hydroxy-5-[1-({[(2-methoxy-5-methylphenyl)amino]carbonyl}amino)ethyl]thiophene-2-carboxamide; |
| I-20 | 5-[1-({[(2,6-difluorophenyl)amino]carbonyl}amino)ethyl]-N-hydroxythiophene-2-carboxamide; |
| I-21 | N-((1S)-1-{5-[(hydroxyamino)carbonyl]-2-thienyl}ethyl)-1-benzothiophene-2-carboxamide; |
| I-22 | N-hydroxy-5-{1-[({[4-(trifluoromethoxy)phenyl]amino}carbonyl)amino]ethyl}thiophene-2-carboxamide; |
| I-23 | N-hydroxy-5-[(1R)-1-({[(4-(trifluoromethyl)phenyl]sulfonyl}amino)-ethyl]thiophene-2-carboxamide; |
| I-24 | 5-(1-{[(cyclohexylamino)carbonyl]amino}ethyl)-N-hydroxythiophene-2-carboxamide; |
| I-25 | 5-{1-[({[2-chloro-4-(trifluoromethyl)phenyl]amino}carbonyl)amino]-ethyl}-N-hydroxythiophene-2-carboxamide; |
| I-26 | 5-[(1R)-1-({[(3S,5S,7S)-1-adamantylamino]carbonyl}-amino)ethyl]-N-hydroxythiophene-2-carboxamide; |
| I-27 | 5-(1-{[(biphenyl-2-ylamino)carbonyl]amino}ethyl)-N-hydroxythiophene-2-carboxamide; |
| I-28 | N-hydroxy-5-[1-({[(1-phenylethyl)amino]carbonyl}amino)-ethyl]thiophene-2-carboxamide; |
| I-29 | N-((1R)-1-{5-[(hydroxyamino)carbonyl]-2-thienyl}ethyl)-1-methyl-1H-pyrrole-2-carboxamide; |
| I-30 | N-hydroxy-5-[1-({[(3-methylphenyl)amino]carbonyl}amino)ethyl]-thiophene-2-carboxamide; | or a pharmaceutically acceptable salt thereof.

18. The compound of claim 1, wherein the compound is:

| | |
|---|---|
| I-31 | N-((1R)-1-{5-[(hydroxyamino)carbonyl]-2-thienyl}ethyl)-3-methyl-1-benzothiophene-2-carboxamide; |
| I-32 | 5-[1-({[(2,6-dimethylphenyl)amino]carbonyl}amino)ethyl]-N-hydroxythiophene-2-carboxamide; |
| I-33 | N-hydroxy-5-(1-{[(1-methyl-1H-imidazol-4-yl)sulfonyl]amino}-ethyl)thiophene-2-carboxamide; |
| I-34 | 5-(1-{[(tert-butylamino)carbonyl]amino}ethyl)-N-hydroxythiophene-2-carboxamide; |
| I-35 | N-hydroxy-5-(1-{[(2-methylphenyl)sulfonyl]amino}ethyl)thiophene-2-carboxamide; |
| I-36 | 5-[1-({[(4-tert-butylphenyl)amino]carbonyl}amino)ethyl]-N-hydroxythiophene-2-carboxamide; |
| I-37 | 5-{1-[({[4-(difluoromethoxy)phenyl]amino}carbonyl)amino]ethyl}-N-hydroxythiophene-2-carboxamide; |
| I-38 | 5-[1-({[(3,4-dimethylphenyl)amino]carbonyl}amino)ethyl]-N-hydroxythiophene-2-carboxamide; |
| I-39 | N-((1R)-1-{5-[(hydroxyamino)carbonyl]-2-thienyl}ethyl)-1-benzofuran-2-carboxamide; |
| I-40 | N-hydroxy-5-[1-({[(2-methylphenyl)amino]carbonyl}amino)ethyl]-thiophene-2-carboxamide; |
| I-42 | N-hydroxy-5-[1-({[(2-methylbenzyl)amino]carbonyl}amino)ethyl]-thiophene-2-carboxamide; |
| I-43 | N-hydroxy-5-((1R)-1-{[(1-methylcyclohexyl)carbonyl]amino}ethyl)-thiophene-2-carboxamide; |
| I-44 | N-hydroxy-5-[1-({[(2-phenoxyphenyl)amino]carbonyl}amino)ethyl]-thiophene-2-carboxamide; |
| I-45 | N-hydroxy-5-{1-[({[4-(trifluoromethyl)phenyl]amino}carbonyl)-amino]ethyl}thiophene-2-carboxamide; |
| I-46 | 5-{(1R)-1-[(biphenyl-4-ylcarbonyl)amino]ethyl}-N-hydroxythiophene-2-carboxamide; |
| I-47 | 5-(1-{[(2-fluorophenyl)sulfonyl]amino}ethyl)-N-hydroxythiophene-2-carboxamide; |
| I-48 | N-hydroxy-5-{1-[(phenylsulfonyl)amino]ethyl}thiophene-2-carboxamide; |
| I-56 | N-(1-{5-[(hydroxyamino)carbonyl]-3-thienyl}ethyl)-1-methylpiperidine-4-carboxamide; |
| I-63 | 3-chloro-5-((1S)-1-{[(dimethylamino)acetyl]amino}ethyl)-N-hydroxythiophene-2-carboxamide; |
| I-65 | 5-((1R)-1-{[(1-adamantylamino)carbonyl]amino}butyl)-2-chloro-N-hydroxythiophene-3-carboxamide; |
| I-66 | 5-{(1S)-1-[(1-adamantylcarbonyl)amino]ethyl}-3-chloro-N-hydroxythiophene-2-carboxamide; |
| I-67 | N-((1S)-1-{5-[(hydroxyamino)carbonyl]-4-methyl-2-thienyl}propyl)-1-methylpiperidine-4-carboxamide; |
| I-70 | N-((1S)-1-{5-chloro-4-[(hydroxyamino)carbonyl]-2-thienyl}ethyl)-1-methylpiperidine-4-carboxamide; |
| I-71 | N-((1S)-1-{5-[(hydroxyamino)carbonyl]-4-methyl-2-thienyl}propyl)-1-methyl-1H-pyrrole-2-carboxamide; |
| I-75 | N-(1-{5-[(hydroxyamino)carbonyl]-3-thienyl}ethyl)-1-benzothiophene-2-carboxamide; |
| I-77 | 5-{(1S)-1-[(1-adamantylcarbonyl)amino]propyl}-N-hydroxy-3-methylthiophene-2-carboxamide; |
| I-83 | N-((1S)-1-{4-chloro-5-[(hydroxyamino)carbonyl]-2-thienyl}ethyl)-1-methylpiperidine-4-carboxamide; |
| I-87 | 4-{1-[(biphenyl-4-ylcarbonyl)amino]ethyl}-N-hydroxythiophene-2-carboxamide; |
| I-88 | 2-chloro-5-{(1S)-1-[(cyclopentylacetyl)amino]ethyl}-N-hydroxythiophene-3-carboxamide; |
| I-89 | 3-chloro-5-{(1S)-1-[(cyclopentylacetyl)amino]ethyl}-N-hydroxythiophene-2-carboxamide; | or a pharmaceutically acceptable salt thereof.

19. The compound of claim 1, wherein the compound is:

| | |
|---|---|
| I-93 | N-((1S)-1-{4-[(hydroxyamino)carbonyl]-2-thienyl}-2,2-dimethylpropyl)-1-methylpiperidine-4-carboxamide; |
| I-99 | 5-{(1S)-1-[(1-adamantylcarbonyl)amino]-2,2-dimethylpropyl}-N-hydroxythiophene-3-carboxamide; |
| I-103 | 2-chloro-5-{(1S)-1-[(2,2-dimethylpropanoyl)amino]ethyl}-N-hydroxythiophene-3-carboxamide; |
| I-104 | 4-{1-[(cyclopentylacetyl)amino]ethyl}-N-hydroxythiophene-2-carboxamide; |
| I-107 | N-((1S)-1-{4-chloro-5-[(hydroxyamino)carbonyl]-2-thienyl}ethyl)-1-methyl-1H-pyrrole-2-carboxamide; |
| I-110 | 4-{1-[(2,2-dimethylpropanoyl)amino]ethyl}-N-hydroxythiophene-2-carboxamide; |
| I-118 | N-((1S)-1-{5-chloro-4-[(hydroxyamino)carbonyl]-2-thienyl}ethyl)-1-methyl-1H-indole-2-carboxamide; |
| I-119 | 5-{(1S)-1-[(biphenyl-4-ylcarbonyl)amino]-2,2-dimethylpropyl}-N-hydroxythiophene-3-carboxamide; |
| I-123 | 5-{(1S)-1-[(cyclopentylacetyl)amino]propyl}-N-hydroxy-3-methylthiophene-2-carboxamide; |
| I-127 | N-((1S)-1-{5-chloro-4-[(hydroxyamino)carbonyl]-2-thienyl}ethyl)-1-methyl-1H-pyrrole-2-carboxamide; |
| I-131 | 5-{(1S)-1-[(biphenyl-4-ylcarbonyl)amino]ethyl}-2-chloro-N-hydroxythiophene-3-carboxamide; |
| I-133 | 5-((1S)-1-{[(dimethylamino)acetyl]amino}propyl)-N-hydroxy-3-methylthiophene-2-carboxamide; |
| I-134 | 5-{(1S)-1-[(biphenyl-4-ylcarbonyl)amino]ethyl}-3-chloro-N-hydroxythiophene-2-carboxamide; |

-continued

| | |
|---|---|
| I-137 | 5-{(1S)-1-[(2,2-dimethylpropanoyl)amino]propyl}-N-hydroxy-3-methylthiophene-2-carboxamide; |
| I-141 | 2-chloro-5-((1S)-1-{[(dimethylamino)acetyl]amino}ethyl)-N-hydroxythiophene-3-carboxamide; |
| I-142 | N-((1S)-1-{4-[(hydroxyamino)carbonyl]-2-thienyl}-2,2-dimethylpropyl)-1-methyl-1H-indole-2-carboxamide; |
| I-146 | N-((1S)-1-{5-[(hydroxyamino)carbonyl]-4-methyl-2-thienyl}propyl)-1-benzothiophene-2-carboxamide; |
| I-147 | N-((1S)-1-{5-[(hydroxyamino)carbonyl]-4-methyl-2-thienyl}-propyl)-1-methyl-1H-indole-2-carboxamide; |
| I-149 | 5-{(1S)-1-[(2,2-dimethylpropanoyl)amino]-2,2-dimethylpropyl}-N-hydroxythiophene-3-carboxamide; |
| I-150 | 3-chloro-5-{(1S)-1-[(2,2-dimethylpropanoyl)amino]ethyl}-N-hydroxythiophene-2-carboxamide; |
| I-151 | N-((1S)-1-{4-chloro-5-[(hydroxyamino)carbonyl]-2-thienyl}ethyl)-1-methyl-1H-indole-2-carboxamide; |
| I-153 | 5-((1S)-1-{[(dimethylamino)acetyl]amino}-2,2-dimethylpropyl)-N-hydroxythiophene-3-carboxamide; |
| I-184 | N-hydroxy-5-[(1S)-1-({3-[(pyrrolidin-3-ylamino)carbonyl]benzyl}amino)ethyl]thiophene-2-carboxamide; |
| I-187 | N-(4-{[((1R)-1-{5-[(hydroxyamino)carbonyl]-2-thienyl}ethyl)amino]methyl}phenyl)-1-methylpiperidine-4-carboxamide; |
| I-188 | 5-((1R)-1-{[(1-ethylpiperidin-4-yl)methyl]amino}ethyl)-N-hydroxythiophene-2-carboxamide; | or a pharmaceutically acceptable salt thereof.

\* \* \* \* \*